United States Patent [19]

Yanni et al.

[11] Patent Number: 4,810,713

[45] Date of Patent: Mar. 7, 1989

[54] ARYLALKYL-HETEROCYCLIC AMINES, N-SUBSTITUTED BY ARYLOXYALKYL GROUPS USED IN A METHOD FOR ALLERGY TREATMENT

[75] Inventors: John M. Yanni, Chesterfield; David A. Walsh, Richmond, both of Va.

[73] Assignee: A. H. Robins Company, Incorporated, Richmond, Va.

[21] Appl. No.: 811,799

[22] Filed: Dec. 20, 1985

[51] Int. Cl.[4] ............................................ A61K 31/445
[52] U.S. Cl. ........................................ 514/317; 514/318;
514/319; 514/326; 514/826
[58] Field of Search .............. 514/317, 318, 319, 326,
514/826; 546/213, 226

[56] References Cited

U.S. PATENT DOCUMENTS

| | | | |
|---|---|---|---|
| 3,806,526 | 4/1974 | Carr et al. | 546/213 |
| 3,862,173 | 1/1975 | Carr et al. | 546/213 |
| 3,922,276 | 11/1975 | Duncan et al. | 546/226 |
| 3,956,296 | 5/1976 | Duncan et al. | 546/226 |
| 4,391,818 | 7/1983 | Harrison et al. | 514/826 X |
| 4,435,390 | 3/1984 | Annen et al. | 514/826 X |
| 4,443,460 | 4/1984 | Rodriquez et al. | 514/826 X |
| 4,526,999 | 7/1985 | Durette et al. | 514/826 X |

*Primary Examiner*—Leonard Schenkman

[57] ABSTRACT

A method of treating allergy with substituted heterocyclic amines is disclosed wherein the active agents are expressed generally by the formula which includes certain known and certain novel compounds:

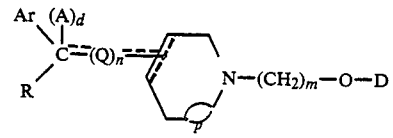

wherein p is zero, one or two; m is one to six inclusive; A is selected from hydrogen, hydroxy or cyano; d is zero or one; Q is —CH—, —CH$_2$— or

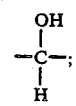

n is zero or one and when Q is —CH— and n is one, a double bond is formed with one of the adjacent carbons but not both at the same time, and when n and d are zero at the same time, a double bond is formed between the α carbon and a carbon of the central heterocyclic amine ring; Ar, D and R are selected from phenyl, substituted phenyl, pyridinyl, thienyl, furanyl or naphthyl and in addition, R may have the values benzyl, substituted benzyl, cycloalkyl or loweralkyl and D may additionally have the values: 2H-1-benzopyran-2-one, 4-oxo-4H-1-benzopyran-2-carboxylic acid loweralkyl ester, 2,3-dihydro-4H-1-benzopyran-4-one or 1,4-benzodioxan-loweralkyl-2-yl, and the pharmaceutically acceptable salts thereof.

101 Claims, No Drawings

ARYLALKYL-HETEROCYCLIC AMINES, N-SUBSTITUTED BY ARYLOXYALKYL GROUPS USED IN A METHOD FOR ALLERGY TREATMENT

BACKGROUND OF THE INVENTION

1. Field of Invention

This invention relates to a method of treating allergy in a living animal body with piperidinyl, pyrrolidinyl, and homopiperidinyl derivatives substituted on nitrogen by aryloxyalkyl radicals and otherwise substituted by aryl (or diaryl)-alkanol, aryl (or diaryl)-alkyl and aryl (or diaryl)alkylidine radicals. The invention thus contemplates the use of the aforementioned heterocyclic amine derivatives defined by Formula I hereinbelow in treating allergic phenomena which includes but is not limited to asthma, rhinitis, atopic dermatitis, chronic hives and the like.

2. Information Disclosure Statement

Various systemic anti-allergy agents have long been known prior to this invention including, among others, aminophylline, theophylline, cortisosteroids, the disodium salt of 1,3-bis(2-carboxychromon-5-yloxy)-2-hydroxypropane, α-[(tertbutylamino)methyl]-3,5-dihydroxybenzylalcohol sulfate and oxatomide. The efficacy of some has suffered from undesirable side effects while others which are effective prophylactically are ineffective in acute manifestations of the allergic attack. By way of comparison, for example, the preferred compounds of the present invention are many times more potent than aminophylline and several times more potent than oxatomide.

Olefinic-4-substituted piperidino derivatives useful as antihistaminic, antiallergy agents and bronchodilators represented by the formula

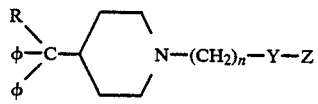

are disclosed in U.S. Pat. No. 3,862,173 wherein R represents hydrogen or forms a double bond, Y represents —CH=CH— and Z represents thienyl, phenyl or phenyl substituted by halogen, alkyl, loweralkoxy, diloweralkylamino, pyrrolidino, piperidino, morpholino or N-loweralkylpiperazino. Compounds useful in the present invention differ in that an ether linkage is present and there is no unsaturation in the alkyl chain.

Diphenylmethylene-piperidineacetic acid derivatives useful as anti-allergic, anti-histaminic, and broncholytic agents are disclosed in European Pat. No. 48705B and have the formula:

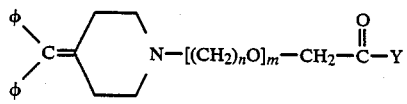

wherein Y is OH or NR$_1$R$_2$; compounds useful in the present invention have an aryl group next to the ether oxygen.

U.S. Pat. No. 3,806,526 discloses 1-aroylalkyl-4-diphenylmethylpiperidines having antihistaminic, anti-allergenic and bronchodilator activity. In contrast, the compounds useful in the present invention have aryloxyalkyl radical on piperidine and pyrrolidine nitrogen rather than an aroylalkyl radical.

A number of the compounds useful in the present method of treating allergy have been disclosed specifically and under generic formulas in U.S. Pat. Nos. 3,922,276 and 3,956,296 as being useful as anti-inflammatory agents, tranquilizers and sedatives. These activities are not suggestive of use in treating allergy.

SUMMARY OF THE INVENTION

The heterocyclic amines useful in the antiallergy method of this invention are disubstituted and have the general formula:

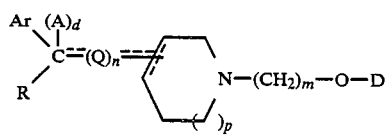

Formula I wherein;

p is zero, one or two;
m is one to six inclusive;
A is hydrogen, hydroxy, or cyano;
d is zero or one;
Q is —CH—, —CH$_2$— or

n is zero or one;
and when Q is —CH— and n is 1, a double bond is formed with one of the adjacent carbons, but not both, and when n and d are zero at the same time, a double bond is formed between the α-carbon and a carbon of the central heterocyclic amine ring;
Ar, D and R are selected from the group consisting of:

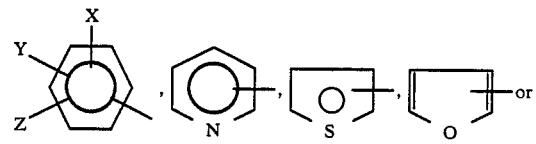

and in addition, R may have the values:

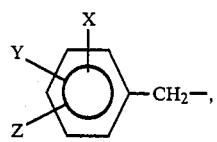

cycloalkyl or loweralkyl; and D may have additionally the values:

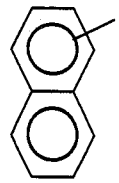

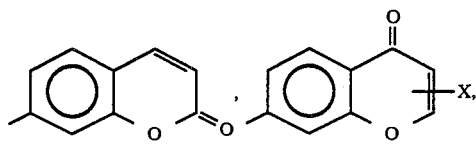

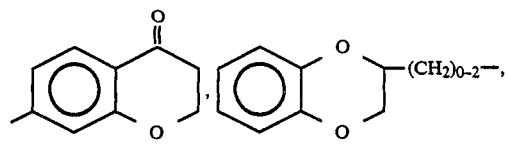

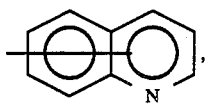

or Ar(CH₂)₁₋₄—; X, Y, and Z are selected from the group consisting of hydrogen, loweralkyl, halogen,

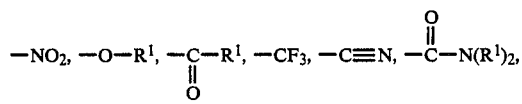

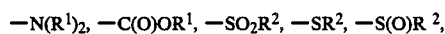

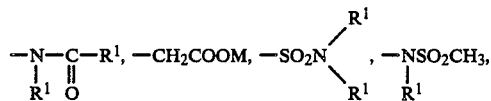

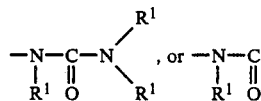

$R^1$ is selected from hydrogen, loweralkyl, phenyl and phenylloweralkyl; $R^2$ is selected from loweralkyl, phenyl and phenylloweralkyl; M is a pharmaceutically acceptable metal ion; and the pharmaceutically acceptable salts thereof, including acid addition salts, quaternary salts and hydrates and alcoholates thereof.

In the further definition of symbols in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl, and octyl radicals and the like. The term "loweralkoxy" has the formula —O—loweralkyl.

The term "cycloalkyl" as used herein includes primarily cyclic alkyl radicals containing 3–7 carbon atoms inclusive and includes such groups as cyclopropyl, cyclobutyl, cyclopentyl, cyclohexyl, cycloheptyl and methylcyclohexyl and the like.

The term "halo" or "halogen" when referred to herein includes fluorine, chlorine, bromine and iodine unless otherwise stated.

The term "central heterocyclic amine ring" refers to that portion of Formula I represented by

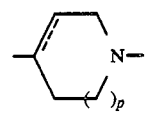

The term "phenylloweralkyl" includes phenyl connected by hydrocarbon chains exemplified by loweralkyl above and wherein phenyl may be substituted by non-reactive or non-interfering radicals such as halo, loweralkyl, loweralkoxy, and the like.

"Pharmaceutically acceptable salts" include acid addition salts, hydrates, alcoholates and quaternary salts of the compounds of Formula I which are physiologically compatible in warm-blooded animals. The acid addition salts may be formed by either strong or weak acids. Representative of strong acids are hydrochloric, hydrobromic, sulfuric, and phosphoric acids. Representative of weak acids are fumaric, maleic, mandelic, tartaric, citric, oxalic, succinic, hexamic, and the like. Suitable quaternary salts include the loweralkyl halides and loweralkyl sulfates.

The primary screening method used to detect anti-allergy properties of the compounds of Formula I is a modification of the procedure of R. R. Martel and J. Klicius, Intern. Arch. Allergy Appl. Immunology, vol. 54, pp 205–209 (1977) which measures the effect of oral administration of the compound on the volume of a rat paw which was previously injected with anti-egg albumin serum and is described in detail under Pharmacology Methods hereinbelow.

A method of studying potency in preventing guinea pig anaphylaxis relative to known anti-allergy drugs is also described hereinbelow under Pharmacology Methods. Generally, about 200 times more theophylline and 5–15 times more oxatomide are required than the more active compounds used in the present method.

The above tests are useful in determining the ability of a compound to inhibit Type I allergic responses in a living animal and their usefulness in treating allergic phenomena which includes asthma, rhinitis, atopic dermatitis, chronic hives, allergic conjunctivitis and the like.

DETAILED DESCRIPTION OF THE INVENTION

Anti-allergy agents of Formula I above useful in the method of treating allergy of this invention may be prepared by methods described in U.S. Pat. Nos. 3,922,276 and 4,032,642. One of the general methods used in the detailed examples hereinbelow is outlined by equation in Chart I (Method A). This reaction can be carried out in alcoholic solvents, preferably refluxing butanol or in dimethylformamide, dimethoxyethane in the presence of an acid receptor as, for example, an alkali-metal carbonate, and preferably using potassium iodide catalyst. The reaction time may vary from a few hours to 24 hr, depending on reactivity of the aryloxyalkyl halide and temperature. Temperature can vary from about 80° C. to 125° C. Products are isolated, usually by partitioning in a solvent such as methylene chloride, chloroform or benzene and the like and a weak basic aqueous solution and washing, drying and concentrating the organic layer to give the free base which may then be converted, if desired, to an acid addition salt in a conventional manner.

Alternate Method B is shown by equation in Chart II. This reaction may be carried out in a suitable solvent such as tetrahydrofuran at room temperature for several hours. Preparation and isolation of the free base and a salt is typically described in Example 4.

Alternate Method C is shown by equation in Chart III. This reaction is suitable only when there is no other hydroxy radical present.

Mesylation or tosylation with such as mesyl or tosyl chloride is conducted in the presence of an acid receptor such as a tertiary amine; e.g., triethylamine, while cooling. The final reaction of the mesylate or tosylate with the D-OM+ is conducted in a suitable organic solvent and the product free base is isolated by conventional means such as washing, extracting with an acid solution and an organic solvent and evaporating the solvent.

Alternate Method D is shown by equation in Chart IV. The method is limited to preparation of certain derivatives such as wherein D is 2-pyridinyl or 2-quinolinyl. Dimethyl sulfoxide is a suitable solvent and 60° C. is a suitable temperature for the reaction.

CHART I
Preparation of Compounds of Formula I:

Method A.

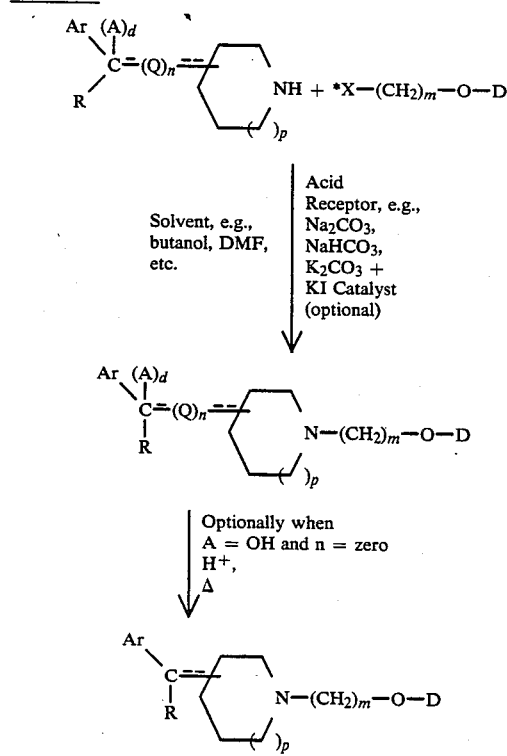

*X = halide

CHART II
Alternate Preparation of Compounds of Formula I:
Method B.
(R = Ar, Q = zero)

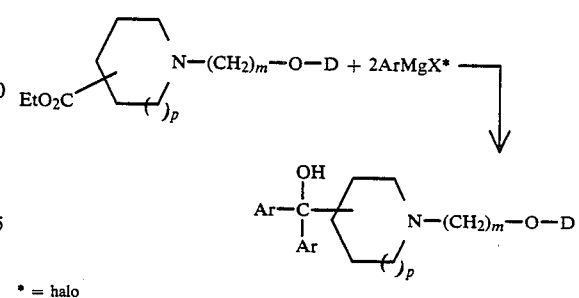

* = halo

CHART III
Alternate Preparation of Compounds of Formula I:
Method C. When No Other Hydroxy is Present.

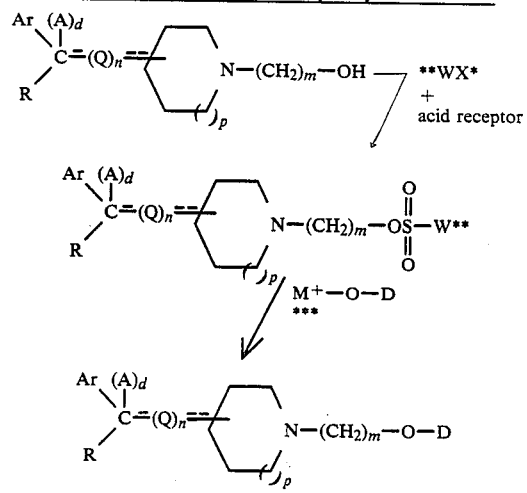

Footnotes:
*X = halo.
**W = mesyl, tosyl, etc.
***M = alkali-metal ion.

CHART IV
Alternate Preparation of Compounds of Formula I:

Method D.

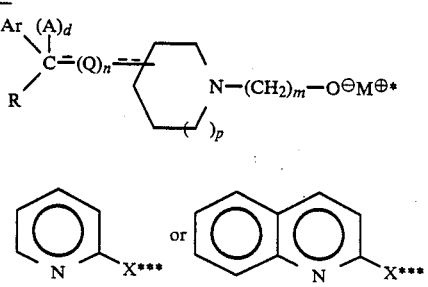

-continued
CHART IV
Alternate Preparation of Compounds of Formula I:

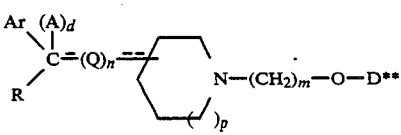

°$M^{\oplus}$ = alkali-metal ion.
**D = pyridin-2-yl or quinolin-2-yl.
***X = halo (Br, Cl).

To prepare acid addition salt, the free base is reacted with the calculated amount of organic or inorganic acid in aqueous miscible solvent such as ethanol or isopropanol, with isolation by concentration and/or cooling, or the base is reacted with an excess of the acid in aqueous immiscible solvent such as diethyl ether or isopropyl ether, with the desired salt separating directly. Exemplary of such organic salts are those formed with oxalic, maleic, fumaric, benzoic, ascorbic, pamoic, succinic, methanesulfonic, acetic, propionic, tartaric, citric, lactic, malic, citraconic, itaconic, hexamic, p-aminobenzoic, glutamic and stearic acid and the like. Exemplary of such inorganic salts are those formed with hydrochloric, hydrobromic, sulfuric, sulfamic, phosphoric and nitric acids.

If desired, the free base may be regenerated by proportioning the acid addition salt between an organic solvent such as methylene chloride and a weakly basic aqueous solution of, for example, sodium bicarbonate and separating the methylene chloride layer and evaporating it.

While, as stated above, the compounds of Formula I have generally exhibited positive anti-allergy utility, certain compounds encompassed by Formula I are more potent and therefore preferred and have the formula:

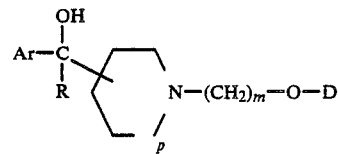

Ia wherein p is zero or one; Ar, R, m and D have the values assigned under Formula I, and the pharmaceutically acceptable acid salts thereof.

Precursors (Chemical Intermediates) used in the synthesis of compounds of Formula I are prepared in a number of ways as illustrated by the following (1) to (9) sets of equations which are also applicable to pyrrolidinyl and homopiperidinyl derivatives. (See also U.S. Pat. Nos. 3,922,276 and 3,956,296):

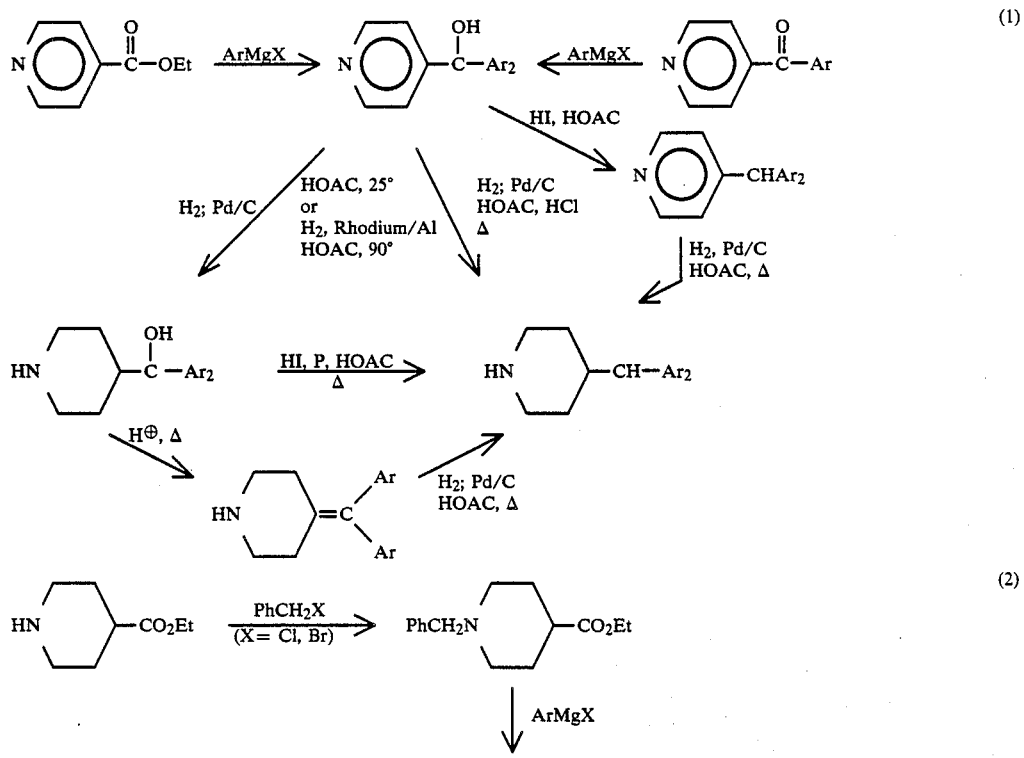

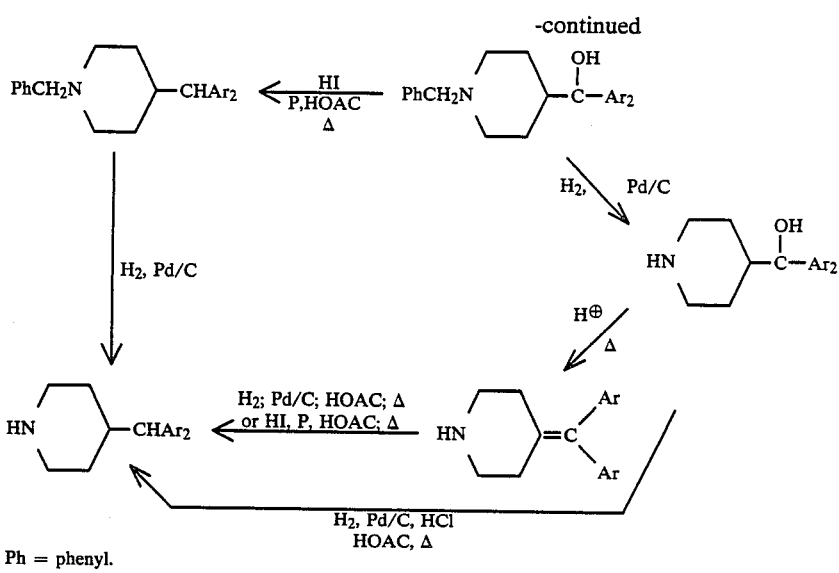
Ph = phenyl.
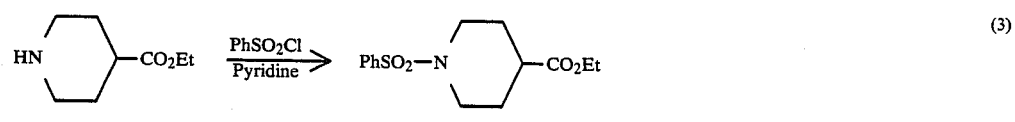
(3)
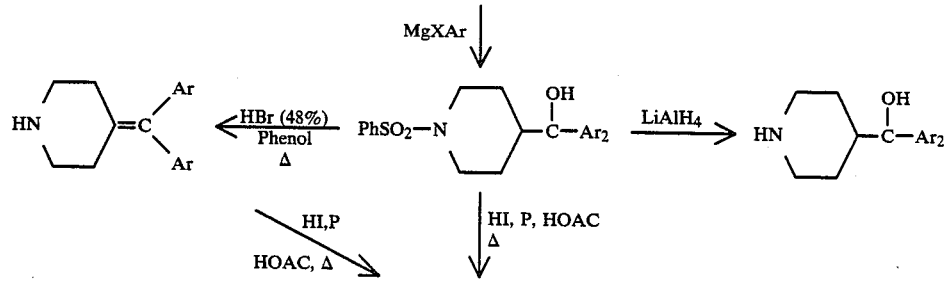
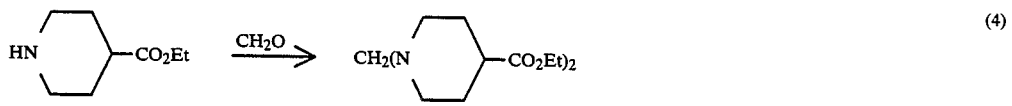
(4)
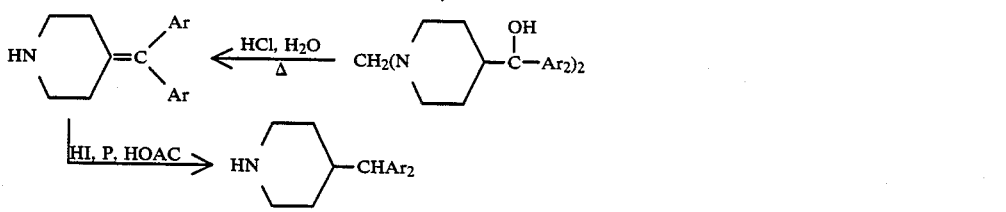
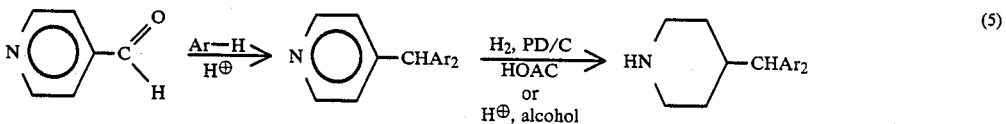
(5)
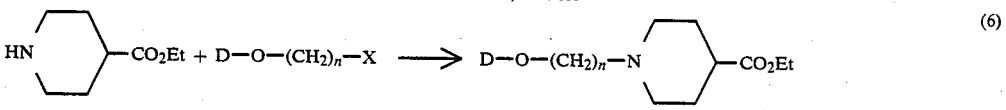
(6)
X = Cl, Br
Ph = phenyl.

-continued
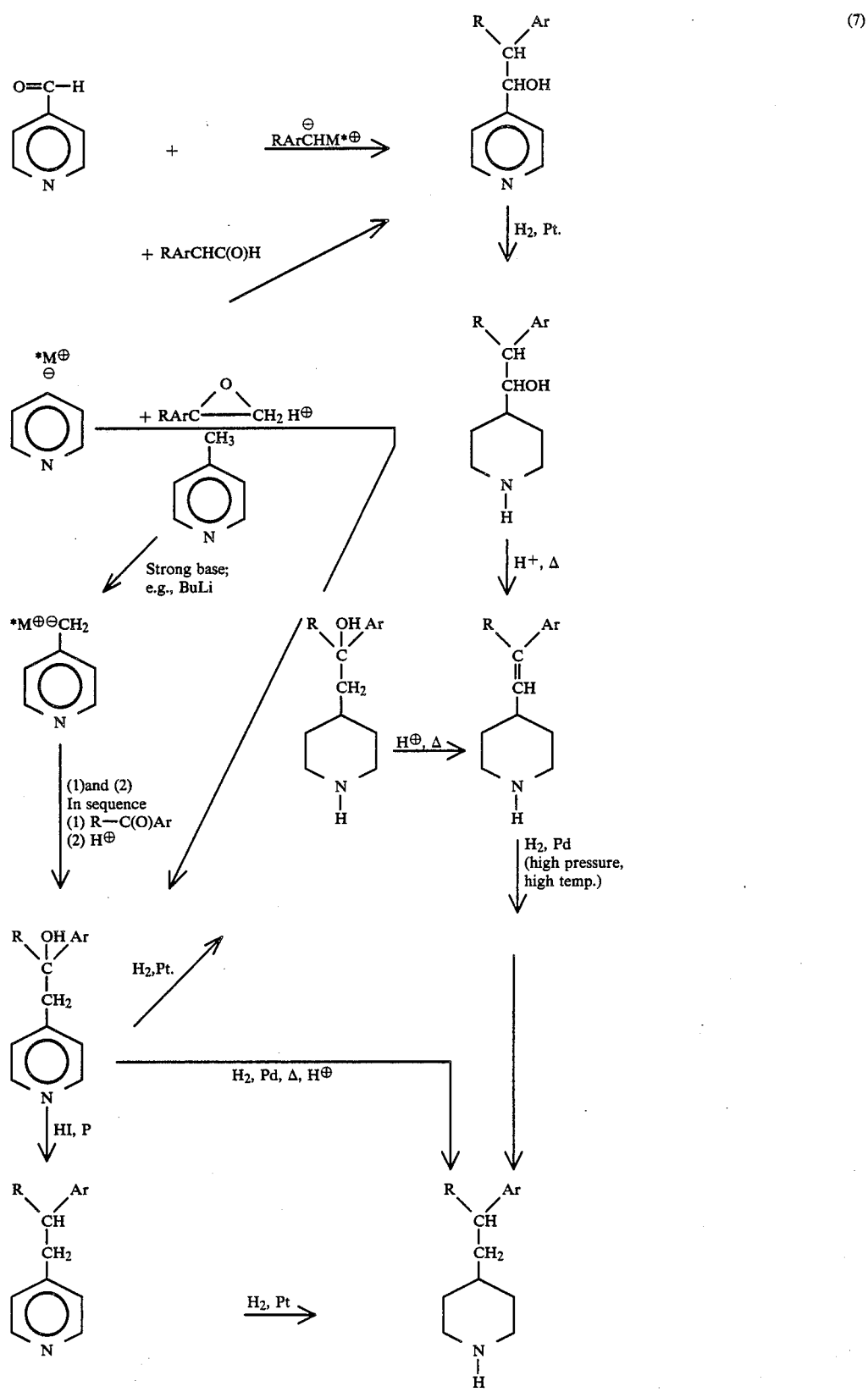
(7)
*M⊕ = Li⊕ or MgBr⊕

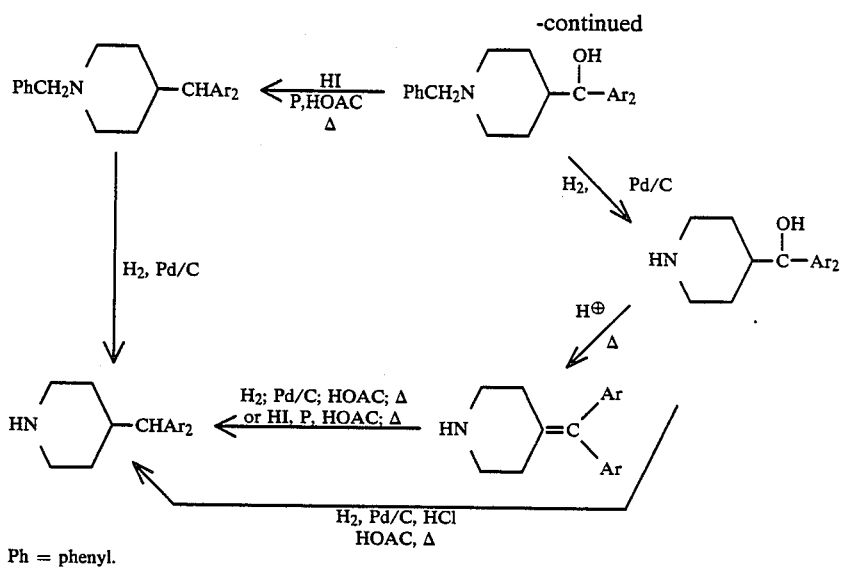
Ph = phenyl.
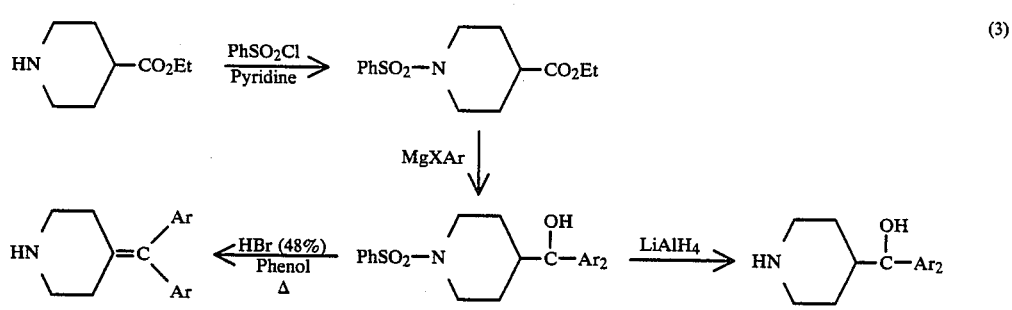
(3)
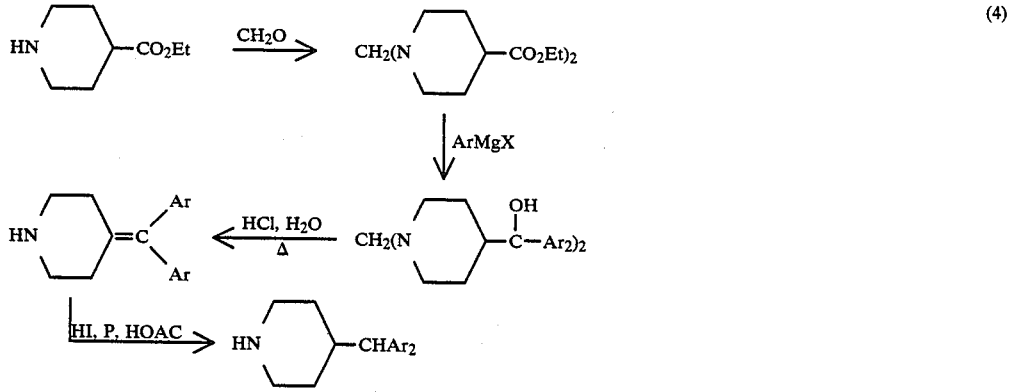
(4)
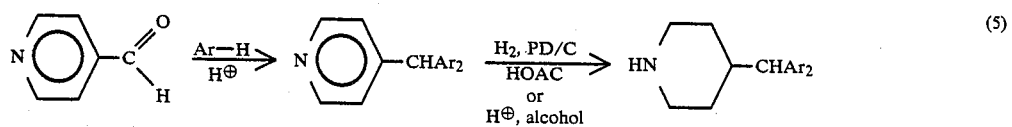
(5)
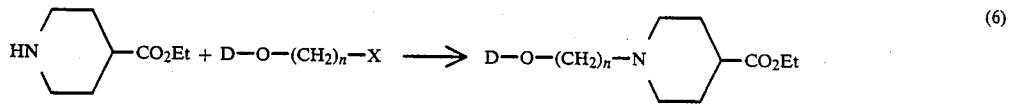
(6)
X = Cl, Br
Ph = phenyl.

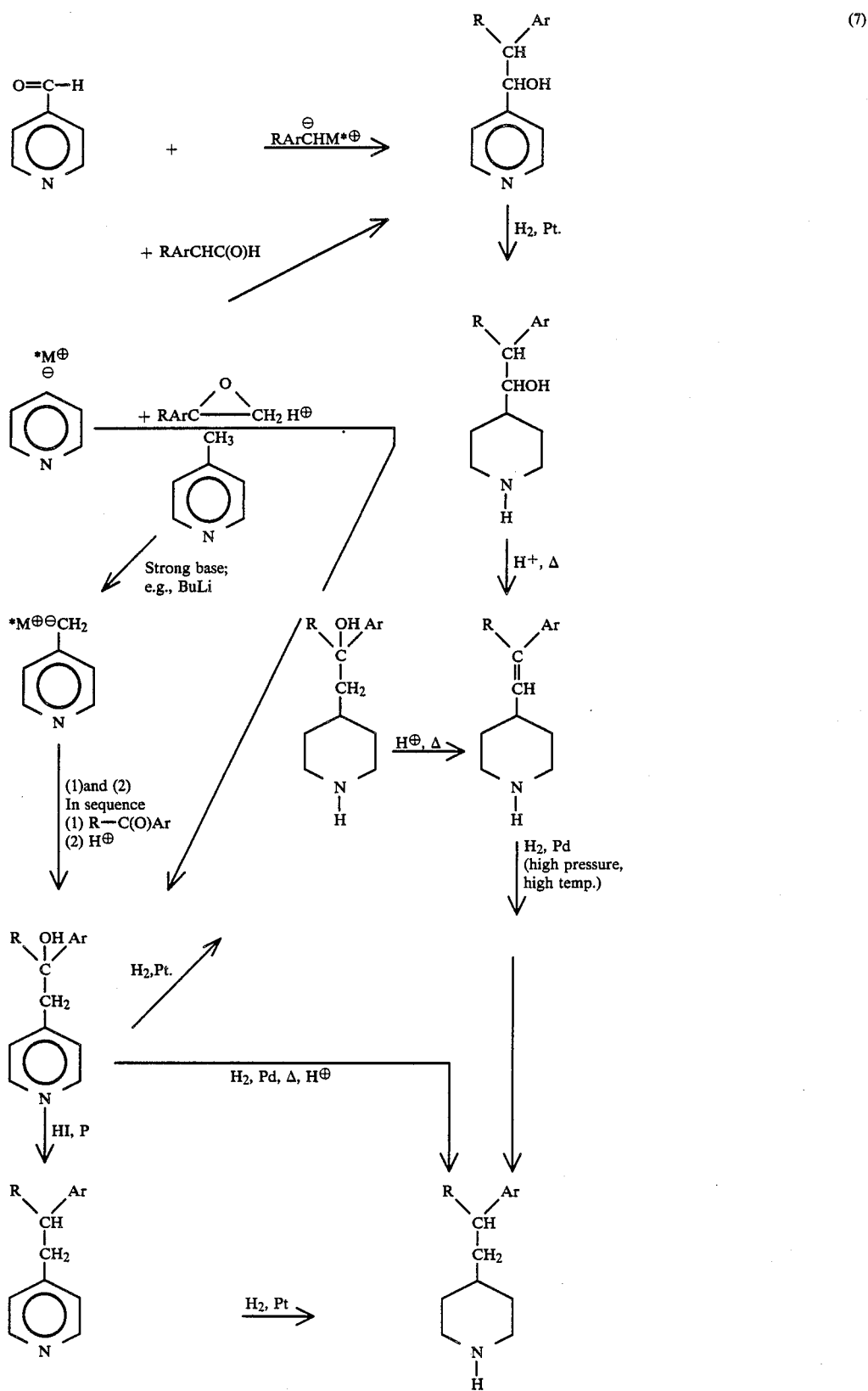
*M⊕ = Li⊕ or MgBr⊕

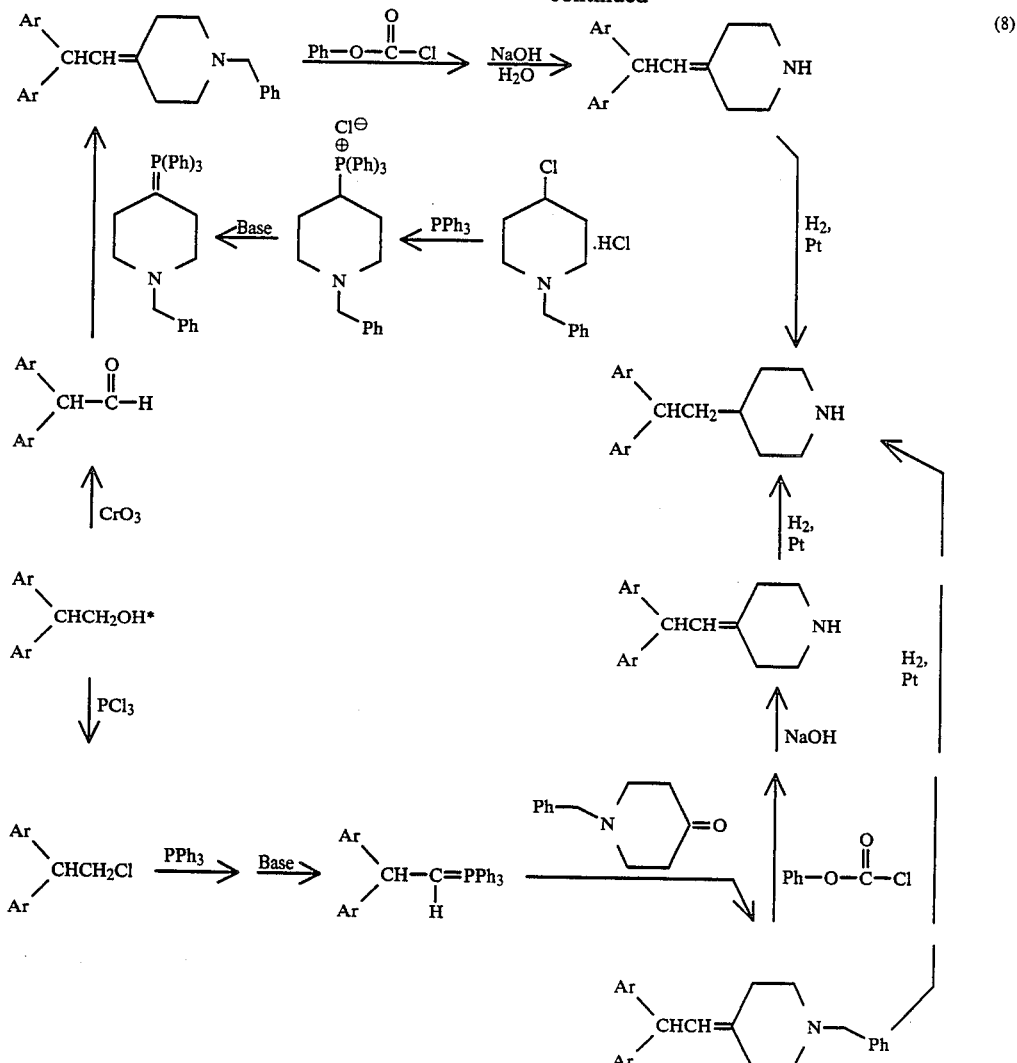
*Commercially available
Ph = phenyl
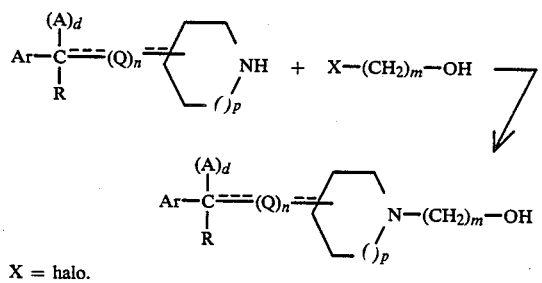
X = halo.
The method of preparation of certain starting materials wherein D is phenyl substituted by hydroxy is illustrated by the following equations:
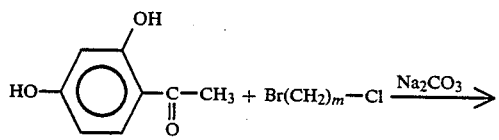
-continued
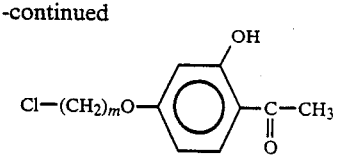
The preparation of other hydroxyphenyl intermediates and compounds is illustrated by the following equation:

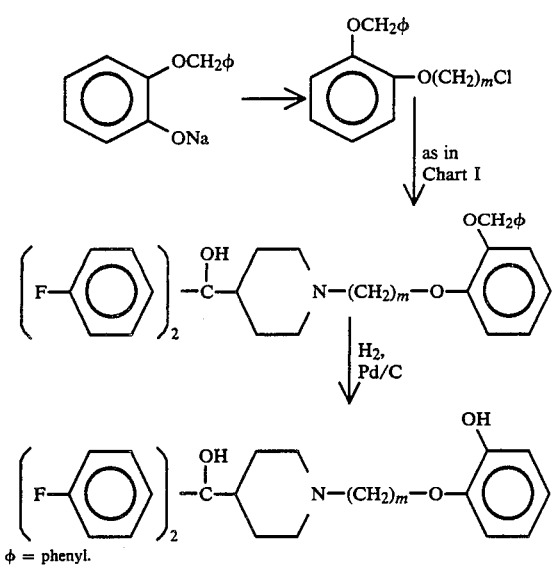

The preparation of certain substituted phenol starting materials is illustrated by the following equations:

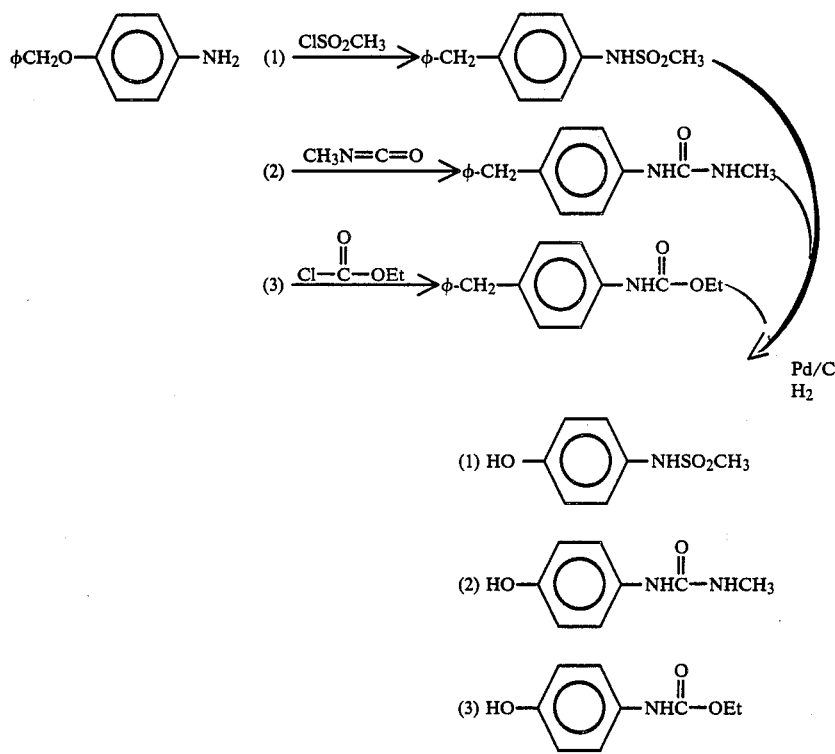

φ = phenyl

The preparation of chemical intermediates is further illustrated in the following Preparations 1 to 64. Examples 1 to 114 illustrate the synthesis methods for preparing compounds of Formula I. The scope of the invention is not limited by the descriptive methods and procedures of the preparations and examples, however.

PREPARATION 1

4-Diphenylmethylenepiperidine

A solution of 7.0 g of 1-acetyl-4-diphenylhydroxymethylpiperidine in 30 ml of absolute alcohol and 76 ml of concentrated hydrochloric acid was heated at reflux for seven hours, cooled and made basic with 50% sodium hydroxide. The oil which separated was extracted with benzene and the combined extracts washed with water. After drying over magnesium sulfate the solvent was evaporated at reduced pressure. The residual oil which crystallized on cooling was recrystallized twice from petroleum ether to give 4.0 g (73.0%) of white crystals, m.p. 85°–86° C.

Analysis: Calculated for $C_{18}H_{19}N$: C, 86.70; H, 7.68; N, 5.62. Found: C, 86.70; H, 7.83; N, 5.73.

PREPARATION 2

[α,α-Bis(p-fluorophenyl)]-4-piperidinemethanol hydrochloride hydrate [1:1:0.5]

This compound was prepared by the method described in Preparation 1 of U.S. Pat. No. 4,032,642, m.p. 243°–243.5° C. from the Grignard reagent formed with p-fluorobromobenzene and 1-acetyl-4-(p-fluorobenzoyl)piperidine followed by hydrolysis and conversion to the salt.

PREPARATION 3

1-(Phenylmethyl)-4-piperidinecarboxylic acid ethyl ester hydrochloride [1:1]

A mixture of 100 g (0.637 mole) of ethyl isonipecotate, 80.64 g (0.64 mole) of benzyl chloride and 67.84 g (0.64 mole) of sodium carbonate in 1 liter of absolute ethanol was refluxed for 8 hours and then was stirred at room temperature for 10 hours. The solvent was removed in vacuo, and the residue was partitioned between methylene chloride and dilute sodium hydroxide. The methylene chloride phase was dried over magnesium sulfate and the solvent was removed in vacuo to give the free base of the title compound as a liquid. The free base was converted to the hydrochloric acid salt, and the salt was recrystallized from ethanol-ether to give 89.33 g (49.7%) of white crystalline solid, m.p. 154°–155° C.

Analysis: Calculated for $C_{15}H_{22}NO_2Cl$: C, 63.48; H, 7.81; N, 4.94. Found: C, 63.07; H, 7.82; N, 4.91.

PREPARATION 4
α,α-Bis-(4-fluorophenyl)-1-(phenylmethyl)-4-piperidinemethanol

To a 6.08 g (0.25 mole) of magnesium turnings and an iodine crystal in 600 ml of dry tetrahydrofuran and under an atmosphere of nitrogen was added, dropwise, a solution of p-bromofluorobenzene in 125 ml of tetrahydrofuran. The temperature of the reaction was kept below 10° C. by cooling in an ice-methanol bath. The mixture was stirred at room temperature for 1.5 hours. A solution of 24.7 g (0.10 mole) of 1-(phenylmethyl)-4-piperidinecarboxylic acid ethyl ester hydrochloride in tetrahydrofuran was added, and the mixture was stirred at room temperature for 17 hours. The reaction was poured into an icy, aqueous solution of ammonium chloride, and the resulting solution was extracted with methylene chloride. The methylene chloride solution was extracted with dilute sodium hydroxide and was dried over magnesium sulfate. The solvent was removed in vacuo to give an oil. This was crystallized from ether-hexane to give 19.87 g (51%) of the title compound, m.p. 113°–115° C.

Analysis: Calculated for $C_{25}H_{25}NOF_2$: C, 76.31; H, 6.40; N, 3.56. Found: C, 76.24; H, 6.38; N, 3.50.

PREPARATION 5
[α,α-Bis(p-fluorophenyl)]-4-piperidinemethanol

A solution of 31.2 g (0.079 mole) of α,α-bis-(4-fluorophenyl)-1-(phenylmethyl)-4-piperidinemethanol in 400 ml of absolute ethanol was hydrogenated at 50 psi and 70° C. over 5% palladium on carbon over the weekend. The mixture was filtered and the filtrate was concentrated under reduced pressure to give a gum as residue. Methylene chloride was added to the residue and the gum crystallized. The mixture was diluted with petroleum ether and the solid was collected by filtration, washed with petroleum ether, and dried to yield 22 g (92%) of white solid which was recrystallized from isopropyl ether-2-propanol, m.p. 159.5°–160.5° C.

Analysis: Calculated for $C_{18}H_{19}F_2NO$: C, 71.27; H, 6.31; N, 4.62. Found: C, 70.93; H, 6.71; N, 4.38.

PREPARATION 6
1-(Phenylsulfonyl)-4-piperidinecarboxylic acid, ethyl ester

To a solution of 10.1 g (0.0642 mole) of ethyl isonipecotate in 300 ml of pyridine and cooled in an ice bath was added 13.2 g (0.075 mole) of benzene sulfonyl chloride. The mixture was stirred for 2 hours at room temperature, and the solvent was removed in vacuo. The residue was partitioned between methylene chloride and dilute sodium hydroxide. The methylene chloride solution was dried over magnesium sulfate, and the solvent was removed in vacuo to give a solid. This was recrystallized from ethanol-ether to give 4.59 g (24.1%) of crystalline solid; m.p. 85–86.5.

Analysis: Calculated for $C_{14}H_{19}NO_4S$: C, 56.55; H, 6.44; N, 4.71. Found: C, 56.53; H, 6.55; N, 4.67.

In another preparation, 100 g (0.634 mole) of ethyl nipecotate and 130.4 g (0.74 mole) of benzene sulfonyl chloride were reacted by the above procedure for 4½ hr. to give the title product in 78.1% yield.

PREPARATION 7
α,α-Bis(4-fluorophenyl)-1-(phenylsulfonyl)-4-piperidinemethanol To a suspension of 33.78 g (1.39 mole) of magnesium trimmings in 1 liter of tetrahydrofuran (dried over molecular sieves 5A) under an atmosphere of $N_2$ and cooled in an ice bath was added dropwise a solution of 243.25 g (1.39 mole) of p-bromofluorobenzene in 150 ml of tetrahydrofuran. The mixture was stirred for 2 hr after the addition was completed. To this mixture was added 103 g (0.346 mole) of 1-(phenylsulfonyl)-4-piperidinecarboxylic acid ethyl ester as a solid, and the solution was stirred at ambient temperature for 5 hr. The reaction was poured into an icy aqueous solution of ammonium chloride. The phases were separated, and the solvent was removed in vacuo from the organic phase. The residue was partitioned between methylene chloride and dilute sodium hydroxide. The methylene chloride solution was dried over magnesium sulfate and was reduced in vacuo to ≅1 liter volume. The title compound was obtained by adding hexane and cooling, recrystallizing the precipitate from ethyl acetate and hexane and drying the solid under high vacuum at 130° C. for 45 min. at which time the product had partially melted, m.p. 142.5°–144° C.

Analysis: Calculated for $C_{24}H_{23}NO_3SF_2$: C, 65.00; H, 5.23; N, 3.16. Found: C, 65.21; H, 5.30; N, 3.10.

PREPARATION 8
4-[Bis(4-fluorophenyl)methylene]-1-(phenylsulfonyl)-piperidine

A solution of 5.23 g (0.0118 mole) of α,α-bis(4-fluorophenyl)-1-(phenylsulfonyl)-4-piperidinemethanol in 100 ml of acetic acid and 20 ml of 2M sulfuric acid was refluxed for 2½ hours and then poured over ice. The mixture was made basic with 50% sodium hydroxide and the basic mixture was extracted with methylene chloride. The methylene chloride solution was dried (anhydrous sodium sulfate), and the solvent was removed in vacuo. The residue was recrystallized from ether-hexane to give 3.23 g (64.4%) of white crystalline solid, m.p. 90°–92.5° C.

Analysis: Calculated for $C_{24}H_{21}NO_2SF_2$: C, 67.75; H, 4.98; N, 3.29. Found: C, 67.73; H, 5.00; N, 3.21.

PREPARATION 9
4-[Bis(4-fluorophenyl)methylene]piperidine hydrobromide [1:1]

A mixture of 164 g (0.342 mole) of α,α-[bis(4-fluorophenyl)]-1-(phenylsulfonyl)-4-piperidinemethanol and 80 g (0.85 mole) of phenol in 700 ml of 48% hydrobromic acid was refluxed for 7 hr and then was stirred at room temperature for 9 hr. The hydrobromic acid solution was decanted from a gum in the bottom of the reaction flask. The gum was triturated with ~1 liter of ether, and a tan solid formed. The solid was washed with several portions of ether and was dried under high vacuum to give 9.13 g (73%) of slightly impure title product, m.p. 211°–215° C. A small sample of this solid was recrystallized from methanol to give an analytically pure sample as a crystalline solid; m.p. 216°–218° C.

Analysis: Calculated for $C_{18}H_{18}NBrF_2$: C, 59.03; H, 4.95; N, 3.82. Found: C, 58.96; H, 4.98; N, 3.76.

PREPARATION 10

4-[Bis(4-fluorophenyl)methyl]piperidine fumarate hydrate [1:1:0.5]

A mixture of 30.6 (0.99 mole) of phosphorous and 15.1 g (0.059 mole) of iodine in 90 ml of glacial acetic acid was stirred for 20 min at room temperature. A mixture of 6 ml of water, 70 ml of methanesulfonic acid, 56.19 g (0.197 mole) of 4-[bis(4-fluorophenyl)methylene]piperidine and 110 ml of glacial acetic acid was added, and the mixture was refluxed for 7 hr. The solvent was removed in vacuo, and the resulting viscous liquid was poured over ice. The icy mixture was made basic with 50% sodium hydroxide, and the basic suspension was extracted with methylene chloride. The methylene chloride solution was extracted with an aqueous solution of sodium thiosulfate and was dried over anhydrous sodium sulfate, and the solution was filtered through celite. The solvent was removed in vacuo to give a gum. The gum was dissolved in 400 ml of hot methanol, and 4.25 g of an unknown tan solid was collected from the warm solution. Fumaric acid (22 g, 0.190 mole) was added to the methanolic solution followed by the addition of ether. A white precipitate was collected to give 22.55 g (32.3%) of crystalline solid; m.p. 208°–209° C.

Analysis: Calculated for $C_{20}H_{22}NO_{2.5}F_2$: C, 67.78; H, 6.26; N, 3.95. Found: C, 67.86; H, 6.12; N, 3.81.

PREPARATION 11

4-[α-(p-Fluorophenyl)-α-phenylmethyl]piperidine hydrochloride [1:1]

This compound was prepared as described in U.S. Pat. No. 4,032,642 by hydrogenation of α-(p-fluorophenyl)benzylidinepiperidine over palladium charcoal catalyst, m.p. 81°–82° C.

Analysis: Calculated for $C_{18}H_{21}ClFN$: C, 70.69; H, 6.92; N, 4.58. Found: C, 70.69; H, 6.93; N, 4.52.

PREPARATION 12

1-[4-(3-Chloropropoxy)-3-methoxyphenyl]ethanone

To a mixture of 15.15 kg (96.26 mole) of 1-bromo-3-chloropropane and 25 liter of water heated to 86° C. was added a solution of 8 kg (48.13 mole) of acetovanillone in 3.93 kg (48.6 mole) of 50% aqueous sodium hydroxide and 89 liter of water over a 2.5 hr period. The mixture was heated at 80°–85° C. for 2–5 hr after addition was complete. The mixture was cooled and extracted twice with 49 kg portions of toluene. The combined extracts were washed once with 1.9 kg of 50% sodium hydroxide diluted to 5 gal and once with 5 gal of water. The toluene layer was dried over 3 lb of anhydrous sodium sulfate and concentrated under reduced pressure. The residue was heated to reflux in 15 gal of diisopropylether, filtered, and the filtrate cooled. The crystallized title compound obtained by filtration together with additional compound obtained by concentrating the filtrate to 25% of its original volume amounted to 4.2 kg (36%). Acetovanillone recovered was 3.4 kg. The product was recrystallized twice from cyclohexane and twice from ligroin, m.p. 57.8°–58.5° C.

Analysis: Calculated for $C_{12}H_{15}ClO_3$: C, 59.39; H, 6.23. Found: C, 59.07; H, 6.22.

PREPARATION 13 cl

1-(3-Phenoxypropyl)-4-piperidinecarboxylic acid ethyl ester oxalate [1:1]

A mixture of ethyl isonipecotate (35.5 g, 0.226 mole) 3-phenoxy-1-bromopropane (51.6 g, 0.24 mole) and sodium carbonate (25.4 g, 0.24 mole) in 500 ml of absolute ethanol was refluxed for 16 hr. The solvent was removed in vacuo, and the residue was partitioned between methylene chloride and dilute sodium hydroxide. The solution was dried over anhydrous sodium sulfate and the solvent was removed in vacuo to give a liquid. The liquid was dissolved in absolute ethanol, and a solution of oxalic acid (~0.23 mole) in absolute ethanol was added. The product 73.43 g (87.7%) precipitated as a white, crystalline solid, m.p. 180°–181.5° C.

Analysis: Calculated for $C_{19}H_{27}NO_7$: C, 59.83; H, 7.14; N, 3.67. Found: C, 59.76; H, 7.17; N, 3.64.

PREPARATION 14

4-[Bis(4-fluorophenyl)methylene]-1-(phenylmethyl)-piperidine maleate [1:1]

A mixture of αα-bis(4-fluorophenyl)-1-(phenylmethyl)-4-piperidinemethanol (5.09 g, 0.013 mole) in 200 ml of acetic acid and 10 ml of 2M sulfuric acid was refluxed for 2 hr. The solvent was removed in vacuo, and the residue was partitioned between methylene chloride and dilute sodium hydroxide. The methylene chloride solution was dried over magnesium sulfate and the solvent was removed in vacuo to give the free base of the title compound as a solid. The free base was dissolved in methanol-diethylether and maleic acid (excess) was added. The product 5.24 g (82.1%) precipitated as a white, crystalline solid, m.p. 180°–181.5° C.

Analysis: Calculated for $C_{29}H_{27}NF_2O_4$: C, 70.86; H, 5.54; N, 2.85. Found: C, 70.80; H, 5.45; N, 2.79.

PREPARATION 15

α,α-Bis(4-fluorophenyl)-4-pyridinemethanol

The Grignard reagent was prepared from 4-bromofluorobenzene (66.6 g, 0.381 mole) and magnesium (9.13 g, 0.381 mole) in tetrahydrofuran (ice bath). The Grignard reagent was stirred at room temperature for 1½ hr. and transferred (under $N_2$) to an addition funnel. This solution was added dropwise to a tetrahydrofuran solution of ethyl isonicotinate (25.0 g, 0.165 mole) (ice bath cooling). The reaction mixture was stirred 3 hr at room temperature and poured onto ice containing ammonium chloride (28 g, 0.5 mole). The mixture was allowed to stand overnight. The reaction mixture was diluted to 3 liter with water and extracted with chloroform. The chloroform layer was back extracted with dilute sodium hydroxide. Removal of chloroform gave a gummy brown solid. The brown solid was triturated with methanol-diethyl ether (10–120 v/v) and placed in the refrigerator freezer. Solid was filtered off and dried overnight in vacuo at 80° C. to give 11.96 g (24%) of white crystalline product, m.p. 185°–189° C.

Analysis: Calculated for $C_{18}H_{13}NOF_2$: C, 72.72; H, 4.41; N, 4.71. Found: C, 72.76; H, 4.39; N, 4.67.

PREPARATION 16

4-[Bis(4-fluorophenyl)methyl]-1-(phenylmethyl)piperidine, fumarate [1:1]

A mixture of 4.3 g (0.139 mole) of phosphorous, 44 g (0.196 mole) of a 57% aqueous solution of hydrogen iodide and 4.15 g (0.0106 mole) of 4-[bis(4-fluorophenyl)methylene]-1-(phenylmethyl)piperidine in 60 ml of glacial acetic was refluxed for 1 hr. The mixture was poured over ice and was made basic with 50% sodium hydroxide. The aqueous mixture was extracted with methylene chloride. The methylene chloride solution was extracted with an aqueous solution of sodium sulfite and was dried over magnesium sulfate. The solvvent was removed in vacuo to give 3.89 g (89%) of the free base of the title compound. The free base was converted to the fumarate salt, and the salt was recrystallized from methanol-ether to give 3.62 g (69.3%) white solid; m.p. 201°–202° C.

Analysis: Calculated for $C_{29}H_{29}NO_4F_2$: C, 70.57; H, 5.92; N, 2.84. Found: C, 70.69; H, 5.95; N, 2.81.

PREPARATION 17

4-(2-Chloroethoxy)benzoic acid ethyl ester

A mixture of 71.7 g (0.5 mole) of 1-bromo-2-chloroethane, 83.1 g (0.5 mole) of ethyl p-hydroxybenzoate and 69.1 g (0.5 mole) of potassium carbonate in 200 ml of acetone was heated at reflux for 40 hr. The solids were removed by filtration and the filtrate was evaporated under reduced pressure to leave a semi-solid residue. The residue was triturated with 200 ml of 5% sodium hydroxide solution and filtered.[1] The filter cake was washed with water (100 ml) and dried to give 42.4 g (80%)[2] of a solid. A sample was recrystallized from benzene-petroleum ether (30°–60° C.) to give white solid, m.p. 74°–76° C.

[1] The filtrate pH was adjusted to 2 with concentrated hydrochloric acid. The resulting solid was collected by filtration, washed with water (100 ml) and dried to give 44.4 g of ethyl p-hydroxybenzoate.
[2] The yield is abased on unrecovered starting material.

Analysis: Calculated for $C_{11}H_{13}ClO_3$: C, 57.78; H, 5.73. Found: C, 57.87; H, 5.82.

PREPARATION 18

1-[4-(2-Chloroethoxy)-3-methoxyphenyl]ethanone

To a solution of 12.7 g (0.55 mole) of sodium metal in 750 ml of absolute ethanol was added 83.1 g (0.5 mole) of acetovanillone to give a slurry. This slurry was then added over a 3 hr period to a solution of 107.6 g (0.75 mole) 1-bromo-2-chloroethane in 500 ml of absolute ethanol at reflux. An additional 250 ml of ethanol was used to wash the slurry into the reaction mixture. The mixture was heated at reflux overnight and then concentrated under reduced pressure to give a solid as residue. The solid was partitioned between 1 liter of benzene and 1 liter of water. The aqueous layer was extracted with 500 ml of benzene and the combined organic layers were washed successively with three 200 ml portions of a 5% sodium hydroxide solution, once with water and once with brine. The benzene solution was dried over anhydrous sodium sulfate and concentrated under reduced pressure to give an oil which gradually crystallized. The solid was triturated with petroleum ether, collected by filtration and recrystallized from 2-propanol to yield 48.5 g (42%) of off-white solid. An analytical sample was prepared from isopropyl ether, m.p. 69°–71° C.

Analysis: Calculated for $C_{11}H_{13}ClO_3$: C, 57.78; H, 5.73. Found: C, 57.55; H, 5.74.

PREPARATION 19

1-[4-(4-Bromobutoxy)-3-methoxyphenyl]ethanone

To a warm solution of 12.7 g (0.55 mole) of sodium metal in 500 ml of absolute ethanol was added a slurry of 83.1 g (0.5 mole) of acetovanillone in 250 ml of absolute ethanol. All solids dissolved and then a solid precipitated. The mixture was stirred at ambient temperature for 1 hr and then added over a 3 hr period to a solution at reflux of 177 g (0.82 mole) of 1,4-dibromobutane in 500 ml of absolute ethanol. After addition was complete, the mixture was heated at reflux overnight. The mixture was concentrated under reduced pressure and the residue was partitioned between 1.5 liter of benzene and 1 liter of water. The mixture was filtered to remove undesirable insoluble material. The filtrate layers were separated and the organic layer was washed with four 300 ml portions of a 5% sodium hydroxide solution once with water and once with brine, dried over anhydrous sodium sulfate and concentrated under reduced pressure to give 138 g of gummy solid as residue. This solid was purified by column chromatography on 1 kg of silica gel, eluting with 2% ethyl acetate in benzene to yield 69.9 g (46%) of title compound as an off-white solid. The solid was recrystallized from isopropyl ether, m.p. 52°–54° C.

Analysis: Calculated for $C_{13}H_{17}BrO_3$: C, 51.84; H, 5.69. Found: C, 52.03; H, 5.76.

PREPARATION 20

4-(Diphenylmethyl)pyridine

A mixture of 99 g (0.379 mole) of diphenyl-4-pyridylmethanol, 50 ml of conc. hydrochloric acid, 200 ml of 57% hydroiodic acid and 200 ml of glacial acetic acid was refluxed for 4½ hr and then was stirred at room temperature for 12 hr. The reaction mixture was poured over ice and was made basic with 50% sodium hydroxide. An aqueous solution of sodium thiosulfate was added, and the mixture was extracted with methylene chloride. The methylene chloride solution was dried over magnesium sulfate and the solvent was removed in vacuo. The residue was recrystallized from a mixture of methylene chloride-ether-hexane to give two crops of crystalline solids: Crop I, 40.87 g (44.0%), m.p. 124–126; Crop II, 25.38 g (27.3%), m.p. 123–125. Analysis of the mixture of the Crops I and II was as follows:

Analysis: Calculated for $C_{18}H_{15}N$: C, 88.13; H, 6.16; N, 5.71. Found: C, 87.67; H, 6.01; N, 5.56.

PREPARATION 21

1-(3-Chloropropoxy)-4-methoxybenzene

A solution of sodium hydroxide 20.0 g (0.5 mole in 300 ml of water and p-methoxyphenol, 62.1 g (0.5 mole) in 300 ml of dioxane was stirred for 1 hour at room temperature. 1-Chloro-3-bromopropane (472.35 g, 3.0 mole) in 100 ml of dioxane was added, and the reaction mixture was stirred overnight at 80° C. The lower layer was separated and the aqueous layer extracted with hexane. The lower layer and hexane layer were combined, dried, and solvent was removed in vacuo. The residue was dissolved in chloroform and extracted with 5% sodium hydroxide; removal of chloroform by evaporation gave a yellow oil. A 10 g sample of the oil was subjected to column chromatography on silica gel with an elution series composed of hexane-methylene chloride-methanol. This furnished 9.64 g (79.3% based on the aliquot taken) of pure clear oil.

Analysis: Calculated for $C_{10}H_{13}O_2Cl$: C, 59.86; H, 6.53. Found: C, 59.39; H, 6.56.

PREPARATION 22

1-[4-(3-Chloropropxy)phenyl]ethanone

The sodium salt of p-hydroxyacetophenone was prepared in 200 ml of dioxane-400 ml of water from p-hydroxyacetophenone 68.08 g (0.5 mole) and sodium hydroxide 20.0 g, (0.5 mole). The reaction mixture was stirred ¾ hr at room temperature. Next, chlorobromopropane, 472.35 g (3.0 mole) was added along with 200 ml of dioxane and the mixture was heated at 80°–90° C. overnight with stirring. The mixture was diluted to 4 liters with water; the aqueous phase was extracted with hexane and chloroform. These were combined and back extracted with 5% sodium hydroxide. The solvent was removed in vacuo with heating. A 10 g sample of the oil was subject to column chromatography on silica gel using hexane-methylene chloride-methanol. Fractions with similar TLCs were combined and solvent removed. The oil from the column did not analyze, therefore a short-path bulb-bulb distillation was carried out. This produced 4.38 g (37.9%) of clear oil.

Analysis: Calculated for $C_{11}H_{13}O_2Cl$: C, 62.12; H, 6.16. Found: C, 61.70; H, 6.17.

$^1$H NMR (CDCl$_3$) Analysis:

| | | | |
|---|---|---|---|
| σ 8.1 | doublet | aromatic portons | 2H |
| σ 6.8–7.0 | doublet | aromatic portons | 2H |
| σ 4.1–4.3 | triplet | CH$_2$ | 2H |
| σ 3.6–3.8 | triplet | —CH$_2$— | 2H |
| σ 2.5 | singlet | C—CH$_3$ or COCH$_3$ ‖ O | 2H |
| σ 2–2.4 | triplet | —CH$_2$— | 2H |

PREPARATION 23

4-(Diphenylmethyl)piperidine hydrochloride [1:1]

A mixture of 62.69 g (0.256 mole) of diphenyl-4-pyridylmethane and 6.4 g of 10% palladium on carbon (0.0060 mole) in 300 ml of glacial acetic acid and under an atmosphere of hydrogen (44 psi) was shaken on a Parr apparatus at 85° for 4 days. The reaction mixture was filtered, and the solvent was removed in vacuo from the filtrate. The residue was partitioned between methylene chloride and dilute sodium hydroxide. The methylene chloride solution was dried over magnesium sulfate, and the solvent was removed in vacuo to give a solid. This was dissolved in a mixture of methanolacetronitrile, and excess ethereal hydrogen chloride was added. A precipitated was collected to give 59.13 g (80.3%) of slightly impure title compound as a white crystalline solid, m.p. 273°–274° C. Part of this was recrystallized from methanol-ether to give an analytically pure sample, m.p. 275.5°–277° C.

Analysis: Calculated for $C_{18}H_{22}NCl$: C, 75.11; H, 7.70; N, 4.87. Found: C, 75.03; H, 7.73; N, 4.93.

PREPARATION 24

α-(4-Fluorophenyl)-α-phenyl-4-pyridinemethanol

To a suspension of 18.5 g (0.761 mole) of magnesium turnings and several crystals of iodine in 800 ml of anhydrous ether, cooled in an ice bath and under an atmosphere of argon was slowly added a solution of p-bromofluorobenzene in 200 ml of ether. The solution was stirred for 2 hr at 25° C. and 97.02 g (0.530 mole) of 4-benzoylpyridine was added as a solid. An additional 1 liter of anhydrous ether was added, and the solution was stirred at 25° C. for 3 hr. The reaction mixture was poured into an icy, aqueous solution of ammonium chloride. The mixture stood in the hood overnight and a white solid was collected. The solid was dissolved in a mixture of methanol-methylene chloride. The solution was filtered and the solvent was removed in vacuo. The residue was crystallized from chloroform-hexane to give 66.86 g (45%) of title compound as a white, crystalline solid, m.p. 189°–192° C. Part of this was recrystallized from methylene chloride-acetonitrile-hexane, m.p. 190°–192° C.

Analysis: Calculated for $C_{18}H_{14}NOF$: C, 77.40; H, 5.05; N, 5.02. Found: C, 77.24; H, 5.03; N, 4.90.

PREPARATION 25

α,α-Bis(4-chlorophenyl)-1(phenylsulfonyl)4-piperidinemethanol

Following the procedure of Preparation 7, but substituting p-bromochlorobenzene for p-bromofluorobenzene, the title compound was prepared.

PREPARATION 26

4-[Bis(4-chlorophenyl)methylene]piperidine hydrobromide hydrate [1:1:1]

A mixture of 69.33 g (0.146 mole) of α,α-bis(4-chlorophenyl)-1-(phenylsulfonyl)-4-piperidinemethanol and 26 g (0.277 mole) of phenol in 400 ml of 48% hydrobromic acid was refluxed for 6 hr and then was stirred at room temperature for 10 hr. The reaction solution was decanted from a gun which had formed in the bottom of the reaction flask. The gum was washed with several portions of water and then was crystallized from ether to give a solid. The solid was recrystallized from a mixture of methanoldiethyl ether to give 26.52 g (43.6%) of white crystalline solid, m.p. 106°–109° C.

Analysis: Calculated for $C_{18}H_{20}NBrCl_2O$: C, 51.83; H, 4.83; N, 3.36. Found: C, 52.13; H, 4.62; N, 3.38.

PREPARATION 27

1-Chloro-4-(3-chloropropoxy)benzene

A mixture of 77.2 g (0.60 mole) of p-chlorophenol, 189 g (1.2 mole) of 1-bromo-3-chloropropane, 249 g (1.8 mole) of anhydrous potassium carbonate, and 600 ml of acetone was stirred vigorously and heated to reflux for 16 hr under a nitrogen atmosphere. The potassium carbonate was removed by suction filtration, and the acetone and excess bromochloropropane were removed by heating under reduced pressure. The residue was dissolved in petroleum ether, and the resulting solution was cooled in an ice-isopropyl alcohol bath to produce a white solid. The solid was collected by filtration and washed with cold petroleum ether. The filtrate was concentrated and cooled to yield two more crops of white crystals. The combined solids were dried under vacuum at ambient temperature to yield 107 g (87%) of white, flaky solid, m.p. 35°–36° C.

Analysis: Calculated for $C_9H_{10}OCl_2$: C, 52.71; H, 4.92. Found: C, 52.99; H, 4.87.

PREPARATION 28

4-(3-Chloropropoxy)benzoic acid methyl ester

Ethyl, 4-hydroxybenzoate 83.1 g (0.50 mole), 107 ml (1.0 mole) of 1-bromo-3-chloropropane, and potassium carbonate (1.5 mole, 207.3 g) were mechanically stirred in 600 ml of refluxing acetone under nitrogen overnight. The potassium carbonate was removed by filtration, and the filtrate was evaporated under reduced pressure to give 122 g of a liquid. This liquid was dissolved in 250 ml of petroleum ether and with stirring and cooling in an ice/2-propanol bath. A white precipitate formed and was collected by filtration and washed with cold petroleum ether to yield 108 g of a solid. An additional 6 g of the product was obtained from the mother liquor. A small sample of the solid was dissolved in petroleum ether at room temperature. The solution was stirred and cooled in an ice bath. White crystals were collected by filtration, washed with cold petroleum ether and dried under vacuum at room temperature, m.p. 24°–25° C.

Analysis: Calculated for $C_{12}H_{15}O_3Cl$: C, 59.39; H, 6.23. Found: C, 59.69; H, 6.30.

PREPARATION 29

1-(3-Chloropropoxy)-4-nitrobenzene

A mixture of 7.0 g (0.05 mole) of 4-nitrophenol, 15.7 g (0.1 mole) of 1-bromo-3-chloropropane and 20.7 g (0.15 mole) of anhydrous potassium carbonate in 350 ml of acetone was heated at reflux for 17 hr. The mixture was cooled, filtered, and the filtrate was concentrated to give an oil which crystallized. The solid was collected by filtration, washed with petroleum ether, and dried to yield 10.1 g (94%) of the title compound. An analytical sample was prepared from ethyl ether-petroleum ether, m.p. 37°–39° C.

Analysis: Calculated for $C_9H_{10}ClNO_3$: C, 50.13; H, 4.67; N, 6.50. Found: C, 49.95; H, 4.71; N, 6.51.

PREPARATION 30

4-[Bis(4-fluorophenyl)methyl]-1-piperidinepropanol oxalate monohydrate

A mixture of 10.67 g (0.0372 mole) of 4-[bis(4-fluorophenyl)methyl]piperidine, 5.42 g (0.039 mole) of 3-bromo-1-propanol and 8 g (0.095 mole) of sodium bicarbonate in 400 ml of 1-butanol was refluxed for 21 hr. The solvent was removed in vacuo, and the residue was partitioned between methylene chloride and dilute sodium hydroxide. The methylene chloride solution was dried over magnesium sulfate and the solvent was removed in vacuo to give 8.88 g (67.3%) of oil, the free base of the title compound. A small sample of this oil was converted to the oxalate salt, and the salt was recrystallized from methanol-ether to give a white solid, m.p. 89°–94° C. Overall yield was calculated to be 75.1%.

Analysis: Calculated for $C_{23}H_{29}NO_6F_2$: C, 60.92; H, 6.45; N, 3.09. Found: C, 61.49; H, 6.15; N, 3.03.

PREPARATION 31

4-(3-Chloropropoxy)-3-methoxybenzoic acid methyl ester

A mixture of 100 g (0.549 mole) of methylvanillate, 172.8 g (1.1 mole) of 1-bromo-3-chloropropane and 228 g (1.65 mole) of anhydrous potassium carbonate in 1 liter of acetone was heated at reflux for 20 hr. The mixture was cooled, filtered, and the filtrate concentrated to give a white solid as residue. The solid was triturated with petroleum ether, collected by filtration, and dried to yield 137.8 g (97%) of white powder which was recrystallized from isopropyl alcohol, m.p. 104°–105° C.

Analysis: Calculated for $C_{12}H_{15}ClO_4$: C, 55.71; H, 5.84. Found: C, 55.87; H, 5.94.

PREPARATION 32

4-[Bis(4-methoxyphenyl)methyl]pyridine

Anisole, 108.13 g (1.0 mole) was cooled in an ice bath. Concentrated sulfuric acid, 115.3 ml (2.0 mole) was added while stirring the mixture in an ice bath. The temperature rose to 55° C. The reaction was then cooled in the ice bath. To this solution was added 4-pyridine carboxaldehyde, 53.5 g (0.5 mole). The temperature rose to 95° C. and further cooling and stirring brought the temperature down to 20° C. The reaction mixture was heated to 70° C. for 3½ hr. The red gel was made alkaline with 50% sodium hydroxide-ice mix. The alkaline phase was extracted with toluene and the toluene extracted with a saturated sodium chloride solution. The product crystallized from the toluene solution while standing at room temperature. The white solid can be recrystallized from hot hexane-isopropyl alcohol.

A small 2.2 g sample of the product was recrystallized from methylene chloride-hexanes (1:9 v/v) and dried overnight at 80° C. in vacuo. This furnished 1.08 g (48.6% yield based on the aliquot taken) of white crystalline product in 49% yield, m.p. 111.5°–113.5° C.

Analysis: Calculated for $C_{20}H_{19}NO_2$: C, 78.66; H, 6.27; N, 4.59. Found: C, 78.41; H, 6.24; N, 4.54.

PREPARATION 33

4-[Bis(4-methoxyphenyl)methyl]piperidine hydrochloride hydrate [1:1:1]

The precursor pyridine derivative 4-[bis-4-methoxyphenyl)methyl]pyridine was prepared from the reaction of anisole and 4-pyridine carboxaldehyde in the presence of sulfuric acid.

To prepare the title compound, a solution of 4-[bis-4-methoxyphenyl)methyl]pyridine (70.8 g, 0.232 mole) in 350 ml of acetic acid was hydrogenated with 5% palladium on carbon (7.08 g) for five hours with heat. The hydrogenation was continued overnight at room temperature. The reaction mixture was filtered and rinsed with methanol. The filtrate was stripped of solvent via a rotary evaporator and the residue was partitioned between 5% sodium hydroxide and toluene. The aqueous layer was back extracted with toluene. The organic layer was dried over anhydrous sodium sulfate and filtered. Removal of solent by means of a rotary evaporator gave 64 g (88.6%) of white solid, the free base. The free base was then converted to the hydrochloride salt by dissolving it in methanol and treating with ethereal hydrogen chloride. The white solid was filtered off and dried overnight at 80° C. in vacuo in the amount of 2.08 g (69.3%), m.p. 132°–135° C.

Analysis: Calculated for $C_{20}H_{28}NO_3Cl$: C, 65.65; H, 7.71; N, 3.83. Found: C, 65.63; H, 7.53; N, 3.90.

PREPARATION 34

4-[Bis(4-methylphenyl)methyl]piperidine hydrochloride [1:1]

The free base of the title compound was prepared by hydrogenation of 4-[(bis-4-methylphenyl)methyl]pyridine in acetic acid using palladium on carbon as catalyst and converted to the hydrochloride salt in methanol-diethyl ether. The salt was recrystallized from methanol-diethyl ether and isopropanol-diethyl ether and dried overnight in vacuo at 80° C. White solid amounting to 46% yield, m.p. 232° C. was obtained.

Analysis: Calculated for $C_{20}H_{26}NCl$: C, 76.05; H, 8.30; N, 4.43. Found: C, 75.51; H, 8.33; N, 4.33.

PREPARATION 35

N-[4-(3-Chloropropoxy)phenyl]acetamide

A mixture of 4-acetamidophenol, 182.2 g (1.2 mole), bromochloropropane, 157.4 g (1.0 mole), and potassium carbonate, 145.0 g (1.05 mole) was refluxed overnight in 700 ml of acetone. The acetone solution was refrigerated overnight and white crystals formed. This white solid was filtered and washed with acetone. The filtrate was stripped to dryness and the residue was dissolved in chloroform and extracted with 5% sodium hydroxide. Removal of chloroform gave an oil. The white solid was also dissolved in chloroform and extracted with 5% sodium hydroxide. Removal of chloroform gave a white solid. The white solid and oil were combined and placed in acetone in the refrigerator; white crystals were obtained. The white crystals were recrystallized twice from acetone. A 5 g sample of the white crystals was recrystallized from acetone. This furnished 1.76 g (after drying in vacuo overnight at 80° C.) (23%) of white crystalline product; m.p. 125°–127° C.

Analysis: Calculated for $C_{11}H_{14}NO_{27}Cl$: C, 58.03; H, 6.20; N, 6.15. Found: C, 58.21; H, 6.28; N, 6.15.

PREPARATION 36

1-(3-Chloropropoxy)-3,5-dimethoxybenzene

A mixture of 3,5-dimethoxyphenol, 100.0 g (0.6486 mole), chlorobromopropane, 148.0 g (0.96 mole) and potassium carbonate, 89.6 g (0.96 mole) was heated overnight at gentle reflux in 600 ml of acetone. The reaction mixture was cooled at room temperature, filtered, and stripped to dryness via a rotary evaporator. The resulting oil was dissolved in chloroform and the solution extracted with 5% aqueous sodium hydroxide; removal of chloroform gave a dark brown oil. A 5 g sample of the oil was pumped in vacuo overnight at 80° C. This produced 3.23 g (53.2% yield based on the aliquot taken) of dark brown oil.

H' (CDCl$_3$): σ2–2.4 (quintuplet, center methylene protons, 2H), 3.6–4.2 (m, aliphatic protons, 4H), 3.8 (s, OCH$_3$, 6H), 6.1 (s, aromatic protons, 3H).

Analysis: Calculated for $C_{11}H_{15}O_3Cl$: C, 57.27; H, 6.56. Found: C, 56.96; H, 6.49.

PREPARATION 37

4-(3-Chloropropoxy)benzonitrile

A mixture of 4-cyanophenol, 125.0 g (1.05 mole), bromochloropropane, 189.0 g (1.2 mole) and potassium carbonate, 145.0 g (1.05 mole) was heated overnight at reflux in 750 ml of acetone. The reaction mixture was filtered and stripped to dryness. The resulting residue was dissolved in chloroform and extracted with 5% sodium hydroxide. Removal of chloroform gave an oil which crystallized to a white solid. A 5 g sample was recrystallized from isopropyl ether. This furnished 1.22 g (24.4%) of white solid, m.p. 40°–44° C. which contained a dimer impurity.

Analysis: Calculated for $C_{10}H_{20}NOCl$: C, 61.39; H, 5.15; N, 7.16. Found: C, 61.57; H, 5.14; N, 7.20.

PREPARATION 38

1-[4-(3-Chloropropoxy)-3-methylphenyl]ethanone

A mixture of 25 g (0.166 mole) of 4-hydroxy-3-methylacetophenone, 45.8 g (0.33 mole) of 1-bromo-3-chloropropane and 69.1 g (0.5 mole) of anhydrous potassium carbonate in 500 ml of acetone was heated at reflux for 20 hr. The mixture was cooled, filtered, and the filtrate concentrated under reduced pressure to give an oil as residue. The oil was crystallized in petroluem ether. The solid was collected by filtration, washed with petroleum ether and dried to yield 35.8 g (95%) of an off-white powder. An analytical sample, m.p. 41.5°–42.5° C. was prepared from petroleum ether.

Analysis: Calculated for $C_{12}H_{15}ClO_2$: C, 63.58; H, 6.67. Found: C, 63.40; H, 6.64.

PREPARATION 39

4-(3-Chloropropoxy)benzamide

A mixture of 50 g (0.365 mole) of 4-hydroxybenzamide, 114.8 g (0.729 mole) of 1-bromo-3-chloropropane and 151.3 g (1.1 mole) of anhydrous potassium carbonate in 1 liter of acetone was heated at reflux for 20 hr. The mixture was concentrated under reduced pressure and the residue was stirred with 1.2 liter of water to remove inorganic solids. The mixture was filtered and te filter cake was washed with water and petroleum ether and dried to yield 75.5 g (97%) of white solid. The solid was recrystallized from ethylacetate, m.p. 142°–143° C.

Analysis: Calculated for $C_{10}H_{12}ClNO_2$: C, 56.22; H, 5.66; N, 6.56. Found: C, 55.92; H, 5.61; N, 6.56.

PREPARATION 40

1-[4-(5-Chloropentoxy)-3-methoxyphenyl]ethanone

A mixture of 59.7 g (0.36 mole) of acetovanillone, 100 g (0.539 mole) of 1-bromo-5-chloropentane and 138 g (1 mole) of anhydrous potassium carbonate in 1 liter of acetone was heated at reflux for 20 hr. The mixture was filtered and the filtrate was concentrated under reduced pressure to give an oil which crystallized in petroleum ether (30°–60° C.). The solid was collected by filtration, washed with petroleum ether and dried to yield 81.4 g (84%) of fluffy, white solid. The solid was recrystallized from isopropyl ether, m.p. 57°–58° C.

Analysis: Calculated for $C_{14}H_{19}ClO_3$: C, 62.11; H, 7.07. Found: C, 62.14; H, 7.10.

PREPARATION 41

4-(3-Chloropropoxy)-3-methoxybenzeneacetic acid ethyl ester

A mixture of 50 g (0.238 mole) of ethyl homovanillate, 75 g (0.476 mole) of 1-bromo-3-chloropropane and 98.7 g (0.71 mole) of anhydrous potassium carbonate in 1 liter of acetone was heated at reflux for 24 hr. The mixture was filtered and the filtrate was concentrated under reduced pressure to give an oil which gradually crystallized to a semi-solid. The solid was recrystallized from ethyl ether-petroleum ether (30°–60° C.) to yield 44.4 g (65%) of white solid, m.p. 36°–38° C.

Analysis: Calculated for $C_{14}H_{19}ClO_4$: C, 58.64; H, 6.68. Found: C, 58.74; H, 6.74.

PREPARATION 42

1-(3-Chloropropoxy)-4-(methylsulfonyl)benzene

To a solution of 21.7 g (0.1 mole) of 1-(3-chloropropoxy)-4-(methylthio)benzene in 100 ml of chloroform was cautiously added a slurry of 51.8 g (0.3 mole) of m-chloroperbenzoic acid in 450 ml of chloroform. The mixture was stirred at ambient temperature for 2 days and then filtered. The filtrate was washed with four portions of a solution comprised of 110 ml of saturated sodium bicarbonate, 110 ml of water, and 30 ml of 20% sodium hydroxide, once with brine, dried (sodium sulfate) and concentrated under reduced pressure to give a solid as residue. The solid was triturated with petroleum ether, collected by filtration and air dried to yield 24.3 g (98%) of white solid. An analytical sample, m.p. 84°–86° C. was recrystallized from 2-propanol.

Analysis: Calculated for $C_{10}H_{13}ClO_3S$: C, 48.29; H, 5.27. Found: C, 48.38; H, 5.30.

PREPARATION 43

5-Oxo-1-(phenylmethyl)-3-pyrrolidinecarboxylic acid, methyl ester

A solution of 158.2 g (1.0 mole) of dimethylitaconate and 107.2 g (1.0 mole) of benzylamine in 750 ml of methanol was let stand at ambient temperature over the weekend. The solutin was filtered and the filtrate was concentrated under reduced pressure to give an oil as residue. The oil crystallized when it was triturated with petroleum ether (30°–60° C.). The solid was collected by filtration and dried to yield 225.5 g (97%) of white powder. An analytical sample, m.p. 63°–65° C. was prepared from diisopropyl ether.

Analysis: Calculated for $C_{13}H_{15}NO_3$: C, 66.94; H, 6.48; N, 6.01. Found: C, 66.82; H, 6.48; N, 6.01.

PREPARATION 44

1-Benzyl-3-hydroxymethyl-pyrrolidine oxalate [1:1]

A solution of (60.0 g, 0.2553 mole) 5-oxo-1-(phenylmethyl)-3-pyrrolidinecarboxylic acid methyl ester in dry dimethoxyethane was added to a mixture of dimethoxyethane and 47.0 g (1.23 mole) of lithium aluminum hydride. The reaction mixture was stirred 2 hrs at room temperature and then heated at reflux 2 hrs. The mixture was then stirred overnight at room temperature, then quenched by the slow addition of ethyl acetate. More ethyl acetate was added and the use of celite allowed the solid material to be separated from filtrate by filtration. The filtrate was stripped to dryness and dissolved in chloroform. The chloroform layer was extracted with 10% sodium hydroxide. The chloroform layer was dried, filtered, and solvent removed to give an oil. A portion of the oil was converted to the oxalate salt. The salt was recrystallized from methanol-diethyl ether and dried at 80° C. in vacuo overnight to give 2.27 g, 39.4% yield of white crystalline solid, m.p. 98°–102° C.

Analysis: Calculated for $C_{14}H_{19}NO_5$: C, 59.78; H, 6.81; N, 4.98. Found: C, 59.43; H, 6.79; N, 4.95.

PREPARATION 45

1-[4-(6-Chlorohexyloxy)-3-methoxyphenyl]ethanone

A mixture of 41.6 g (0.25 mole) of acetylvanillone, 76 g (0.375 mole) of 1-bromo-6-chlorohexane and 103.7 g (0.75 mole) of anhydrous potassium carbonate in 750 ml of acetone was heated at reflux 20 hr. The mixture was cooled, filtered, and the filter cake washed with acetone. The combined filtrates were concentrated under vacuum pump pressure at 90° C. to give an oil which gradually crystallized. The residue was triturated with petroleum ether (30°–60° C.), collected by filtration, and dried to yield 59.6 g (84%) of off-white solid. An analytical sample, m.p. 35°–38° C., was prepared from isopropyl ether.

Analysis: Calculated for $C_{15}H_{21}ClO_3$: C, 63.26; H, 7.43. Found: C, 63.50; H, 7.60.

PREPARATION 46

4-(3-Chloropropoxy)benzenesulfonamide

A mixture of 25 g (0.144 mole) of p-hydroxybenzenesulfonamide, 45.5 g (0.289 mole) of 1-bromo-3-chloropropane and 59.7 g (0.432 mole) of anhydrous potassium carbonate in 500 ml of acetone was heated at reflux for 24 hr. The mixture was cooled, filtered and the filtrate concentrated under vacuum pump pressure at 90° C. to give 32.2 g of tan gum as residue. The gum was purified by column chromatography on 600 g of silica gel. Fractions containing the title compound eluted with 8% acetone in benzene were combined and concentrated under reduced pressure to yield 12.2 g (34%) of white solid, m.p. 106–107.5 on recrystallization from 2-propanol.

Analysis: Calculated for $C_9H_{12}NO_3S$: C, 43.29; H, 4.84; N, 5.61. Found: C, 43.48; H, 4.92; N, 5.62.

PREPARATION 47

7-(3-Chloropropoxy)-2H-1-benzopyran-2-one

A mixture of 16.8 g (0.104 mole) of 7-hydroxycoumarin, 31.6 g (0.2 mole) of 1-bromo-3-chloropropane and 41.5 g (0.3 mole) of anhydrous potassium carbonate in 500 ml of acetone was heated at reflux for 24 hr. The mixture was filtered with difficulty to give a milky filtrate. The filtrate was treated wich charcoal and filtered through celite to give a clear filtrate. The filtrate was concentrated under reduced pressure to give a solid residue. The solid was triturated with petroleum ether (30°–60° C.), collected by filtration, and dried to yield 19.1 g (77%) of fluffy, white solid. An analytical sample, m.p. 100°–102° C., was obtained on recrystallization from 2-propanol.

Analysis: Calculated for $C_{12}H_{11}ClO_3$: C, 60.39; H, 4.65. Found: C, 60.35; H, 4.68.

PREPARATION 48

7-(3-Chloropropoxy)-4-oxo-4H-1-benzopyran-2-carboxylic acid ethyl ester

A mixture of 23.4 g (0.1 mole) of 7-hydroxy-4-oxo-4H-1-benzopyran-2-carboxylic acid ethyl ester, 31.6 g (0.2 mole) of 1-bromo-3-chloropropane and 41.5 g (0.3 mole) of anhydrous potassium carbonate in 500 ml of acetone was heated at reflux for 20 hr. The mixture was cooled and filtered through Celite. The filtrate was concentrated under reduced pressure to give a solid residue. The solid was triturated with petroleum ether (30°–60° C.), collected by filtration, and recrystallized from 2-propanol to yield 22.5 g (73%) of white solid, m.p. 107°–108° C.

Analysis: Calculated for $C_{15}H_{15}ClO_5$: C, 57.98; H, 4.87. Found: C, 58.21; H, 4.88.

PREPARATION 49

1-[4-(3-Chloropropoxy)-2-methoxyphenyl]ethanone

A mixture of 10.6 g (0.637 mole) of 1-(4-hydroxy-2-methoxyphenyl)ethanone, 20 g (0.127 mole) of 1-bromo-3-chloropropane and 26.4 g (0.19 mole) of anhydrous potassium carbonate in 250 ml of acetone was heated at reflux for 20 hr. The mixture was cooled, filtered and the filtrate concentrated under vacuum pump pressure at 90° C. to give an oil which gradually crystallized. The solid was triturated with petroleum ether (30°–60° C.), collected by filtration and dried to yield 14.6 g (94%) of white solid, m.p. 47°–49° C. on recrystallizing from isopropyl ether.

Analysis: Calculated for $C_{12}H_{15}ClO_3$: C, 59.39; H, 6.23. Found: C, 59.32; H, 6.26.

PREPARATION 50

1-(3-Chloropropoxy)-4-sulfinylbenzene

The title compound is prepared by treating 1-(3-chloropropoxy)-4-methylthiobenzene with sodium perborate in glacial acetic acid.

PREPARATION 51

2-(3-Chloropropoxy)benzonitrile

A mixture of 2-cyanophenol (50.0 g, 0.42 mole), 1-bromo-3-chloropropane (67.7 g, 0.43 mole), and potassium carbonate (58.0 g, 0.42 mole) was heated overnight at gentle reflux in 500 ml of acetone. The reaction mixture was stripped to dryness and the residue was dissolved in chloroform. The chloroform layer was extracted several times with 5% sodium hydroxide. The chloroform layer was dried (anhydrous sodium sulfate), filtered, and the solvent was removed, to give a brown oil (80.09 g). A ten gram portion of this oil was subjected to flash chromatography on silica gel with 10% ethyl acetate-hexanes and 20% ethyl acetate-hexanes used for elution. Fractions were combined and solvent removed in vacuo. The clear oil obtained was dried 18 hrs in vacuo at room temperature and 8 hrs at 80° C. in vacuo. This furnished 5.24 g (50.0% yield—based on aliquot taken) of clear oil.

$^1$H NMR (CDCl$_3$): δ 2.1–2.5 (q, 2, —CH$_2$), 3.8 (t, 2, —ClCH$_2$), 4.2 (t, 2, —OCH$_2$), 6.9 (m, 2, aromatic protons ortho and para to ether), 7.5 (m, 2, aromatic protons ortho and para to CN group).

Analysis: Calculated for $C_{10}H_{10}NOCl$: C, 61.39; H, 5.15; N, 7.16. Found: C, 61.27; H, 5.15; N, 7.14.

PREPARATION 52

1-Phenylmethyl-3-pyrrolidinemethanol methanesulfonate (ester) oxalate [1:1]

A solution of 113.80 g (0.596 mole) of 1-benzyl-3-hydroxymethylpyrrolidine and triethylamine, 66.6 g (0.66 mole) in 600 ml of acetonitrile was prepared. This solution was cooled in an ice bath. A solution of tosyl chloride, 125.9 g (0.66 mole) in 300 ml of acetonitrile was added dropwise with stirring. The solution was allowed to stir overnight at room temperature. A solid precipitated and the solution was filtered. The solvent was removed by rotary evaporator and the residue was dissolved in chloroform. The chloroform layer was extracted with 5% sodium hydroxide and water. The chloroform layer was dried (anhydrous sodium sulfate), filtered, and solvent removed to give 232.9 g of a dark brown oil. This oil was converted to the oxalate salt and recrystallized from methanol-diethyl ether. After drying at 80° C. in vacuo overnight, 181.63 g of white crystalline solid was obtained. A five gram sample was recrystallized again from methanol-diethyl ether and dried at 80° C. in vacuo overnight. A yield of 1.41 g (19.7% overall adjusted for the aliquot taken) of white crystalline solid, m.p. 147°–149° C. was obtained.

Analysis: Calculated for $C_{21}H_{25}NO_7S$: C, 57.92; H, 5.79; N, 3.22. Found: C, 57.62; H, 5.82; N, 3.22.

PREPARATION 53

N-[3-(3-Chloropropoxy)phenyl]urea

A mixture of 45.6 g (0.3 mole) of 1-(3-hydroxyphenyl)urea, 94.5 g (0.6 mole) of 1-bromo-3-chloropropane, 124.4 g (0.9 mole) of anhydrous potassium carbonate and 1 liter of acetone was heated at reflux with mechanical stirring for 20 hr. The mixture was concentrated and the residue was slurried with 1.5 liters of water. The mixture was filtered and the filter cake was recrystallized from isopropanol to yield 57.0 g (83%) of off-white solid, m.p. 141°–143° C.

Analysis: Calculated for $C_{10}H_{13}ClN_2O_2$: C, 52.52; H, 5.73; N, 12.25. Found: C, 52.37; H, 5.79; N, 12.17.

PREPARATION 54

N-[4-(3-Chloropropoxy)phenyl]carbamic acid ethyl ester

A mixture of 6.6 g (0.036 mole) of (4-hydroxyphenyl)carbamic acid ethyl ester, 11.5 g (0.072 mole) of 1-bromo-3-chloropropane, 13.8 g (0.10 mole) of anhydrous potassium carbonate and 150 ml of acetone was heated at reflux for 21 hr. The mixture was cooled and filtered. The filtrate was concentrated under reduced pressure to give a solid residue. The solid was triturated with petroleum ether (30°–60° C.) collected by filtration and recrystallized from isopropanol to yield 7.7 g (83%) of white solid, m.p., 91°–93° C.

Analysis: Calculated for $C_{12}H_{16}ClNO_3$: C, 55.93; H, 6.26; N, 5.43. Found: C, 55.93; H, 6.28; N, 5.46.

PREPARATION 55

α-(4-Fluorophenyl)-2-pyridineacetonitrile

A sample of sodium hydride (60%, 1.60 g, 0.04 mole) was washed with dry hexanes. After removal of hexanes a 100 ml portion of dimethyl sulfoxide was added. To this mixture was added a solution of 4-fluorophenylacetonitrile (5.41 g, 0.04 mole). The mixture was stirred 3 hrs at room temperature under nitrogen. 2-Bromopyridine (6.32 g, 0.04 mole) was added to the mixture, the reaction mixture was then stirred overnight at 65° C. The reaction mixture was poured into 1200 ml of water and the aqueous phase was extracted several times with chloroform (the chloroform layer was filtered using Celite). The combined chloroform layer was extracted with water and 5% sodium hydroxide. The chloroform layer was dried over sodium sulfate, filtered, and solvent removed to give a red oil. The oil was subjected to flash chromatography on silica gel using 10% ethylacetate-90% hexanes and 20% ethylacetate-80% hexanes for elution. Fractions of similar purity was combined and solvent removed in vacuo. The oil obtained was dried in vacuo overnight at 80° C. to give 2.43 g (28.6%) of clear oil.

$^1$H (CDCl$_3$): δ 8.5 (m, 1, proton adjacent to N in pyridine nucleus), 6.8–7.8 (m, 7, aromatics), 5.3 (S, 1, methine).

Analysis: Calculated for $C_{13}H_9N_2F$: C, 73.57; H, 4.27; N, 13.20. Found: C, 72.23; H, 4.23; N, 13.12.

PREPARATION 56

α-(4-Fluorophenyl)-α-[1-[(4-methylphenyl)sulfonyl]-4-piperidinyl]-2-pyridineacetonitrile hemihydrate The sodium salt of the free base of α-(4-fluorophenyl)-2-pyridineacetonitrile was formed in dimethylsulfoxide from sodium hydride (60%, 5.16 g, 0.129 mole) and the free base of α-(4-fluorophenyl)-2-pyridineacetonitrile (27.36 g, 0.129 mole). The salt was stirred in dimethylsulfoxide for 4½ hr at room temperature. Next, 4-methylphenylsulfonic acid ester with 1-[(4-methylbenzene)sulfonyl]-4-piperidinol (52.8 g, 0.129 mole) was added and the reaction mixture was stirred 2 hr at room temperature. The reaction mixture was stirred overnight at 80° C. The solvent was removed in vacuo and the residue obtained was dissolved in chloroform. The chloroform was extracted with water and 5% sodium hydroxide. The chloroform layer was dried over sodium sulfate and filtered. Solvent was removed to give a dark brown residue. This material was triturated with acetone to give 36.2 g of white solid. A one gram portion was triturated with acetone and then recrystallized from methylene chloride-acetone. The solids were dried in vacuo overnight at 80° C. to give 0.74 g (62.4% based on aliquot taken) of white crystals, m.p. 228°–229° C.

Analysis: Calculated for $C_{25}H_{25}N_3O_{2.5}SF$: C, 65.42, H, 5.49; N, 9.16. Found: C, 65.86; H, 5.27; N, 9.16.

PREPARATION 57

α-(4-Fluorophenyl)-α-(4-piperidinyl)-2-pyridineacetonitrile oxalate [2:3]

A solution of α-(4-fluorophenyl)-α-[1-[(4-methylphenyl)sulfonyl]-4-piperidinyl]-2-pyridineacetonitrile (30.86 g, 0.0687 mole) and phenol (75 g, 0.8 mole) in 200 ml of 48% hydrobromic acid was heated at reflux for 3 hrs. The resultant was cooled in ice and made alkaline with ice-50% sodium hydroxide. The aqueous layer was extracted with chloroform and the chloroform layer was extracted with 5% sodium hydroxide. The chloroform layer was dried over sodium sulfate, filtered, and solvent removed to give a dark brown oil. The entire oil was converted to the oxalate salt in methanol-diethyl ether. A one gram portion was taken and recrystallized from methanol-diethyl ether and dried in vacuo at 80° C. overnight. This furnished 0.90 g (80.2% based on aliquot taken) of white crystalline, m.p. 98° C. (soften, 70° C.).

Analysis: Calculated for $C_{21}H_{21}N_3O_6F$: C, 58.60; H, 4.92; N, 9.76. Found: C, 58.77; H, 5.01 N, 10.04.

PREPARATION 58

4-Fluoro-α-(4-fluorophenyl)benzeneacetonitrile

4-Fluorophenylacetonitrile (70.0 g, 62.2 ml, d=1.126, 0.518 mole) was heated to 120° C. Bromine (83.0 g, 26.6 ml, d=3.119, 0.525 mole) was added dropwise over 1 hr while maintaining a temperature of 120° C. The solution was stirred for ½ hr at 120° C. and then flushed vigorously with nitrogen for ¾ hr (solution A).

In a separate 2-liter flask was placed aluminum chloride (85.0 g, 0.644 mole). Fluorobenzene (200 g, 2.08 mole, d=1.024, 195.3 ml) was added dropwise with stirring over ½ hr while flushing with nitrogen (Mixture B).

Solution A was added dropwise to mixture B starting at room temperature. The temperature rose to 50° C. The reaction mixture was stirred at this temperature for ⅓ hr. The temperature was raised to 70° C. and maintained there for ⅓ hr. At this point the reaction became uncontrollable and part of the mixture was lost. The remainder was added to ice/75 ml of concentrated hydrochloric acid. The aqueous phase was extracted several times with chloroform. The solvent layer was dried, filtered, and solvent removed to give a green solid. The solid was recrystallized from isopropanol; the solid was washed with cold isopropanol twice and dried in vacuo at 55° C. overnight. This produced 29.72 g (25.1%) of light yellow solid, m.p. 62°–63.5° C.

Analysis: Calculated for $C_{14}H_9NF_2$: C, 73.36; H, 3.96; N, 6.11. Found: C, 73.55; H, 3.88; N, 6.10.

PREPARATION 59

1-[(4-Methylphenyl)sulfonyl]-α,α-diphenyl-3-piperidinepropanenitrile

The sodium salt of diphenylacetonitrile was formed in 400 ml of dimethylsulfoxide from sodium hydride (60%, 39.0 g, 0.975 mole) and diphenylacetonitrile (188.90 g, 0.975 mole). The resulting solution was stirred under nitrogen for 1 hr at room temperature. A 90–10 mixture of 3-(chloromethyl)-1-[(4-methylphenyl)sulfonyl]piperidine and 4-methylbenzenesulfonic acid 1-[(4-methylphenyl)sulfonyl]piperidin-3-yl methyl ester (221.42 g, 0.975 mole) dissolved in 400 ml of dimethylsulfoxide was added. The reaction mixture was heated to 85° C. and stirred overnight at 73° C. The dimethylsulfoxide was removed in vacuo, and the residue obtained was dissolved in chloroform. The chloroform layer was extracted with 1N sulfuric acid. The chloroform layer was dried, filtered, and the chloroform was removed by rotary evaporator. A brown residue was obtained which was triturated with isopropyl ether to give a brown solid. A 5 g sample was recrystallized from ethyl acetate-isopropyl ether. This gave 4 g (56.8% based on aliquot taken) of white solid, m.p. 136.5°–137° C.

Analysis: Calculated for $C_{27}H_{28}N_2O_2S$: C, 72.94; H, 6.35; N, 6.30. Found: C, 72.82; H, 6.36; N, 6.28.

PREPARATION 60

α,α-Diphenyl-3-piperidinepropanenitrile fumarate [1:1]

A mixture of 1-[(4-methylphenyl)sulfonyl]-α,α-diphenyl-3-piperidinepropanenitrile (302.41 g, 0.68 mole), hydrogen bromide (48%, 750 ml), and phenol (260 g, 2.76 mole) was stirred vigorously while heating at reflux for 3½ hr. The reaction mixture was cooled to room temperature and made alkaline with 50% hydroxide-ice. The aqueous phase was extracted several times with chloroform, and the chloroform layer was back extracted with 5% sodium hydroxide. The chloroform layer was dried, filtered, and solvent removed. NMR showed about 80% product was obtained. The same sequence was repeated. The chloroform layer gave a brown oil which was converted to the oxalate salt. A portion of this oxalate salt was converted to the free base which converted to the fumarate salt. This salt was recrystallized from methanol-diethyl ether and dried in vacuo at 80° C. overnight to give 6.53 g (91.1%) of white crystals, m.p. 181°–182° C.

Analysis: Calculated for $C_{24}H_{26}N_2O_4$: C, 70.92; H, 6.45; N, 6.89. Found: C, 70.46; H, 6.41; N, 6.96.

PREPARATION 61

3-(8-Quinolinyloxy)-1-propanol

A solution of 8-hydroxyquinoline (36.0 g, 0.25 mole) and potassium tert-butoxide (28.0 g, 0.25 mole) in 80 ml of dimethyl sulfoxide was stirred for 1 hr at room temperature. 3-Chloro-1-propanol (24.0 g, 0.25 mole) was added and the solution was heated overnight at 70° C. The solution was poured into 500 ml of water. A brown solid/mass was obtained. The solid was washed with several portions of water and then triturated with acetone. The solid was filtered and dried in vacuo at 80° C. overnight to give 35.67 g (70.3%) of light brown solid, m.p. 126°–127° C.

Analysis: Calculated for $C_{12}H_{13}NO_2$: C, 70.92; H, 6.45; N, 6.89. Found: C, 70.94; H, 6.49; N, 6.87.

PREPARATION 62

8-(3-Chloropropoxy)quinoline

A solution of 3-(8-quinolinyloxy)-1-propanol (32.0 g, 0.158 mole) and thionyl chloride (24.0 g, 0.203 mole) was heated at reflux for 5 hours in 300 ml of dry benzene (dried over 4 A molecular sieves). The reaction mixture was cooled to room temperature and then stripped to dryness. The residue was treated with potassium carbonate solution (30 g in 500 ml of water). The gummy residue was dissolved in chloroform and extracted with the potassium carbonate solution. The chloroform layer was dried over anhydrous sodium sulfate, filtered, and solvent removed to give a dark mass which crystallized. The mass was treated with 500 ml of boiling hexane. The hexane layer was decanted off from insoluble oil. A white solid crystallized on cooling, the hexane layer was filtered off. The solid was dried in vacuo at room temperature overnight to give 26.69 g (76.2%) of white cyrstalline solid, m.p. 69°–71° C.

Analysis: Calculated for $C_{12}H_{12}NOCl$: C, 65.02; H, 5.45; N, 6.32. Found: C, 65.19; H, 5.51; N, 6.27.

PREPARATION 63

4-Methylphenylsulfonic acid ester with 1-[(4-methylbenzene)sulfonyl]-4-piperidinol A solution of 1.63 g (0.0161 mole) of 4-hydroxypiperidine and 13.91 g (0.0732 mole) of tosyl chloride in 80 ml of pyridine was stirred at 25° C. overnight. The mixture was quenched in 200 ml of water and the aqueous mixture was extracted with several portions of methylene chloride. The methylene chloride solution was extracted with several portions of 1M sulfuric acid and 1M sodium hydroxide and then was dried over magnesium sulfate. The solvent was removed in vacuo to give a solid. This was recrystallized from methylene chloride-diethyl ether to give 4.82 g (73.3%) of the product, m.p. 140.5°–141° C.

Analysis: Calculated for $C_{19}H_{23}NO_5S_2$: C, 55.73; H, 5.66; N, 3.42. Found: C, 55.60; H, 5.64; N, 3.39.

PREPARATION 64

7-Hydroxy-4-oxo-4H-1-benzopyran-2-carboxylic acid ethyl ester

To a warm, stirred solution of 18.4 g (0.8 mole) of sodium metal in 250 ml of absolute ethanol was added dropwise a solution of 30.4 g (0.2 mole) of 2,4-dihydroxyacetophenone and 58.5 g (0.4 mole) of diethyloxalate in 50 ml of absolute ethanol and 50 ml of absolute ethyl ether over a 30 min period. The mixture was heated at reflux for 4 hr and then poured into a solution of 200 ml of concentrated hydrochloric acid and 1.8 liter of water. The mixture was extracted with two 500 ml portions of ethyl ether and the combined extracts were concentrated under reduced pressure to give a solid residue.

The solid was dissolved in a mixture of 250 ml of ethanol and 3 ml of concentrated hydrochloric acid and heated at reflux for 2 hr. The mixture was concentrated under reduced pressure and the solid residue was triturated with ethyl ether, collected by filtration, and recrystallized from 95% ethanol to yield 28.1 g (60%) of tan powder, m.p. 217°–221° C.

Analysis: Calculated for $C_{12}H_{10}O_5$: C, 61.54; H, 4.30. Found: C, 61.68; H, 4.34.

EXAMPLE 1

4-(Diphenylmethylene)-1-(3-phenoxypropyl)piperidine oxalate [1:1]

A mixture of 3.3 g (0.013 mole) of 4-diphenylmethylenepiperidine, 3.3 g (0.015 mole) of (3-bromopropoxy)benzene and 5.3 g (0.05 mole) of anhydrous sodium carbonate in 100 ml of 1-butanol was heated at reflux for 20 hr. The mixture was concentrated under reduced pressure and the residue was partitioned between water and benzene. The benzene layer was washed with water and brine, dried over anhydrous sodium sulfate and concentrated under reduced pressure to give an oil as residue, the free base of the title compound. The free base was converted to the oxalic acid salt and the solid was recrystallized from absolute ethanol to yield 4.3 g (70%) of the title product as a white powder, m.p. 175°–178° C.

Analysis: Calculated for $C_{29}H_{31}NO_5$: C, 73.55; H, 6.60; N, 2.96. Found: C, 73.59; H, 6.64; N, 2.83.

EXAMPLE 2

α,α-Bis-(4-fluorophenyl)-1-(3-phenoxypropyl)-4-piperidinemethanol oxalate hydrate [1:1:0.5]

A mixture of 3.37 g (0.011 mole) of [α,α-bis(p-fluorophenyl)]-4-piperidinemethanol, 2.52 g (0.011 mole) of (3-bromopropoxy)benzene and sodium bicarbonate (0.92 g, 0.011 mole) in 200 ml of 1-butanol was heated overnight to reflux. The butanol was removed by the rotary evaporator, and the residue partitioned between chloroform and water. Removal of the chloroform in vacuo gave a dark brown oil, the free base of the title compound. The base was converted to the oxalate salt and recrystallized from methanol-diethyl ether to give 1.41 g (23.9%) of white solid, m.p. 153° C.

Analysis: Calculated for $C_{29}H_{32}NO_{6.5}F_2$: C, 64.92; H, 6.01; N, 2.61. Found: C, 65.27; H, 5.87; N, 2.61.

EXAMPLE 3

4-[Bis(4-fluorophenyl)methylene]-1-(3-phenoxypropyl)piperidine oxalate [1:1]

A solution of 7.37 g (0.0168 mole) α,α-bis(4-fluorophenyl)-1-(3-phenoxypropyl)-4-piperidinemethanol in 100 ml of methanol containing 100 ml of 6N hydrochloric acid was gently refluxed for 4 hr. The reaction mixture was cooled, made alkaline with ice/50% sodium hydroxide, and diluted to 1 liter with water. The aqueous phase was extracted with chloroform, and removal of chloroform gave an oil. The oil was converted to the oxalate salt and recrystallized from methanol-diethyl ether to give 3.45 g (40.3%) of white solid, m.p. 190°–192° C.

Analysis: Calculated for $C_{29}H_{29}NO_5F_2$: C, 68.36; H, 5.74; N, 2.75. Found: C, 68.43; H, 5.75; N, 2.69.

EXAMPLE 4

α,α-Bis(4-fluorophenyl)-1-(3-phenoxypropyl)-4-piperidinemethanol oxalate [1:1]

To a mixture of 5.10 g (0.21 mole) of magnesium turnings and a crystal of iodine in 800 ml of dry tetrahydrofuran (distilled from lithium aluminum hydride) was added a solution of 36.75 g (0.21 mole) of p-bromofluorobenzene in 100 ml of tetrahydrofuran. The reaction flask was cooled in an ice bath during this addition, and the reaction mixture was under an atmosphere of nitrogen. The mixture was stirred at ambient temperature for 1 hr. A solution of 20.17 g (0.0693 mole) of ethyl N-(3-phenoxypropyl)isonipecotate in 100 ml of tetrahydrofuran was added and the solution was stirred at room temperature for 16 hr. The mixture was poured into an icy solution of ammonium chloride and the aqueous mixture was extracted with methylene chloride. The methylene chloride solution was extracted with dilute sodium hydroxide and was dried over magnesium sulfate. The solvent was removed in vacuo to give a gummy residue. The residue was treated with a solution of oxalic acid in methanol and the salt was recrystallized from methanol-ether to give 24.17 g (66.2%) of white crystalline solid, m.p. 153°–155° C.

Analysis: Calculated for $C_{29}H_{31}NO_6F_2$: C, 66.02; H, 5.92; N, 2.66. Found: C, 65.78; H, 5.93; N, 2.63.

EXAMPLE 5

4-(Diphenylmethyl)-1-(4-phenoxybutyl)piperidine fumarate [1:1]

A solution of 6.99 g (0.0278 mole) of 4-diphenylmethylpiperidine, 6.64 g (0.029 mole) of (4-bromobutoxy)benzene and 5 g (0.060 mole) of sodium bicarbonate in 400 ml of 1-butanol was refluxed for 11 hr. The solvent was removed in vacuo, and the residue was partitioned between methylene chloride and dilute sodium hydroxide. The methylene chloride solution was dried over magnesium sulfate, and the solvent was removed in vacuo to give an oil, the free base of the title compound. The base was dissolved in 500 ml of ether, and a small amount of solid was filtered from the solution. To the filtrate was added a solution of 3.2 g (0.0276 mole) of fumaric acid in 60 ml of methanol. A white precipitate was collected to give 7.97 g (55.7%) of white crystalline solid, m.p. 146°–147° C.

Analysis: Calculated for $C_{32}H_{37}NO_5$: C, 74.54; H, 7.23; N, 2.72. Found: C, 74.68; H, 7.24; N, 2.68.

EXAMPLE 6

4-(Diphenylmethyl)-1-(3-phenoxypropyl)piperidine fumarate [1:1]

Following the procedure of Example 5, 4-(diphenylmethyl)piperidine and (3-bromopropoxy)benzene were reacted to give the free base of the title compound which was reacted with fumaric acid in methanol to give the white fumarate salt in 71% yield, m.p. 171°–172° C.

Analysis: Calculated for $C_{31}H_{35}NO_5$: C, 74.23; H, 7.03; N, 2.79. Found: C, 74.62; H, 7.03; N, 2.73.

EXAMPLE 7

4-[Bis(4-fluorophenyl)methyl]-1-(3-phenoxypropyl)-piperidine oxalate [1:1]

Following the procedure of Example 2, 4-[bis(4-fluorophenyl)methyl]piperidine and (3-bromopropoxy)benzene were reacted to give the free base of the title compound which was reacted with oxalic acid recrystallizing from methanol-diethyl ether to give the white oxalate salt in 60% yield, m.p. 178°–181° C.

Analysis: Calculated for $C_{29}H_{31}NO_5F_2$: C, 68.09; H, 6.11; N, 2.74. Found: C, 68.37; H, 6.13; N, 2.76.

EXAMPLE 8

4-(Diphenylmethyl)-1-(2-phenoxyethyl)piperidine fumarate [1:1]

Following the procedure of Example 5, 4-(diphenylmethyl)piperidine and (2-bromoethoxy)benzene were reacted to give the free base of the title compound which was reacted with fumaric acid in ether-methanol mixture to give the white fumarate salt in 85% yield, m.p. 189°–190° C.

Analysis: Calculated for $C_{30}H_{33}NO_5$: C, 73.90; H, 6.82; N, 2.87. Found: C, 74.07; H, 6.91; N, 2.85.

EXAMPLE 9

4-[Bis(4-fluorophenyl)methyl]-1-(2-phenoxyethyl)-piperidine oxalate [1:1]

A mixture, 5.83 g (0.02 mole) of 4-[bis(4-fluorophenyl)methyl]piperidine 4.02 g (0.02 mole) of (2-bromoethoxy)benzene and sodium carbonate (3.18 g, 0.03 mole) was heated overnight at gentle reflux in 300 ml of 1-butanol. The reaction was filtered and solvent removed in vacuo. The residue was dissolved in chloroform and extracted with water and 5% sodium hydroxide. Removal of chloroform gave an oil which was converted to the oxalate salt. The salt was recrystallized from methanol-diethyl ether to give 6.0 g (60.3%) of white crystalline product, m.p. 180°–182° C.

Analysis: Calculated for $C_{28}H_{29}NO_5F_2$: C, 67.60; H, 5.88; N, 2.82. Found: C, 67.68; H, 5.87; N, 2.81.

EXAMPLE 10

4-[Bis(4-fluorophenyl)methyl]-1-(4-phenoxybutyl)-piperidine oxalate [1:1]

Following the procedure of Example 2, 4-[bis(4-fluorophenyl)methyl]piperidine and (4-bromopropoxy)benzene were reacted to give the free base of the title compound which was reacted with oxalic acid to give the white oxalate salt (recrystallizing from methanol-diethyl ether), in 48% yield, m.p. 206° C.

Analysis: Calculated for $C_{30}H_{33}NO_5F_2$: C, 68.56; H, 6.33; N, 2.67. Found: C, 68.79; H, 6.35; N, 2.67.

EXAMPLE 11

4-[(4-Fluorophenyl)-phenylmethyl]-1-(3-phenoxypropyl)piperidine fumarate [1:1]

A mixture of 5.4 g (0.02 mole) of 4-[α-(p-fluorophenyl)-α-phenylmethyl]piperidine, 4.5 g (0.021 mole) of (3-bromopropoxy)benzene and 8.0 g (0.075 mole) of anhydrous sodium carbonate in 150 ml of acetonitrile was refluxed for about 20 hr and concentrated under reduced pressure to give a gummy residue. The residue was purified by column chromatography on 160 g of Florisil ® and the product was eluted with 2% acetone in benzene to give an oil, the free base of the title compound. The free base was reacted with fumaric acid and the salt was recrystallized from isopropyl alcohol to give 4.0 g (38%) of white solid, m.p. 169°–171° C. (with decomposition).

Analysis: Calculated for $C_{31}H_{34}FNO_5$: C, 71.66; H, 6.60; N, 2.70. Found: C, 71.37; H, 6.55; N, 2.66.

EXAMPLE 12

4-[Bis(4-fluorophenyl)methyl]-1-[2,6-dichlorophenyoxy)ethyl]piperidine

A mixture of 6.13 g (0.021 mole) of 4-[bis(4-fluorophenyl)methyl]piperidine, 5.38 g (0.03 mole) of 2-(2-bromoethoxy)-1,3-dichlorobenzene was heated overnight at gentle reflux in 200 ml of 1-butanol. The reaction mixture was filtered and stripped to dryness. The residue was dissolved in chloroform and extracted with water and 5% sodium hydroxide solution. The oil which was obtained was chromatographed on 300 g of silica gel using hexane-ethyl acetate (50/50 v/v) as eluant. The fractions containing product were combined and solvent removed to furnish an oil. The oil was dried overnight in vacuo at 80° C. This furnished 5.99 g (59%) of product oil.

Analysis: Calculated for $C_{26}H_{25}NOF_2Cl_2$: C, 65.55; H, 5.29; N, 2.94. Found: C, 65.43; H, 5.34; N, 2.77.

The $^1H$ NMR spectrum of the subject compound was obtained in $CDCl_3$, containing tetramethylsilane and is consistent with the structure indicated by the title,

| | | |
|---|---|---|
| 1.1–2.3 $\sigma$ | aliphatic protons (cyclic) | 7 H |
| 2.8 $\sigma$ or triplet | $CH_2$ next to N | 2 H |
| 2.8–3.1 $\sigma$ | Hydrogen next to N | 2 H |
| 3.5 $\sigma$ doublet | methine proton | 1 H |
| 4.1 $\sigma$ triplet | $CH_2$ next to oxygen | 2 H |
| 6.8–7.4 $\sigma$ | aromatic protons | 11 H |

EXAMPLE 13

1-[3-(4-Chlorophenoxy)propyl]-α,α-bis(4-fluorophenyl)-4-piperidinemethanol

A mixture of 3.0 g (0.01 mole) of [α,α-bis(p-fluorophenyl)]-4-piperidinemethanol, 2.0 g (0.01 mole) of 1chloro-4-(3-chloropropoxy)benzene, 5.3 g (0.05 mole) of anhydrous sodium carbonate and 0.3 g of potassium iodide in 100 ml of 1-butanol was refluxed for 20 hr to give, after working up as in Example 1 (recrystallizing the free base from isopropyl alcohol), 1.7 g (36%) of white solid, m.p. 92°–93° C.

Analysis: Calculated for $C_{27}H_{28}ClF_2NO_2$: C, 68.71; H, 5.98; N, 2.97. Found: C, 68.66; H, 5.99; N, 2.92.

EXAMPLE 14

4-[Bis(4-fluorophenyl)methyl]-1-[3-(2-fluorophenoxy)propyl]piperidine oxalate [1:1]

A mixture of 5.85 g (0.02 mole) of 4-[bis(4-fluorophenyl)methyl]piperidine, 3.76 g (0.02 mole) of 2-(3-chloropropoxy)-1-fluorobenzene, and sodium carbonate (4.80 g, 0.045 mole) in 300 ml of 1-butanol containing 0.3 g of potassium iodide was heated overnight at gentle reflux. The reaction mixture was stripped to dryness and the resulting oil partitioned between chloroform-5% sodium hydroxide and then between chloroform-water. Removal of chloroform gave an oil which was converted to the oxalate salt. The salt was recrystallized from methanol-diethyl ether. The salt was subsequently triturated with isopropanol, and was dried overnight at 80° C. to give 5.82 g (55%) of product, m.p. 182°–183° C.

Analysis: Calculated for $C_{29}H_{30}NO_5F_3$: C, 65.78; H, 5.71; N, 2.65. Found: C, 66.05; H, 5.79; N, 2.59.

EXAMPLE 15

4-[Bis(4-fluorophenyl)methyl]-1-[3-(3-fluorophenoxy)propyl]piperidine mandelate [1:1]

Following the procedure of Example 14, 4-[bis(4-fluorophenyl)methyl]piperidine and 3-(3-chloropropoxy)-1-fluorobenzene were reacted to give the free base of the title compound which was reacted with mandelic acid to give the white mandelate salt (recrystallizing from isopropyl alcohol) in 62% yield, m.p. 145°–147.5° C.

Analysis: Calculated for $C_{35}H_{36}NO_4F_3$: C, 71.05; H, 6.13; N, 2.37. Found: C, 71.10; H, 6.20; N, 2.36.

EXAMPLE 16

4-[Bis(4-fluorophenyl)methyl]-1-[3-(4-chlorophenoxy)propyl]piperidine fumarate [1:1]

Following the procedure of Example 14, 4-[bis(4-fluorophenyl)methyl]piperidine and 1-[4-(3-chloropropoxy)]chlorobenzene were reacted to give the free base of the title compound. The free base was chromatographed on silica gel eluting with hexane-ethyl acetate and reacted with fumaric acid (recrystallizing from methanol-diethyl ether) in 9% yield, m.p. 169°–170° C.

Analysis: Calculated for $C_{31}H_{32}NO_5F_2Cl$: C, 65.10; H, 5.64; N, 2.45. Found: C, 64.85; H, 5.63; N, 2.46.

EXAMPLE 17

4-[Bis(4-fluorophenyl)methyl]-1-[3-(4-fluorophenoxy)propyl]piperidine

Following the combined procedures of Examples 14 and 16, 4-[bis(4-fluorophenyl)methyl]piperidine and 4-(3-chloropropoxy)-1-fluorobenzene were reacted and worked up by chromatography in Example 16, to give the free base in 53% yield as a yellow oil after drying in vacuo at 80° C. overnight.

Analysis: Calculated for $C_{27}H_{28}NOF_3$: C, 73.78; H, 6.42; N, 3.19. Found: C, 73.64; H, 6.39; N, 3.14.

EXAMPLE 18

4-[Bis(4-fluorophenyl)methyl]-1-[3-(4-methoxyphenoxy)propyl]piperidine fumarate [1:1]

Following the procedure of Example 14, 4-[bis(4-fluorophenyl)methyl]piperidine and 1-(3-chloropropoxy)-4-methoxybenzene were reacted to give the free base of the title compound which was reacted with fumaric acid to give the white fumarate salt (recrystallizing from methanol-diethyl ether) in 64% yield, m.p. 172°–173° C.

Analysis: Calculated for $C_{32}H_{35}NO_6F_2$: C, 67.71; H, 6.22; N, 2.47. Found: C, 67.89; H, 6.25; N, 2.39.

EXAMPLE 19

4-[Bis(4-fluorophenyl)methyl]-1-[3-(2-methoxyphenoxy)propyl]piperidine

A mixture of 5.99 g (0.021 mole) of 4-[bis(4-fluorophenyl)methyl]piperidine, 4.35 g (0.022 mole) of 2-(3-chloropropoxy)-1-methoxybenzene ether, and sodium carbonate (3.18 g, 0.03 mole) in 1-butanol was heated overnight at gentle reflux. The reaction mixture was filtered and stripped to dryness. The residue was dissolved in chloroform and extracted with water and 5% sodium hydroxide. Removal of chloroform gave a dark brown oil. The oil was chromatographed on silica gel using acetone-ethyl acetate for elution. After combining fractions and removing solvent, an oil was obtained. The oil was dried in vacuo at 80° C. overnight. This gave 3.18 g (33.5%) of title product.

Analysis: Calculated for $C_{28}H_{31}NO_2F_2$: C, 74.48; H, 6.92; N, 3.12. Found: C, 74.42; H, 6.95; N, 3.00.

The $^1$NMR spectrum of the subject compound was obtained in $CDCl_3$ containing tetramethyl silane and is consistent with the structure indicated by the title.

| | | |
|---|---|---|
| 6.8 σ | singlet; or protons on ring containing methoxy group. | 4 H |
| 6.8–7.3 σ | aromatic protons on fluoro-phenyl rings. | 8 H |
| 4.0 σ | triplet $CH_2$—O. | 2 H |
| 3.8 σ | singlet O—$CH_3$. | 3 H |
| 3.4 σ | doublet; methine proton. | 1 H |
| 0.8–3.1 σ | multiplet. | 13 H |

EXAMPLE 20

α,α-Bis(4-fluorophenyl)-1-[3-(2-methoxyphenoxy)-propyl]-4-piperidinemethanol

Following the procedure of Example 1, [α,α-bis(p-fluorophenyl)]-4-piperidinemethanol and 1-chloro-3-(2-methoxyphenoxy)propane were reacted using in addition potassium iodide catalyst to give the title compound in 66% yield, (recrystallizing from isopropyl alcohol), m.p. 127°–218° C.

Analysis: Calculated for $C_{28}N_{31}F_2NO_3$: C, 71.93; H, 6.68; N, 3.00. Found: C, 71.88; H, 6.67; N, 2.98.

EXAMPLE 21

4-[Bis(4-fluorophenyl)methylene]-1-[3-(2-methoxy-phenoxy)propyl]piperidine oxalate [1:1]

Following the procedure of Example 14, 4-[bis(4-fluorophenyl)methylene]piperidine and 2-(3-chloropropoxy)-1-methoxybenzene were reacted using in addition potassium iodide catalyst to give the free base of the title compound which was related with oxalic acid to give the white oxalate salt (recrystallizing from methanol-diethyl ether) in 73% yield, m.p. 184°–186° C.

Analysis: Calculated for $C_{30}H_{31}NO_6F_2$: C, 66.78; H, 5.79; N, 2.60. Found: C, 66.74; H, 5.79; N, 2.61.

EXAMPLE 22

4-[Bis(4-fluorophenyl)methyl]-1-[3-(3,4-dimethoxy-phenoxy)propyl]piperidine oxalate [1:1]

A mixture of 6.02 g (0.021 mole) of 4-[bis(4-fluorophenyl)methyl]piperidine, 4.83 g (0.021 mole) of 4-(3-chloropropoxy)-1,2-dimethoxybenzene, and potassium carbonate (5.52 g, 0.04 mole) was refluxed overnight in 300 ml of 1-butanol containing potassium iodide (0.3 g). The reaction mixture was stripped to dryness and partitioned between chloroform and water several times. The chloroform layer was dried over anhydrous sodium sulfate and then filtered. The chloroform was removed by rotary evaporator. The oil obtained was converted to the oxalate salt and then recrystallized from methanol-diethyl ether and methanol isopropanol ether. This furnished 7.77 g (64.7%) of white solid; m.p. 188° C.

Analysis: Calculated for $C_{31}H_{35}NO_7F_2$: C, 65.14; H, 6.17; N, 2.43. Found: C, 64.78; H, 6.14; N, 2.44.

EXAMPLE 23

4-[Bis(4-methylphenyl)methyl]-1-[3-(2,6-dimethoxy-phenoxy)propyl]piperidine fumarate [1:1]

Following the procedure of Example 22, 4-[bis(4-methylphenyl)methyl]piperidine and 2-(3-chloro-propoxy)-1,3-dimethoxybenzene were reacted to give the free base of the title compound which was reacted with fumaric acid to give the white fumarate salt (recrystallizing from methanol-diethyl ether in 66% yield, m.p. 206°–207° C.

Analysis: Calculated for $C_{35}H_{43}NO_7$: C, 71.29; H, 7.35; N, 2.38. Found: C, 71.24; H, 7.38; N, 2.36.

EXAMPLE 24

4-[Bis(4-fluorophenyl)methylene]-1-[3-(3,4-dimethoxyphenoxy)propyl]piperidine oxalate [1:1]

Following the procedure of Example 22, 4-[bis(4-fluorophenyl)methylene]piperidine and 4-(3-chloropropoxy)-1,2-dimethoxybenzene were reacted to give the free base of the title compound which was reacted with oxalic acid to give the cream colored oxalate salt (recrystallizing from methanol-diethyl ether) in 51% yield, m.p. 173°–176° C.

Analysis: Calculated for $C_{31}H_{33}NO_7F_2$: C, 65.37; H, 5.84; N, 2.46. Found: C, 65.02; H, 5.83; N, 2.50.

EXAMPLE 25

4-[Bis(4-fluorophenyl)methyl]-1-[3-(2,6-dimethoxy-phenoxy)propyl]piperidine oxalate hydrate [1:1:1]

Following the procedure of Example 22, but substituting dimethoxy ethane for butanol, 4-[bis(4-fluorophenyl)methyl]piperidine and 2-(3-chloropropoxy)-1,3-dimethoxybenzene were reacted to give the free base of the title compound which was reacted with oxalic acid to give the white oxalate salt (recrystallizing from methanol-diethyl ether) in 9% yield, m.p. 132°–134° C.

Analysis: Calculated for $C_{31}H_{37}NO_8F_2$: C, 63.15; H, 6.32; N, 2.38. Found: C, 62.89; H, 5.98; N, 2.41.

EXAMPLE 26

4-[Bis(4-fluorophenyl)methyl]-1-[3-(3,5-dimethoxy-phenoxy)propyl]piperidine

A mixture of 5.51 g (0.019 mole) of 4-[bis(4-fluorophenyl)methyl]piperidine, 4.42 g (0.019 mole) of 1-(3-chloropropoxy)-3,5-dimethoxybenzene and potassium carbonate (5.53 g, 0.04 mole) was heated overnight to reflux in 350 ml of 1-butanol containing potassium iodide (0.3 g). The reaction mixture was stripped to dryness and the residue partitioned between chloroform-5% sodium hydroxide and chloroform-water. Removal of chloroform gave a brown oil. The oil was subjected to chromatography on a silica gel column using a gradient elution series of hexane-ethyl acetate and ethyl acetate-dimethoxyethane. After combining proper fractions eluted from the column and removing solvent, the residual oil was dried in vacuo overnight at 80° C. This produced 2.61 g (28.5%) of brown oil.

Analysis: Calculated for $C_{29}H_{33}NO_3F_2$: C, 72.33; H, 6.91; N, 2.91. Found: C, 71.62; H, 6.80; N, 2.98.

The $^1$H NMR spectrum of the subject compound was obtained in $CDCl_3$ containing tetramethylsilane and is consistent with the structure indicated by the title: 7.0 σ (multiplet, aromatic protons on fluorophenyl ring, 6.0 (singlet, aromatic protons on methoxyphenyl ring, 3H), 2.8 (triplet, methylene next to ether oxygen, 2H), 3.75

(singlet, OCH₃, 6H), 3.4 (doublet, methine attached to two aromatic rings, 1H), 0.75–2.6 (multiplet, remaining aliphatics, 13H).

EXAMPLE 27

4-[Bis(4-methoxyphenyl)methyl]-1-[3-(3,4-dimethoxyphenoxy)propyl]piperidine

A mixture of 5.58 g (0.02 mole) of 4-[bis(4-methoxyphenyl)methyl]piperidine, 4.83 g (0.021 mole) of 4-(3-chloropropoxy)-1,2-dimethoxybenzene, and potassium carbonate, 5.52 g (0.04 mole) was heated overnight at reflux in 350 ml of 1-butanol containing potassium iodide (0.3 g). The reaction mixture was stripped to dryness, and the residue partitioned between chloroform-5% sodium hydroxide and chloroform-water. Removal of chloroform gave a dark brown oil. The oil was subjected to column chromatography on a silica gel column with elution via ethyl acetate-dimethoxy ethane. This produced 4.72 g (46.7%) of dark brown oil.

Analysis: Calculated for C₃₁H₃₉NO₅: C, 73.64; H, 7.77; N, 2.77. Found: C, 72.38; H, 7.70; N, 2.72.

The ¹H NMR spectrum of the subject compound was obtained in CDCl₃ containing tetramethylsilane and is consistent with the structure indicated by the title: 7.1 σ (multiplet, aromatic protons ortho to methine of

6.75 (multiplet, aromatic protons adjacent to methoxy groups, 5H), 6.4 (multiplet, aromatic protons adjacent to ether linkage, 2H), 3.9 (triplet, methylene protons next to ether linkage, 2H), 3.7 (OCH₃, 6H), 3.6 (OCH₃, 6H), 3.3 (doublet, methine attached to aromatic rings, 1H), 0.75–3.0 (multiplet, aliphatic protons, 13H).

EXAMPLE 28

4-[Bis(4-methoxyphenyl)methyl]-1-[3-(4-methoxyphenoxy)propyl]-piperidine fumarate hydrate [1:1]

Following the procedure of Example 22, 4-[bis(4-methoxyphenyl)methyl]piperidine and 4-(3-chloropropoxy)-1-methoxybenzene were reacted to give the free base of the title compound which was separated by extracting with sodium hydroxide-chloroform and reacted with fumaric acid to give the title salt (recrystallizing from methanol-diethyl ether several times as well as isopropyl alcohol) in 15% yield, m.p. 163°–165° C.

Analysis: Calculated for C₃₄H₄₂NO₈.₅: C, 67.98; H, 7.05; N, 2.33. Found: C, 68.16; H, 6.97; N, 2.34.

EXAMPLE 29

1-[4-[3-[4-[Bis(4-fluorophenyl)methylene]-1-piperidinyl]propoxy]phenyl]ethanone oxalate [1:1]

Following the procedure of Example 2, 4-[bis(4-fluorophenyl)methylene]piperidine and 1-[4-(3-chloropropoxy)phenyl]ethanone, substituting sodium carbonate for sodium bicarbonate, were reacted to give the free base of the title compound which was reacted with oxalic acid to give the oxalate salt (recrystallizing from methanol-diethyl ether) in 59% yield, m.p. 196°–198° C.

Analysis: Calculated for C₃₁H₃₃NO₆F₂: C, 67.26; H, 6.01; N, 2.53. Found: C, 66.94; H, 6.01; N, 2.40.

EXAMPLE 30

1-[4-[3-[4-[Bis(4-fluorophenyl)methyl]-1-piperidinyl]propoxy]phenyl]ethanone, oxalate [1:1]

Following the procedure of Example 2, 4-[bis(4-fluorophenyl)methyl]piperidine and 1-[4-(3-chloropropoxy)phenyl]ethanone and substituting sodium carbonate for sodium bicarbonate were reacted to give the free base of the title compound which was reacted with oxalic acid to give the oxalate salt (recrystallizing from methanol-diethyl ether) in 75% yield, m.p. 141°–143° C.

Analysis: Calculated for C₃₁H₃₃NO₆F₂: C, 67.26; H, 6.01; N, 2.53. Found: C, 66.94; H, 6.01; N, 2.40.

EXAMPLE 31

1-[4-[3-[4-[Bis(4-fluorophenyl)hydroxymethyl]-1-piperidinyl]propoxy]-phenyl]ethanone compound with 2propanol [1:1]

Following the procedure of Example 1, [α,α-bis(p-fluorophenyl)]-4-piperidinemethanol and 1-[4-(3-chloropropoxy)phenyl]ethanone were reacted using potassium iodide catalyst to give the free base of the title compound which when recrystallized from isopropyl alcohol gave the white title compound in 71% yield, m.p. 72°–84° C.

Analysis: Calculated for C₂₉H₃₁F₂NO₃·C₃H₈O: C, 71.22; H, 7.28; N, 2.60. Found: C, 71.26; H, 7.34; N, 2.56.

NMR indicated that the solid contained one mole of 2-propanol as a solvate.

EXAMPLE 32

1-[4-[3-[4-[Bis(4-fluorophenyl)hydroxymethyl]-1-piperidinyl]propoxy]-3-methyphenyl]ethanone Following the procedure of Example 1, [α,α-bis(p-fluorophenyl)]-4-piperidinemethanol and 1-[4-(3-chloropropoxy)-3-methylphenyl]ethanone were reacted using potassium iodide catalyst to give the white title compound (recrystallizing from isopropyl alcohol) in 76% yield, m.p. 116°–117° C.

Analysis: Calculated for C₃₀H₃₃F₂NO₃: C, 73.00; H, 6.74; N, 2.84. Found: C, 72.90; H, 6.80; N, 2.78.

EXAMPLE 33

4-[3-[4-[Bis(4-fluorophenyl)hydroxymethyl]-1-piperidinyl]propoxy]benzonitrile

Following the procedure of Example 1, [α,α-bis(p-fluorophenyl)]-4-piperidinemethanol and 4-(3-chloropropoxy)benzonitrile were reacted using potassium iodide as catalyst to give the white title compound (recrystallizing from isopropyl alcohol-isopropyl ether) in 30% yield, m.p. 107°–108° C.

Analysis: Calculated for C₂₈H₂₈F₂N₂O₂: C, 72.71; H, 6.10; N, 6.06. Found: C, 72.82; H, 6.11; N, 6.05.

EXAMPLE 34

4-[3-[4-[Bis(4-fluorophenyl)methyl]-1-piperidinyl]propoxy]benzonitrile fumarate [1:1]

Following the procedure of Example 22, 4-[bis(4-fluorophenyl)methyl]piperidine and 4-(3-chloropropoxy)cyanobenzene were reacted using potassium iodide catalyst to give the free base of the title compound which was reacted with fumaric acid to give the fumarate salt which was (recrystallized from methanol-diethyl ether) in 53% yield, m.p. 167° C.

Analysis: Calculated for C₃₂H₃₂N₂O₅F₂: C, 68.32; H, 5.73; N, 4.98. Found: C, 68.10; H, 5.70; N, 4.94.

EXAMPLE 35

4-[3-[4-[Bis(4-fluorophenyl)hydroxymethyl]-1-piperidinyl]propoxy]benzoic acid ethyl ester hydrochloride [1:1]

A mixture of 6.0 g (0.02 mole) of [α,α-bis(p-fluorophenyl]-4-piperidinemethanol, 5.0 g (0.02 mole) of 4-(3-chloropropoxy)benzoic acid methyl ester, 7.4 g (0.07 mole) of anhydrous sodium carbonate, 0.3 g of potassium iodide and 150 ml of dimethylformamide was heated on a steam bath for 20 hr and then poured into 1.5 liter of ice-water. A gum precipitated and the aqueous solution was decanted. The gum was dissolved in benzene and the solution was washed with water and dilute sodium hydroxide solution, dried over anhydrous sodium sulfate and concentrated under reduced pressure to give 9.2 g of gum as residue. The gum was purified by column chromatography on 200 g of Florisil ® and the desired product was eluted with 20 % acetone in benzene. The fractions containing the free base of the title compound were combined and concentrated under reduced pressure to give a gum, the free base, as residue. The free base was converted to the hydrochloric acid salt which was recrystallized from 2-propanol to give 5.3 g (49%) of white powder, m.p. 193.5°–194.5° C.

Analysis: Calculated for $C_{30}H_{34}ClF_2NO_4$: C, 65.99; H, 6.28; N, 2.57. Found: C, 66.16; H, 6.32; N, 2.56.

EXAMPLE 36

4-[3-[4-[Bis(4-fluorophenyl)hydroxymethyl]-1-piperindinyl]propoxy]benzoic acid hydrochloride hydrate [1:1:0.5]

A solution of 2.7 g (0.005 mole) of 4-[3-[4-[bis(4-fluorophenyl)hydroxymethyl]-1-piperidinyl]propoxy]benzoic acid ethyl ester and 1.2 g (0.022 mole) of potassium hydroxide in 50 ml of ethanol and 20 ml of water was heated on a steam bath for 2 hr. Acetic acid, 10 ml, was added and the solution was poured into 500 ml of ice water and the mixture was allowed to stand at ambient temperature overnight. Sodium chloride was added to the mixture to give a coagulated solid. The solid was collected by filtration and air dried. The solid was dissolved in 20 ml of isopropyl alcohol and the solution was poured into 30 ml of ethereal hydrogen chloride. The salt which gradually crystallized was collected by filtration, washed with ethyl ether and dried to give 0.2 g (8%) of white powder, m.p. 148°–158° C. with decomposition.

Analysis: Calculated for $C_{19}H_{30}ClF_2NO_4 \cdot 0.5H_2O$: C, 63.82; H, 5.93; N, 2.66. Found: C, 63.97; H, 6.25; N, 2.51.

EXAMPLE 37

4-[3-[4-[Bis(4-fluorophenyl)methylene]-1-piperidinyl]propoxy]benzoic acid ethyl ester hydrobromide [1:1]

A mixture of 6.09 g (0.021 mole) of 4-[bis(4-fluorophenyl)methylene]piperidine, 5.20 g (0.02 mole) of 1-[4-(3-chloropropoxy)-phenyl]carbethoxybenzene and sodium carbonate 4.30 g (0.04 mole) in 230 ml of 1-butanol containing potassium iodide (0.3 g) was heated overnight at gentle reflux. The reaction mixture was stripped to dryness and partitioned between chloroform water and chloroform-5% sodium hydroxide. Removal of chloroform gave an oil. The oil was converted to the hydrobromide salt using hydrogen bromide in glacial acetic acid. The acetic acid and excess hydrogen bromide were removed in vacuo. The salt was recrystallized from methanol-diethyl ether. The salt was washed with water to remove acetamide present as an impurity. The salt was washed with diethyl ether and dried in vacuo overnight at 80° C. A yield of 6.81 g (59.5%) of white solid, m.p. 192°–194° C., was obtained.

Analysis: Calculated for $C_{30}H_{32}NO_3F_2Br$: C, 62.94; H, 5.63; N, 2.45. Found: C, 62.83; H, 5.58; N, 2.45.

EXAMPLE 38

4-[3-[4-[Bis(4-fluorophenyl)methyl]-1-piperidinyl]propoxy]benzoic acid ethyl ester hydrobromide [1:1]

Following the procedure of Example 14, 4-[bis(4-fluorophenyl)methyl]piperidine and 4-(3-chloropropoxy)benzoic acid ethyl ester were reacted using potassium iodide as catalyst to give the free base which was reacted with hydrogen bromide in glacial acetic acid. The oil was stripped to dryness and the solid obtained was recrystallized from isopropyl alcohol-diethyl ether to give the white salt in 20% yield, m.p. 142°–144° C.

Analysis: Calculated for $C_{30}H_{34}NO_3F_2Br$: C, 62.72; H, 5.97; N, 2.44. Found: C, 62.66; H, 5.95; N, 2.45.

EXAMPLE 39

4-[3-[4-[Bis(4-methoxyphenyl)methyl]-1-piperidinyl]propoxy]benzoic acid butyl ester A mixture of 6.22 g (0.02 mole) of 4-[bis(4-methoxyphenyl)methyl]piperidine, 4.84 g (0.02 mole) of 4-(3-chloropropoxy)benzoic acid ethyl ester, and potassium carbonate, 5.60 g (0.04 mole) in 350 ml of 1-butanol was refluxed overnight with potassium iodide. The reaction mixture was stripped to dryness and the residue partitioned between chloroform-5% sodium hydroxide then chloroform-water. Removal of chloroform gave an oil. This oil was chromatographed on a 200 g silica gel comumn packed in 50/50 v/v hexane-ethyl acetate. The material was eluted with hexane-ethyl acetate mixtures and finally 1% methanol-ethyl acetate.

From the chromatography was obtained 5.09 g (46.6%) of an oil.

Analysis: Calculated for $C_{34}H_{43}NO_5$: C, 74.83; H, 7.94; N, 2.57. Found: C, 74.19; H, 7.91; N, 2.53.

The $^1H$ NMR spectrum was obtained in tetramethylsilane and is consistent with the structure indicated by the title, σ 8.0 (H's ortho to $CO_2$, 2H), 6.8 (m, aromatic, 10H), 4.2 (m, $CH_2$ alpha to 0, 4H), 3.7 (S, $OCH_3$, 6H), 0.9–3.5 (m, aliphatics, 21H).

EXAMPLE 40

4-[3-[4-[Bis(4-methoxyphenyl)methyl]-1-piperidinyl]propoxy]benzoic acid ethyl ester fumarate hydrate [1:1:0.5]

Following the procedure of Example 22, but substituting dimethylformamide at 73° C. for butanol, 4-[bis(4-methoxyphenyl)methyl]piperidine and 4-(3-chloropropoxy)benzoic acid ethyl ester were reacted to give the free base of the title compound which was reacted with fumaric acid, to give the white fumarate salt (recrystallizing from methanoldiethyl ether) in 27% yield, m.p. 147.5°–148.5° C.

Analysis: Calculated for $C_{36}H_{44}NO_{9.5}$: C, 67.27; H, 6.90; N, 2.18. Found: C, 67.26; H, 6.78; N, 2.19.

EXAMPLE 41

4-[3-[4-[Bis(4-fluorophenyl)hydroxymethyl]-1-piperidinyl]ethoxy]benzoic acid ethyl ester hydrochloride Following the procedure of Example 35, α,α-bis(p-fluorophenyl)-4-piperidine methanol and 4-(2-chloroethoxy)benzoic acid ethyl ester are reacted and the hydrochloride salt is prepared.

EXAMPLE 42

4-[3-[4-[Bis(4-fluorophenyl)hydroxymethyl]-1-piperidinyl]propoxy]-3-methoxybenzeneacetic acid ethyl ester hydrochloride Following the procedure of Example 35, [α,α-bis(p-fluorophenyl)]-4-piperidinemethanol and 4-(3-chloropropoxy)-3-methoxybenzeneacetic acid ethyl ester are reacted and the hydrochloride salt is prepared.

EXAMPLE 43

4-[Bis(4-fluorophenyl)methylene]-1-[3-[4-(1,1-dimethylethyl)phenoxy]propyl]piperidine fumarate [1:1]

Following the procedure of Example 9, 4-[bis(4-fluorophenyl)methylene]piperidine and 4-(3-chloropropoxy)-(1,1-dimethylethyl)benzene were reacted using potassium iodide catalyst to give an oil which was dissolved in ethyl acetate and filtered through silica gel to give the free base of the title compound. The free base was reacted with fumaric acid to give the white fumarate salt (recrystallizing from isopropyl alcohol-diethyl ether) in 40% yield, m.p. 208.5°–209.5° C.

Analysis: Calculated for $C_{35}H_{39}NO_5F_2$: C, 71.05; H, 6.64; N, 2.37. Found: C, 70.91; H, 6.57; N, 2.38.

EXAMPLE 44

4-[Bis(4-fluorophenyl)methyl]-1-[3-[4-(1,1-dimethylethyl)phenoxy]propyl]piperidine fumarate hydrate [1:1:0.5]

Following the procedure of Example 9, 4-[bis(4-fluorophenyl)methyl]piperidine and 4-(3-chloropropoxy)-(1,1-dimethylethyl)benzene were reacted using potassium iodide catalyst to give the free base of the title compound which was reacted with fumaric acid to give the white fumarate salt (recrystallizing from methanol-diethyl ether and isopropyl alcohol-diethyl ether) in 55% yield, m.p. 194°–196° C. with decomposition.

Analysis: Calculated for $C_{35}H_{42}NO_{5.5}F_2$: C, 69.75; H, 7.02; N, 2.32. Founc: C, 70.01; H, 6.89; N, 2.44.

EXAMPLE 45

4-[Bis(4-methoxyphenyl)methyl]-1-[3-[4-(1,1-dimethylethyl)phenoxy]propyl]piperidine oxalate [1:1]

Following the procedure of Example 22, 4-[bis(4-methoxyphenyl)methyl]piperidine and 4-(3-chloropropoxy)-(1,1-dimethylethyl)benzene were reacted using potassium iodide catalyst to give the free base which was reacted with oxalic acid to give the white oxalate salt (recrystallizing from methanol-diethyl ether) in 35% yield, m.p. 212° C.

Analysis: Calculated for $C_{35}H_{45}NO_7$: C, 71.04; H, 7.67; N, 2.37. Found: C, 70.91; H, 7.70; N, 2.35.

EXAMPLE 46

1-[3-[4-(1,1-Dimethylethyl)phenoxy]propyl]-α,α-bis(4-fluorophenyl)-4-piperidinemethanol Following the procedure of Example 1, [α,α-bis(p-fluorophenyl)]-4-piperidinemethanol and 4-(3-chloropropoxy)(1,1-dimethylethyl)benzene were reacted using potassium iodide catalyst to give white powder (recrystallizing from isopropyl alcohol) in 41% yield, m.p. 126°–127° C.

Analysis: Calculated for $C_{31}H_{37}F_2NO_2$: C, 75.43; H, 7.56; N, 2.84. Found: C, 75.21; H, 7.58; N, 2.82.

EXAMPLE 47

4-[Bis(4-fluorophenyl)methyl]-1-[3-[3-(trifluoromethyl)phenoxy]propyl]piperidine oxalate [1:1]

Following the procedure of Example 9, 4-[bis-(4-fluorophenyl)methyl]piperidine and 1-[3-chloropropoxy]-3-trifluoromethylbenzene were reacted using potassium iodide catalyst to give the free base of the title compound which was reacted with oxalic acid to give the white oxalate salt (recrystallizing from methanol-diethyl ether) in 39% yield, m.p. 185°–186° C.

Analysis: Calculated for $C_{30}H_{30}NO_5F_5$: C, 62.17; H, 5.22; N, 2.42. Found: C, 62.54; H, 5.27; N, 2.52.

EXAMPLE 48

N-[4-[3-[4-[Bis(4-methylphenyl)methyl]-1-piperidinyl]propoxy]phenyl Acetamide fumarate hydrate [1:1:0.5]

Following the procedure of Example 22 but substituting dimethylformamide at 73° C. for refluxing butanol, 4-[bis-(4-methylphenyl)methyl]piperidine and N-[4-(3-chloropropoxy)phenyl]acetamide were reacted using potassium iodide catalyst to give the free base of the title compound which was reacted with fumaric acid to give the white fumarate hydrate (recrystallizing from methanol-diethyl ether), m.p. 149°–152° C.

Analysis: Calculated for $C_{35}H_{43}N_2O_{6.5}$: C, 70.57; H, 7.28; N, 4.70. Found: C, 70.80; H, 7.28; N, 4.65.

EXAMPLE 49

N-[4-[3-[4-[Bis(4-fluorophenyl)methyl]-1-piperidinyl]propoxy]phenyl]acetamide hydrobromide [1:1]

A mixture of 25.68 g (0.089 mole) 4-[bis(4-fluorophenyl)methyl]piperidine, 20.3 g (0.089 mole) of N-[4-(3-chloropropoxy)phenyl]acetamide, and potassium carbonate, 21.4 g, (0.155 mole) was stirred overnight at 70°–80° C. in 350 ml of dimethylformamide. The reaction mixture was stripped to dryness and the residue was partitioned between chloroform and water; removal of chloroform gave a dark red oil. The oil was dissolved in glacial acetic acid, and the hydrobromide salt was formed with hydrobromic acid in glacial acetic acid. Solvent was removed in vacuo, and the residue was recrystallized from methanol-diethyl ether. A yield of 21.68 g (43.5%) of pale-white solid, m.p. 223°–225° C. was obtained.

Analysis: Calculated for $C_{29}H_{33}N_2O_2F_2Br$: C, 62.26; H, 5.95; N, 5.01. Found: C, 61.99; H, 5.94; N, 5.01.

EXAMPLE 50

4-[3-[4-[Bis(4-fluorophenyl)methyl]-1-piperidinyl]propoxy]benzeneamine fumarate hydrate [1:1:0.5]

A solution of 11.8 g (0.02709 mole) of N-[4-[3-[bis(4-fluorophenyl)methyl]-1-piperidinyl]propoxy]acetamide was heated at gentle reflux for four hours in 500 ml of methanol containing 500 ml of 6N hydrochloric acid. The reaction was stopped and allowed to cool overnight. The reaction mixture was evaporated to a small volume on the rotary evaporator, diluted with water and made alkaline with 5% sodium hydroxide. The reaction mixture was then partitioned between the alkaline phase and chloroform. The chloroform layer was dried, filtered, and solvent removed to give an oil. The oil was converted to the fumarate salt and the salt was recrystallized from methanol-diethyl ether. The white solid obtained was dried overnight in vacuo at 80° C. to give 8.49 g (71%) of white crystalline product, m.p. 121.5°–124.0° C.

Analysis: Calculated for $C_{31}H_{35}N_2O_{5.5}F_2$: C, 66.30; H, 6.28; N, 4.99. Found: C, 66.49; H, 6.13; N, 4.92.

EXAMPLE 51

N-[4-[3-[4-[Bis(4-fluorophenyl)hydroxymethyl]-1-piperidinyl]propoxy]phenyl]acetamide hydrochloride hydrate [1:1:1]

A mixture of 3.0 g (0.01 mole) of [α,α-bis(p-fluorophenyl)]-4-piperidinemethanol, 2.3 g (0.01 mole) of N-[4-(3-chloropropoxy)phenyl]acetamide, 5.3 g (0.05 mole) of anhydrous sodium carbonate and 0.3 g of potassium iodide in 100 ml of 1-butanol gave a gum as residue. The gum was purified by column chromatography on 80 g of Florisil ® and the product was eluted with 20% acetone in benzene. The combined fractions containing product were concentrated under reduced pressure to give a glass as residue. The glass was dissolved in ethyl ether, filtered through cotton, and the filtrate treated with ethereal hydrogen chloride. The resulting solid was collected by filtration, washed with ethyl ether and dried to yield 2.1 g (38%) of white solid, m.p. 135°–170° C. (with decomposition).

Analysis: Calculated for $C_{29}H_{33}ClF_2N_2O_3 \cdot H_2O$: C, 63.44; H, 6.43; N, 5.10. Found: C, 63.32; H, 6.56; N, 4.92.

EXAMPLE 52

α,α-Bis(4-fluorophenyl)-1-[3-(4-nitrophenoxy)propyl]-4-piperidinemethanol

Following the procedure of Example 1 and using potassium iodide catalyst, a mixture of 9.1 g (0.03 mole) of [α,α-bis(p-fluorophenyl)]-4-piperidinemethanol and 6.7 g (0.03 mole) of 1-(3-chloropropoxy)-4-nitrobenzene were reacted to give 10.5 g of the title compound which was recrystallized from isopropyl ether, m.p. 93.5°–94.5° C.

Analysis: Calculated for $C_{27}H_{28}F_2N_2O_4$: C, 67.21; H, 5.85; N, 5.81. Found: C, 67.05; H, 5.83; N, 5.74.

EXAMPLE 53

4-[3-[4-[Bis(4-fluorophenyl)hydroxymethyl]-1-piperidinyl]propoxy]benzamide

Following the procedure of Example 1 and using potassium iodide catalyst, a mixture of 3.0 g (0.01 mole) of [α,α-bis(p-fluorophenyl)]-4-piperidinemethanol, 1 g (0.01 mole) of 4-(3-chloropropoxy)benzamide and 6.9 g (0.05 mole) of anhydrous potassium carbonate in 100 ml of 1-butanol were reacted to give 3.0 g (63%) of white powder, m.p., 200°–204° C. The recrystallizing solvent used was absolute ethanol.

Analysis: Calculated for $C_{28}H_{30}F_2N_2O_3$: C, 69.98; H, 6.29; N, 5.83. Found: C, 69.61; H, 6.49; N, 5.70.

EXAMPLE 54

4-[Bis(4-fluorophenyl)methyl]-1-[2-(1-naphthalenyloxy)ethyl]piperidine hydrochloride [1:1]

A mixture of 2.84 g (0.0099 mole) of 4-[α,α-bis(p-fluorophenyl)methyl]piperidine, 3.01 g (0.012 mole) of 1-(2-bromoethoxy)naphthalene and 5.0 g (0.060 mole) of sodium bicarbonate in 400 ml of 1-butanol was refluxed for 16 hr. The solvent was removed in vacuo and the residue was partitioned between methylene chloride and dilute sodium hydroxide. The methylene chloride solution was dried over magnesium sulfate, and the solvent was removed in vacuo to give an oil. This was dissolved in a mixture of ether and methanol, an excess of ethereal hydrochloride was added, and a white precipitate was collected to give 3.13 g (64%) of white crystalline solid, m.p. 155°–158° C.

Analysis: Calculated for $C_{30}P_{30}MOF_2Cl$: C, 72.94; H, 6.12; N, 2.84. Found: C, 73.20; H, 6.10; N, 2.78.

EXAMPLE 55

4-[Bis(4-fluorophenyl)methyl]-1-[2-(2-naphthalenyloxy)ethyl]piperidine oxalate [1:1]

Following the procedure of Example 54 and substituting 2-(2-bromoethoxy)naphthalene and oxalic acid for hydrogen chloride, the title compound was obtained in 61.9% yield as white crystalline solid, m.p. 168°–171° C.

Analysis: Calculated for $C_{32}H_{31}NO_5F_2$: C, 70.19; H, 5.71; N, 2.56. Found: C, 70.26; H, 5.75; N, 2.63.

EXAMPLE 56

1-[4-[3-[4-[Bis(4-fluorophenyl)methyl]-1-piperidinyl]propoxy]-3-methoxyphenyl]ethanone oxalate [1:1]

The title compound was prepared by the method described in U.S. Pat. No. 3,956,296 (See Example 13 of that patent) as follows: A mixture of 4.75 g (0.0165 mole) of 4-[α,α-bis(p-fluorophenyl)methyl]piperidine, 4.0 g (0.0165 mole) of 3-(p-acetyl-o-methoxyphenoxy)propyl chloride and 1.4 g (0.0165 mole) of sodium bicarbonate in 60 ml of dimethylformamide was heated at 80° C. for about 2 hours. TLC showed no product at this point. The temperature was raised to 100° C. for 1 hr, at which time TLC showed the reaction to be complete. After cooling, the reaction mixture was filtered and the dimethylformamide was removed under reduced pressure. The crude product was dissolved in chloroform and filtered and the filtrate was concentrated under reduced pressure to give 7.7 g (94%) of crude product. The solid was dissolved in benzene and placed on a Florisil ® column. Upon eluting with an acetone-benzene gradient, 5.5 g of product was obtained. The oxalate salt was prepared and upon recrystallization from isopropanol-methanol gave 3.8 g of salt, m.p. 164.5°–166° C.

Analysis: Calculated for $C_{32}H_{35}F_2NO_7$: C, 65.86; H, 6.05; N, 2.40. Found: C, 66.11; H, 6.13; N, 2.39.

EXAMPLE 57

1-[4-[3-[4-[Bis(4-fluorophenyl)methyl]-1-piperidinyl]propoxy]-3-methoxyphenyl]ethanone fumarate [5:6]

A mixture of 58.26 g (0.203 mole) of 4-[bis(4-fluorophenyl)methyl]piperidine, 54.5 g (0.225 mole) of 1-chloro-3-(4-acetyl-2-methoxyphenoxy)propane, 18.7 g (0.223 mole) of sodium bicarbonate and 1.2 g (0.0072 mole) of potassium iodide in 800 ml of 1-butanol was refluxed for 16 hr. The hot reaction mixture was filtered, and the solvent was removed in vacuo from the filtrate. The residue was partitioned between methylene chloride and dilute sodium hydroxide. The methylene chloride solution was dried over magnesium sulfate, and the solvent was removed in vacuo to give an oil. The oil was dissolved in 600 ml of anhydrous ether, and 4.91 g of a solid was collected at room temperature. The ether solution was then treated with a solution of 30.2 g (0.26 mole) of fumaric acid in methanol. Anhydrous ether was added and 99.88 g (77.7%), m.p. 160°–163° C. of title compound was isolated. This was recrystallized from isopropanol-diethyl ether, (2.5 g, 0.0216 mole of additional fumaric acid was added) to give 2 crops of title compound. [Crop I-44.15 g, m.p. 163°–164.5° C.; Crop II-38.75 g, m.p. 161°–163° C.]. An additional 10.00 g (8.786%), m.p. 159°–162° C. of title compound collected from the original ether-methanol filtrate.

Analysis: Calculated for $C_{34.8}H_{37.8}NO_{7.8}F_2$: C, 66.05; H, 6.02; N, 2.21. Found: C, 65.96; H, 6.18; N, 2.16.

EXAMPLE 58

1-[4-[3-[4-[Bis(4-fluorophenyl)methylene]-1-piperidinyl]propoxy]-3-methoxyphenyl]ethanone oxalate [1:1]

The title compound was prepared by the method described in U.S. Pat. No. 3,922,276 (See Ex. 12 of that patent) as follows: A mixture of 4.7 g (0.0165 mole) of 4-[α,α-bis(p-fluorophenyl)methylene]piperidine, 4.0 g (0.0165 mole) of 3-(p-acetyl-o-methoxyphenoxy)propyl chloride and 1.4 g of sodium bicarbonate in 60 ml of dimethylformamide was heated at 100° C. overnight. After cooling, the reaction mixture was filtered and the dimethylformamide was removed at reduced pressure. The residuel oil was dissolved in benzene and placed on a Florisil° column. Elution with a gradient of acetone-benzene gave 5.7 g (70%) of a viscous brown oil. The free base was reacted with oxalic acid to give the oxalate salt, m.p. 169°–170° C. after recrystallization from isopropyl alcohol and drying under nitrogen.

Analysis: Calculated for $C_{32}H_{33}F_2NO_7$: C, 66.08; H, 5.72; N, 2.41. Found: C, 66.01; H, 5.67; N, 2.40.

EXAMPLE 59

1-[4-[3-[4-[(4-Fluorophenyl)phenylmethylene]-1-piperidinyl]propoxy]-3-methoxyphenyl]ethanone oxalate [1:1]

The title compound was prepared by the method described in U.S. Pat. No. 3,922,276 (See Ex. 12 of that patent) as follows: A mixture of 7.1 g (0.027 mole) of 4-[α-(p-fluorophenyl)-α-phenylmethylene]piperidine, 6.5 g (0.027 mole) of 3-(p-acetyl-o-methoxyphenoxy)propyl chloride and 2.3 g. (0.027 mole) of sodium bicarbonate in 100 ml of dimethylformamide was stirred and heated at 100° C. for approximately 8 hours. The mixture was filtered and the dimethylformamide was removed under reduced pressure. The residual oil was dissolved in chloroform and the mixture was filtered. The filtrate was concentrated under vacuum to give 11.5 g. of crude free base (92%). The free base was reacted with oxalic acid to give the oxalate salt, m.p. 143°–145° C. after recrystallization from methylisobutyl ketone.

Analysis: Calculated for $C_{32}H_{34}FNO_7$: C, 68.19; H, 6.08; N, 2.49. Found: C, 68.14; H, 6.12; N, 2.54.

EXAMPLE 60

1-[3-Methoxy-4-[3-[4-[phenyl[3-(trifluoromethyl)phenyl]methylene]-1-piperidinyl]propoxy]phenyl]ethanone oxalate [1:1]

The title compound was prepared by the method described in U.S. Pat. No. 3,922,276 (See Ex. 10 of that patent) as follows: A mixture of 5.0 g (0.0157 mole) of 4-[α-phenyl-α-(m-trifluoromethylphenyl)methylene]-piperidine, 3.82 g (0.0157 mole) of 3-(p-acetyl-o-methoxyphenoxy)propyl chloride and 2.52 g (0.03 mole) of sodium bicarbonate in 75 ml of 1-butanol was stirred and heated at reflux for 17½ hrs. The mixture was cooled and filtered, and the filtrate was concentrated under reduced pressure. The glassy residue obtained weighed 4.25 g (52%) and was dissolved in benzene and placed on a Florisil ® column. Using an acetone-benzene gradient elution, product was obtained as a glassy residue. This residue was dissolved in ether and the oxalate salt was obtained. The salt has a glassy appearance, m.p. 120°–125° C.

Analysis: Calculated for $C_{33}H_{34}F_3NO_7$: C, 64.59; H, 5.58; N, 2.28. Found: C, 64.34; H, 5.72; N, 2.04.

EXAMPLE 61

1-[4-[3-[4(Cyclohexylphenylmethylene)-1-piperidinyl]-propoxy]-3-methoxyphenyl]ethanone oxalate [1:1]

The free base of the title compound was obtained as in Example 1 of U.S. Pat. No. 3,922,276 by reacting 4-[(α-cyclohexyl-α-phenyl)methylene]piperidine with 3-(p-acetyl-o-methoxyphenoxy)propyl chloride in a mixture with sodium bicarbonate in dimethylformamide and converted to the oxalate salt, m.p. 184°–185° C.

Analysis: Calculated for $C_{32}H_{41}NO_7$: C, 69.67; H, 7.49; N, 2.54. Found: C, 69.83; H, 7.58; N, 2.56.

EXAMPLE 62

1-[4-[3-[4-(Cyclohexylphenylmethyl)-1-piperidinyl]-propoxy]-3-methoxyphenyl]ethanone oxalate hydrate [1:1:0.5]

A mixture of 5.2 g (0.02 mole) of 4-[(α-cyclohexyl-αo-phenyl)methyl]piperidine, 4.9 g (0.02 mole) of 3-(p-acetyl-o-methoxyphenoxy)propyl chloride and 1.7 g (0.02 mole) of sodium bicarbonate in 100 ml of dimethylformamide was stirred and heated at 100° C. for 4 hrs. The reaction mixture was cooled, filtered, and the dimethylformamide was removed under reduced pressure. The residual material was dissolved in benzene and placed on a Florisil ® column. Elution using an acetone-benzene gradient gave 7.0 g (74.5%) of free base of the title compound. The oxalate salt was prepared and recrystallized from isopropanol, m.p. 155°–160° C.

Analysis: Calculated for $C_{64}H_{88}N_2O_{15}$: C, 68.31; H, 7.88; N, 2.49. Found: C, 68.60; H, 7.78; N, 2.42.

The free base of the title compound was obtained by reacting 4-[(α-cyclohexyl-α-phenyl)methyl]piperidine and 3-(p-acetyl-o-methoxyphenoxy)propyl chloride in a mixture with sodium bicarbonate, isolated and reacted with oxalic acid. The oxalate salt was recrystallized from isopropanol, m.p. 155°–160° C.

EXAMPLE 63

4-[3-[4-[Bis(4-fluorophenyl)methylene]-1-piperidinyl]-propoxy]-alpha-methylbenzenemethanol oxalate [1:1]

A solution of 1-[4-[3-[4-[bis(4-fluorophenyl)methylene]-1-piperidinyl]propoxy]phenyl]ethanone, 3.56 g (0.0077 mole) and sodium borohydride, 1.51 g (0.04 mole) was stirred 6 hrs at room temperature. The reaction mixture was stripped to dryness and partitioned between chloroform-water and chloroform-5% sodium hydroxide. Removal of chloroform gave an oil which was converted to the oxalate salt. Recrystallization from methanol-diethyl ether gave 2.67 g (62.1%) of white crystalline product, m.p 142°–145° C.

Analysis: Calculated for $C_{31}H_{33}NO_6F_2$: C, 67.26; H, 6.01; N, 2.53. Found: C, 67.17; H, 5.92; N, 2.47.

EXAMPLE 64

4-[3-[4-[Bis(4-fluorophenyl)methyl]-1-piperidinyl]-propoxy]-3-methoxy-α-methylbenzenemethanol

Sodium borohydride (3.0 g, 0.079 mole) was added to 250 ml of 95% ethanol. To the mixture was added 4.40 g (0.00885 mole) of 1-[3-(p-acetyl-o-methoxyphenoxy)-propyl]-4-[α,α-bis(p-fluorophenyl)methyl]piperidine in 100 ml of 95% ethanol over 15 minutes. The resulting solution was stirred 2½ hr at room temperature. The reaction mixture was stripped to dryness and partitioned between chloroform and 5% sodium hydroxide. The organic layer was back extracted with 5% sodium hydroxide and water; removal of chloroform gave an oil. The oil formed a white solid in diethyl ether. The white solid was filtered off and recrystallized from methylene chloride-diethyl ether. This furnished 2.16 g (49.2%) of white solid, m.p. 132°–135° C.

Analysis: Calculated for $C_{30}H_{35}NO_3F_2$: C, 72.72; H, 7.12; N, 2.83. Found: C, 72.28; H, 7.21; N, 2.52.

EXAMPLE 65

1-[4-[3-[4-(Diphenylmethyl)-1-piperidinyl]propoxy]-3-methoxyphenyl]ethanone oxalate [1:1]

A mixture of 5.0 g (0.02 mole) of 4-(α-phenylbenzyl)-piperidine, 4.85 g (0.02 mole) of 3-(p-acetyl-o-methoxyphenoxy)propyl chloride, and 3.4 g (0.04 mole) of sodium bicarbonate in 100 ml of dimethylformamide was heated at 100° C. for about 3 hrs. The reaction mixture was cooled, filtered and the filtrate was concentrated under reduced pressure. The residual oil was dissolved in chloroform and the chloroform was filtered to remove insolubles. The filtrate was concentrated under reduced pressure to give 8.6 g of a red oil (94.5%). The oil was dissolved in a mixture of 4:1 ether-isopropanol and treated with 2.3 g of oxalic acid dihydrate. The oxalate salt crystallized upon standing and trituration in ether gave 8.4 g of salt melting at 149°–155° C. Recrystallization from isobutyl methyl ketone gave 7.0 g of the salt, m.p. 153°–155° C. (See Ex. 11, U.S. Pat. No. 3,956,296).

Analysis: Calculated for $C_{32}H_{37}NO_7$: C, 70.18; H, 6.81; N, 2.56. Found: C, 70.00; H, 6.76; N, 2.56.

EXAMPLE 66

1-[4-[3-[4-[Bis(4-fluorophenyl)hydroxymethyl]-1-piperidinyl]propoxy]-3-methoxyphenyl]ethanone

A mixture of 5.0 g (0.0165 mole) of α,α-bis(p-fluorophenyl)-4-piperidinemethanol, 4.0 g (0.0165 mole) of 3-(p-acetyl-o-methoxyphenoxy)propyl chloride and 1.4 g (0.0165 mole) of sodium bicarbonate in 60 ml of dimethylformamide was stirred and heated at 80° C. for two hours. The temperature was raised to 100° C. for one hour. After cooling, the reaction mixture was filtered and the dimethylformamide was removed at reduced pressure. The residual oil which crystallized on standing in ether was dissolved in benzene and placed on a Florisil ® column. Using a gradient elution of acetone-benzene, 1.8 g (21.4%) of product was obtained from the column, m.p. 141.5°–143° C. (See Ex. 12, U.S. Pat. No. 3,956,296).

Analysis: Calculated for $C_{30}H_{33}F_2NO_4$: C, 70.71; H, 6.53; N, 2.75. Found: C, 70.49; H, 6.58; N, 2.59.

EXAMPLE 67

1-[4-[3-[4-[(4-Fluorophenyl)hydroxyphenylmethyl]-1-piperidinyl]propoxy]-3-methoxyphenyl]ethanone

A mixture of 6.5 g (0.023 mole) of α-(p-fluorophenyl)-α-phenyl-4-piperidinemethanol, 5.5 g (0.023 mole) of 3-(p-acetyl-o-methoxyphenoxy)propyl chloride and 1.92 g (0.023 mole) of sodium bicarbonate in 80 ml of dimethylformamide was heated at 100°–110° C. for 2 hrs. The reaction mixture was cooled and filtered and the dimethylformamide was removed at reduced pressure. The residual oil was dissolved in chloroform and filtered. The chloroform was removed at reduced pressure. The solid residue which remained weighed 8.6 g (77%) and was recrystallized from ethanol to give 3.1 g of material melting at 147°–148° C. A sample was dried over refluxing toluene and submitted for analysis. (See Ex. 14, U.S. Pat. No. 3,956,296).

Analysis: Calculated for $C_{30}H_{34}NO_4F$: C, 73.30; H, 6.97; N, 2.85. Found: C, 73.15; H, 7.05; N, 2.77.

EXAMPLE 68

1-[4-[3-[4-(Diphenylhydroxymethyl)-1-piperidinyl]-propoxy]-3-methoxyphenyl]ethanone oxalate [1:1]

A mixture of 5.2 g (0.0194 mole) of α,α-diphenyl-4-piperidinemethanol, 4.7 g (0.0194 mole) of 3-(p-acetyl-o-methoxyphenoxy)propyl chloride and 1.6 g (0.0194 mole) of sodium bicarbonate in 60 ml of dimethylformamide was stirred at 100° C. for 3 hrs. After cooling, the reaction mixture was filtered and the dimethylformamide was removed under reduced pressure. The residual oil weighed 8.3 g (90%). Some of the product crystallized upon trituration in anhydrous ether and was collected by filtration. The filtrate was evaporated to dryness and the residue was dissolved in hot benzene-isooctane. Upon cooling, the crystalline product was obtained. A total yield of 6.3 g of solid product was obtained. The solid free base was converted to the oxalate salt. Recrystallization from isobutyl methyl ketone gave the off-white solid melting at 174°–176° C. (See Ex. 15, U.S. Pat. No. 3,956,296).

Analysis: Calculated for $C_{32}H_{37}NO_8$: C, 68.19; H, 6.62; N, 2.49. Found: C, 68.34; H, 6.75; N, 2.42.

EXAMPLE 69

1-[4-[3-[4-[Hydroxyphenyl[-3-(trifluoromethyl)phenyl]-methyl]-1-piperidinyl]propoxy]-3-methoxyphenyl]ethanone hydrochloride hydrate [1:1:0.5]

A mixture of 7.0 g (0.021 mole) of α-phenyl-α-(m-trifluoromethylphenyl)-4-piperidinemethanol, 5.1 g (0.021 mole) of 3-(p-acetyl-o-methoxyphenoxy)propyl chloride and 3.0 g (0.036 mole) of sodium bicarbonate in 125 ml of dry dimethylformamide was stirred and heated at 90°–95° C. for 5 hours. The mixture was cooled and filtered. An excess of water was added to the reaction mixture. The mixture was extracted several times with benzene and the collected extracts were dried over anhydrous sodium sulfate. The mixture was filtered and the filtrate was concentrated under reduced pressure. The crude solid which was obtained was dissolved in benzene and placed on a Florisil® column. Elution using an acetone-benzene gradient gave a gummy solid. The gum was dissolved in ether and the hydrochloride salt was prepared. The hydrochloride salt weighed 3.1 g (25%) and became a clear melt at 95° C. (See Ex. 16, U.S. Pat. No. 3,956,296).

Analysis: Calculated for $C_{62}H_{72}Cl_2N_2O_9$: C, 63.42; H, 6.18; N, 2.39. Found: C, 63.68; H, 6.03; N, 2.33.

EXAMPLE 70

1-[4-[3-[4-(Cyclohexylhydroxyphenylmethyl)-1-piperidinyl]propoxy]-3-methoxyphenyl]ethanone hydrochloride [1:1]

A mixture of 3.9 g (0.143 mole) of α-cyclohexyl-α-phenyl-4-piperidinemethanol, 3.5 g (0.143 mole) of 3-(p-acetyl-o-methoxyphenoxy)propyl chloride and 2.35 g (0.28 mole) of sodium bicarbonate in 100 ml of dimethylformamide was heated at 100° C. for 4 hrs. After cooling, the reaction mixture was diluted with about 600 ml of water and extracted with benzene. The collected benzene extracts were washed with water and dried over anhydrous magnesium sulfate. The mixture was filtered, and the filtrate was concentrated under reduced pressure. A crude solid weighing 5.1 g (74.5%) was obtained. The solid was dissolved in ether, and the ether solution was treated with an excess of ethereal hydrogen chloride. The hydrochloride salt obtained was recrystallized from isobutyl methyl ketone to give 4.0 g of the salt, m.p. 152°-155° C. (See Ex. 17, U.S. Pat. No. 3,956,296).

Analysis: Calculated for $C_{30}H_{42}ClNO_4$: C, 69.82; H, 8.20; N, 2.71. Found: C, 69.50; H, 8.31; N, 2.62.

EXAMPLE 71

1-[4-[2-[4-[Bis(4-fluorophenyl)hydroxymethyl]-1-piperidinyl]ethoxy]-3-methoxyphenyl]ethanone Following the procedure of Example 1 and utilizing potassium iodide catalyst, a mixture of 3.0 g (0.01 mole) of α, α-bis(p-fluorophenyl)-4-piperidinemethanol, 2.3 g (0.01 mole) of 1-[4-(2-chloroethoxy)-3-methoxyphenyl]ethanone and sodium carbonate in butanol, the title compound was prepared in 22% yield, m.p. 131°-135° C. after recrystallization from isopropyl alcohol.

Analysis: Calculated for $C_{29}H_{31}F_2NO_4$: C, 70.29; H, 6.31; N, 2.83. Found: C, 70.00; H, 6.39; N, 2.60.

EXAMPLE 72

1-[4-[4-[4-[Bis(4-fluorophenyl)hydroxymethyl]-1-piperidinyl]butoxy]-3-methoxyphenyl]ethanone This compound was prepared according to the procedure used to synthesize the compound of Example 35. A mixture of 3.0 g (0.01 mole) of α,α-bis(p-fluorophenyl)-4-piperidinemethanol, 3.0 g (0.01 mole) of 1-[4-(4-bromobutoxy)-3-methoxyphenyl]ethanone, 5.3 g (0.05 mole of anhydrous sodium carbonate and 0.3 g of potassium iodide in 100 ml of dimethylformamide gave, after purification by column chromatography on Florisil® (acetone-benzene). 0.8 g (15%) of off-white powder, m.p. 104°-105° C. after recrystallization from 2-propanol-isopropyl ether.

Analysis: Calculated for $C_{31}H_{35}F_2NO$: C, 71.11; H, 6.74; N, 2.68. Found: C, 70.84; H, 6.71; N, 2.65.

EXAMPLE 73

1-[4-[5-[4-[Bis(4-fluorophenyl)hydroxymethyl]-1-piperidinyl]pentoxy]-3-methoxyphenyl]ethanone Following the procedurre of Example 1 and utilizing potassium iodide catalyst, a mixture of 3.0 g (0.01 mole) of α,α-bis(p-fluorophenyl)-4-piperidinemethanol, 2.7 g (0.01 mole) of 1-[4-(5-chloropentoxy)-3-methoxyphenyl]ethanone and sodium carbonate in butanol, the title compound was prepared in 65% yield as white solid after recrystallization from isopropyl alcohol, m.p. 117.5°-118.5° C.

Analysis: Calculated for $C_{32}H_{37}F_2NO_4$: C, 71.49; H, 6.94; N, 2.61. Found: C, 71.51; H, 7.06; N, 2.50.

EXAMPLE 74

1-[4-[2-[4-[Bis(4-fluorophenyl)methyl]-1-piperidinyl]ethoxy]-3-methoxyphenyl]ethanone A mixture of 4-[bis(4-fluorophenyl)methyl]piperidine, 4.88 g (0.017 mole), 1-[4-(2-chloroethoxy)-3-methoxyphenyl]ethanone, 3.86 g (0.017 mole), and potassium carbonate, 5.53 g (0.04 mole) was heated overnight at gentle reflux in 350 ml of 1-butanol containing potassium iodide (0.3 g). The reaction mixture was filtered and stripped to dryness. The dark brown oil obtained was dissolved in chloroform and extracted with 1N sulfuric acid and 5% sodium hydroxide. The chloroform layer was dried, filtered, and solvent removed. This furnished a brown oil which was subjected to flash chromatography on silica gel using hexane-ethyl acetate for elution. A white solid was obtained by evaporating the fractions containing the product. The solid was extracted with diethyl ether and the mixture was placed in the freezer overnight. A white solid was obtained which was dried at 80° C. in vacuo overnight. A yield of 2.2 g (27%) of white crystalline solid, m.p. 129°-131° C. was obtained.

Analysis: Calculated for $C_{29}H_{31}NO_3F_2$: C, 72.63; H, 6.52; N, 2.92. Found: C, 72.52; H, 6.45; N, 2.87.

EXAMPLE 75

1-[4-[3-[4-[Bis(4-chlorophenyl)methylene]-1-piperidinyl]propoxy]-3-methoxyphenyl]ethanone A mixture of 3.96 g (0.01305 mole) of 4-[bis(4-chlorophenyl)methylene]piperidine, 3.16 g (0.013 mole) of 1-[4-(3-chloropropoxy)-3-methoxyphenyl]ethanone in 300 ml of 1-butanol containing 0.3 g of potassium iodide was heated overnight at gentle reflux. The reaction mixture was stripped to dryness and partitioned between chloroform-water and chloroform-5% sodium hydroxide. Removal of chloroform gave an oil which crystallized from isopropyl alcohol. The solid was again crystallized from isopropyl alcohol to give 4.16 g (61%) of light yellow solid, m.p. 143°-144° C.

Analysis: Calculated for $C_{30}H_{31}NO_3Cl_2$: C, 68.70; H, 5.96; N, 2.67. Found: C, 69.11; H, 6.02; N, 2.55.

EXAMPLE 76

1-[4-[3-[4-[(4-Fluorophenyl)phenylmethyl]-1-piperidinyl]propoxy]-3-methoxyphenyl]ethanone oxalate [1:1]

A solution of 4.42 g (0.0164 mole) of 4-[(4-fluorophenyl)phenylmethyl]piperidine and 4.11 g (0.0170 mole) of 1-[4-(3-chloropropoxy)-3-methoxyphenyl]e- thanone, 0.01 g of potassium iodide and 1-butanol was refluxed for 18 hr. The solvent was removed in vacuo, and the residue was partitioned between methylene chloride and dilute sodium hydroxide. The solvent was removed in vacuo to give an oil. A solution of the oil in methanol was treated with an equivalent of oxalic acid, ethyl ether was added, and 6.39 g (68.9%) of white crystalline solid, m.p. 161°–163° C. was obtained.

Analysis: Calculated for $C_{32}H_{36}NO_7F$: C, 67.95; H, 6.42; N, 2.48. Found: C, 67.92; H, 6.42; N, 2.44.

EXAMPLE 77

1-[4-[3-[4-[Bis(4-methoxyphenyl)methyl]-1-piperidinyl]-propoxy]-3-methoxyphenyl]ethanone oxalate [1:1]

A mixture of 7.78 g (0.025 mole) of 4-[bis(4-methoxyphenyl)methyl]piperidine, 6.05 g (0.025 mole) of 1-[4-(3-chloropropoxy)-3-methoxyphenyl]ethanone, and potassium carbonate (5.53 g, 0.04 mole) in 300 ml of 1-butanol containing potassium iodide (0.3 g) was refluxed overnight. The reaction mixture was stripped to dryness and the residue was partitioned between chloroform and water; removal of chloroform in vacuo gave a dark brown oil. The oil was subjected to column chromatography on silica gel using a gradient elution composed of methanol and ethyl acetate. The corresponding fractions from the column were combined and reacted with oxalic acid. Recrystallization of the salt from methanol-diethyl ether gave 4.16 g (27.4%) of white solid, m.p. 163.5°–165° C.

Analysis: Calculated for $C_{34}H_{41}NO_9$: C, 67.20; H, 6.80; N, 2.31. Found: C, 66.76; H, 6.84; N, 2.26.

EXAMPLE 78

1-[4-[3-4-[Bis(4-methylphenyl)methyl]-1-piperidinyl]-propoxy]-3-methoxyphenyl]ethanone A mixture of 5.10 g (0.018 mole) of 4-[bis(4-methylphenyl)methyl]piperidine and 4.42 g (0.018 mole) of 1-[4-(3-chloropropoxy)-3-methylphenyl]ethanone in 350 ml of 1-butanol was heated overnight at gentle reflux with potassium carbonate (5.53 g, 0.04 mole) and potassium iodide (0.3 g). The reaction mixture was stripped to dryness and the resulting residue was partitioned between chloroform-5% sodium hydroxide and chloroform-water. Removal of chloroform gave a dark brown oil. The oil was subjected to column chromatography on a silica gel column with a gradient elution series of hexane-ethyl acetate and ethyl acetate-dimethoxy-ethane. The proper fractions from the column were combined. This resulted in 2.60 g (29.7%) of oil (after drying in vacuo at 80° C. overnight).

Analysis: Calculated for $C_{32}H_{39}NO_3$: C, 79.14; H, 8.09; N, 2.88. Found: C, 78.70; H, 8.08; N, 2.80.

$^1$H NMR (CDCl$_3$): 7.5 $\sigma$ (multiplet, protons on ring next to ketone, 2H) 6.7–7.6 (multiplet, aromatic proton, 9H), 4.0 (triplet, methylene adjacent to ether oxygen, 2H), 3.8 (singlet, OCH$_3$, 3H), 3.3 (doublet, methine next to rings, 1H), 2.5 (singlet, methyl of ketone, 3H), 2.2 (singlet, methyl groups attached to aromatic rings, 6H), 1.0–3.0 (multiplet, remaining aliphatic protons, 13H).

EXAMPLE 79

1-[4-[4-[4[Bis(4-fluorophenyl)methyl]-1-piperidinyl]-butoxy]-3-methoxyphenyl]ethanone A mixture of 6.15 g (0.021 mole) of 4-[bis(4-fluorophenyl)methyl]piperidine and 6.45 g (0.02 mole) of 1-[4-(4-bromobutoxy)-3-methoxyphenyl]ethanone in 350 ml of acetonitrile was stirred overnight at room temperature with potassium carbonate, 5.53 g (0.04 mole) and potassium iodide (0.3 g). The mixture was then heated five hours at reflux. The reaction mixture was stripped to dryness on a rotary evaporator, and the residue was partitioned between chloroform-5% sodium hydroxide and chloroform-water. Removal of chloroform gave a dark brown oil. The oil was subjected to chromatography on a silica gel column and eluted with a hexane-ethyl acetate-dimethoxyethane series. Fractions from the column were combined and solvent removed by pumping in vacuo overnight at 80° C. This provided 3.34 g (31.3%) of brown oil.

Analysis: Calculated for $C_{31}H_{35}NO_3F_2$: C, 73.35; H, 6.95; N, 2.76. Found: C, 72.34; H, 6.92; N, 2.70.

NMR analysis was obtained as follows:

$^1$H NMR (CDCl$_3$): 6.8–7.6 $\sigma$ (multiplet, aromatics, 11H), 4.1 (triplet methylene next to ether linkage, 2H), 3.4–3.6 (doublet, methine attached to two fluorophenyl rings, 1H), 3.8 (singlet, OCH$_3$, 3H), 2.5 (singlet, COCH$_3$, 3H), 1.1–3.0 (multiplet, remaining aliphatics, 15H).

EXAMPLE 80

4-[3-[4-[Bis(4-fluorophenyl)hydroxymethyl]-1-piperidinyl]propoxyl-3-methoxybenzoic acid methyl ester Following the procedure of Example 1 and utilizing potassium iodide catalyst and substituting dimethylformamide for butanol, a mixture of 5.4 g (0.021 mole) of 4-(3-chloropropoxy)-3-methoxybenzoic acid methyl ester, 6.0 g (0.02 mole) of [$\alpha,\alpha$-bis(p-fluorophenyl)]-4-piperidinemethanol, 7.4 g (0.07 mole) of anhydrous sodium carbonate and 0.3 g of potassium iodide in 150 ml of dimethylformamide was reacted to give 5.7 g (53%) of white solid, m.p. 131°–132.5° C. after recrystallization from isopropyl alcohol.

Analysis: Calculated for $C_{30}H_{33}F_2NO_5$: C, 68.56; H, 6.33; N, 2.67. Found: C, 68.23; H, 6.35; N, 2.60.

EXAMPLE 81

$\alpha,\alpha$-[Bis(4-fluorophenyl)]-1-[3-[4-(methylthio)phenoxy]propyl]-4-piperidinemethanol Following the procedure of Example 1, a mixture of 3.0 g (0.01 mole) of [$\alpha,\alpha$-bis(p-fluorophenyl)]-4-piperidinemethanol, 2.2 g (0.01 mole) of 1-chloro-3-(4-methylthiophenoxy)propane, 5.3 g (0.05 mole) of anhydrous sodium carbonate and 0.3 g of potassium iodide in 100 ml of 1-butanol was reacted to give 2.3 g (48%) of white powder, m.p. 113°–115° C. after recrystallization from isopropyl ether.

Analysis: Calculated for $C_{28}H_{31}F_2NO_2S$: C, 69.54; H, 6.46; N, 2.90. Found: C, 69.57; H, 6.51; N, 2.85.

EXAMPLE 82

$\alpha,\alpha$-[Bis(4-fluorophenyl)]-1-[3-[4-(methylsulfonyl)-phenoxy]propyl]-4-piperidinemethanol fumarate [1:1]

Following the procedure of Example 1, a mixture of 3.0 g (0.01 mole) of [$\alpha,\alpha$-bis(p-fluorophenyl)]-4-piperidinemethanol, 2.5 g (0.01 mole) of 1-(3-chloropropoxy)-4-(methylsulfonyl)benzene, 5.3 g (0.05 mole) of anhydrous sodium carbonate and 0.3 g of potassium iodide in 100 ml of 1-butanol was reacted to give a brown gum as residue. The gummy residue was reacted with fumaric acid and the fumarate salt obtained was recrystallized from acetonitrile to give 3.0 g (48%) of white solid, m.p. 176°–178° C.

Analysis: Calculated for $C_{32}H_{35}F_2NO_8S$: C, 60.85; H, 5.59; N, 2.22. Found: C, 60.72; H, 5.54; N, 2.20.

EXAMPLE 83

4-[3-[4-[Bis(4-fluorophenyl)hydroxymethyl]-1-piperidinyl]propoxy]-3-methoxybenzeneacetic acid ethyl ester hydrochloride Following the procedure of Example 45, [α,α-bis(p-fluorophenyl)]-4-piperidinemethanol and 4-(3-chloropropoxy)-3-methoxybenzeneacetic acid, ethyl ester are reacted and the hydrochloride salt is prepared.

EXAMPLE 84

4-[3-[4-[Bis(4-fluorophenyl)hydroxymethyl]-1-piperidinyl]ethoxy]benzoic acid ethyl ester hydrochloride Following the procedure of Example 45, α,α-bis(p-fluorophenyl)-4-piperidinemethanol and 4-(2-chloroethoxy)benzoic acid ethyl ester are reacted and the hydrochloride salt is prepared.

EXAMPLE 85

4-[3-[4-[Bis(4-fluorophenyl)hydroxymethyl]-1-piperidinyl]propoxy]-3-methoxybenzeneacetic acid sodium salt hemihydrate This compound was prepared according to the procedure of Example 1. A mixture of 3.0 g (0.01 mole) of [α,α-bis(p-fluorophenyl)]-4-piperidinemethanol, 2.9 g (0.01 mole) of 4-(3-chloropropoxy)-3-methoxybenzeneacetic acid ethyl ester, 5.3 g (0.05 mole) of anhydrous sodium carbonate and 0.3 g of potassium iodide in 150 ml of acetonitrile gave the ester as a gum. The gum was converted to the hydrochloride with ethereal hydrogen chloride to give a white solid. The solid could not be recrystallized so it was partitioned between methylene chloride and a 5% sodium hydroxide solution. An emulsion resulted which was let stand until the layers separated. During this time a solid precipitated. The mixture was filtered. The filter cake was recrystallized from ethyl acetate to yield 0.7 g (13%) of fluffy, white solid, m.p. 102°–112° C.

Analysis: Calculated for $C_{30}H_{32}F_2NNaO_5.0.5\ H_2O$: C, 64.74; H, 5.98; N, 2.52. Found: C, 64.50; H, 5.97; N, 2.39.

EXAMPLE 86

7-[3-[4-[Bis(4-fluorophenyl)hydroxymethyl]-1-piperidinyl]propoxy]-2H-1-benzopyran-2-one This compound was prepared according to the procedure of Example 1. A mixture of 3.0 g (0.01 mole) of [α,α-bis(p-fluorophenyl)]-4-piperidinemethanol, 2.4 g (0.01 mole of 7-(3-chloropropoxy)-2H-1-benzopyran-2-one, 5.3 g (0.05 mole) of anhydrous sodium carbonate and 0.3 g of potassium iodide in 100 ml of 1-butanol gave 3.6 g (71%) of pale yellow crystals, m.p. 99°–120° C. with decomposition. Recrystallizing solvent used was 2-propanol.

Analysis: Calculated for $C_{30}H_{29}F_2NO_4$: C, 71.27; H, 5.78; N, 2.77. Found: C, 71.02; H, 5.89; N, 2.63.

EXAMPLE 87

2-[3-[4-[Bis(4-fluorophenyl)hydroxymethyl]-1-piperidinyl]propoxy]benzoic acid ethyl ester fumarate [4:3]

This compound is prepared according to the procedure of Example 1. A mixture of 3.0 g (0.01 mole) of [α,α-bis(p-fluorophenyl)]-4-piperidinemethanol, 2.4 g (0.01 mole) of 2-(3-chloropropoxy)benzoic acid ethyl ester, 5.3 g (0.05 mole) of anhydrous sodium carbonate and 0.3 g of potassium iodide in 100 ml of dimethylformamide gave 5.7 g of gum as residue. The gum was purified by column chromatography on 100 g of silica gel. Fractions eluted with 35% acetone in benzene were combined and concentrated to give 3.0 g of pale yellow gum as residue. The gum was converted to the fumaric acid salt and the solid was recrystallized twice from 2-propanol to yield 2.0 g (32%) of white solid, m.p. 138°–141° C.

Analysis: Calculated for $C_{33}H_{36}F_2NO_7$: C, 66.43; H, 6.08; N, 2.35. Found: C, 66.25; H, 6.08; N, 2.27.

EXAMPLE 88

2-[3-[4-[Bis(4-fluorophenyl)methyl]-1-piperidinyl]propoxy]benzoic acid ethyl ester A mixture of 32.79 g (0.116 mole) of 4-[bis(4-fluorophenyl)methyl]piperidine, 27.04 g (0.114 mole) of 2-(3-chloropropoxy)benzoic acid ethyl ester, and potassium carbonate, 19.40 g (0.140 mole) was heated overnight at reflux in 500 ml of diethoxyethane containing potassium iodide (0.4 g). The reaction was filtered and stripped to dryness. The residue obtained was dissolved in chloroform and extracted with 5% sodium hydroxide, sodium sulfite, and water. The chloroform layer was dried (anhydrous sodium sulfate), filtered, and solvent removed to furnish a dark brown oil (56.20 g). The oil was subjected to flash chromatography on an 83.5 g silica gel column (with ethyl acetate). Fractions were combined with similar purity. One sample of 6.49 g (56.5%) was dried in vacuo at 80° C. overnight and analyzed.

$^1$H NMR (CDCl$_3$): 7.8δ (m, 1, aromatic proton ortho to ester) 7.0δ (m, 11, aromatic), 4.3δ (q, 2, C—O—CH$_2$), 4.1δ (t, 2, —OCH$_2$), 3.5δ (d, 1, methine), 1,3δ (t, 3, CH$_3$), 1.7–3.0δ (m, 13, aliphatic).

Analysis: Calculated for $C_{30}H_{33}NO_3NO_3F_2$: C, 73.00; H, 6.74; N, 2.84. Found: C, 72.98; H, 6.70; N, 2.93.

EXAMPLE 89

1-[4-[5-[4-[Bis(4-fluorophenyl)methyl]-1-piperidinyl]pentoxy]-3-methoxyphenyl]ethanone hemihydrate A mixture of 6.03 g (0.021 mole) of 4-[bis(4-fluorophenyl)methyl]piperidine, 5.69 g (0.021 mole) of 1-[4-(5-chloropentoxy)-3-methoxyphenyl]ethanone, and potassium carbonate (5.53 g, 0.04 mole) was heated overnight at gentle reflux in 350 ml of 1-butanol containing potassium iodide (0.2 g). The reaction mixture was cooled at room temperature, filtered, and striped to dryness. The residue obtained was dissolved in chloroform and extracted several times with water. The chloroform layer was dried (sodium sulfate), filtered, and solvent removed to give a brown oil. This oil was subjected to flsh chromatography on silica gel using ethyl acetate and 2% methanol-ethyl acetate for elution. Fractions of similar purity were combined and solvent removed. The sample was dried in vacuo at 70° C. overnight after being exposed to the atmosphere for 24 hours. A yield of 2.7 g (24.6%) of brown oil was obtained.

---

$^1$H NMR (CDCl$_3$): 6.8–7.6δ(m, 11, aromatic),
4.1δ(t, 2, —OCH$_3$), 3.9δ(s, 3, OCH$_3$)
3.4–3.6δ(d, 1, methine of difluorophenyl group), -continued

| | |
|---|---|
| 2.5δ(s, 3, —C—CH$_3$), <br> ‖ <br> O | 1–3.0δ(m, 18, aliphatics and 0.5 H$_2$O) |

Analysis: Calculated for C$_{32}$H$_{38}$NO$_{3.5}$F$_2$: C, 72.43; H, 7.22; N, 2.64. Found: C, 72.75; H, 7.23; N, 2.57.

EXAMPLE 90

4-[3-[4-[Bis(4-fluorophenyl)methyl]-1-piperidinyl]-propoxy]benzamide fumarate [2:3]

A mixture of 6.10 g (0.02125 mole) of 4-[bis(4-fluorophenyl)methyl]piperidine and 4.53 g (0.02125 mole) of 4-(3-chloropropoxy)benzamide in 350 ml of 1-butanol containing potassium carbonate (5.53 g, 0.02125 mole) and potassium iodide (0.2 g) was heated overnight at gentle reflux. The reaction was filtered and stripped to dryness. The residue obtained was dissolved in chloroform and extracted with water. The chloroform layer was dried, filtered, and solvent removed to give an oil. This material was converted to the fumarate salt and recrystallized from methanoldiethyl ether. The white crystalline solid obtained was dried in vacuo overnight at 65° C. A yield of 5.47 g (40.3%) of white crystalline product was obtained, m.p. 193°–194° C.

Analysis: Calculated for C$_{34}$H$_{36}$N$_2$O$_8$F$_2$: C, 63.94; H, 5.68; N, 4.39. Found: C, 64.03; H, 5.73; N, 4.37.

EXAMPLE 91

4[Bis(4-fluorophenyl)methyl]-1-[3-[4-(methylsulfonyl)-phenoxy]propyl]piperidine oxalate [1:1]

A mixture of 6.02 g (0.021 mole) of 4-[bis(4-fluorophenyl)methyl]piperidine and 5.22 g (0.021 mole) of 1-(3-chloropropoxy)-4-(methylsulfonyl)benzene in 350 ml of 1-butanol containing potassium carbonate (5.53 g, 0.04 mole) and potassium iodide (0.2 g) was heated overnight at gentle reflux. The reaction was filtered and stripped to dryness. The residue obtained was dissolved in chloroform and extracted with water. The chloroform layer was dried, filtered, and solvent removed to give an oil. The dark brown oil was converted to the oxalate salt and recrystallized from methanol-diethyl ether to give a white solid. This material was dried in vacuo overnight at 65° C. A yield of 6.21 g (50.1%) of white crystalline solid, m.p. 202°–204° C. was obtained.

Analysis: Calculated for C$_{30}$H$_{33}$NSO$_7$F$_2$: C, 61.11; H, 5.64; N, 2.38. Found: C, 60.99; H, 5.64; N, 2.36.

EXAMPLE 92

1-[4-[6-[4-[Bis(4-fluorophenyl)hydroxymethyl]-1-piperidinyl]hexyloxy]-3-methoxyphenyl]ethanone Following the procedure of Example 1 and utilizing potassium iodide catalyst, a mixture of [α,α-bis(p-fluorophenyl)]-4-piperidinemethanol and 1-[4-(6-chlorohexoxy)-3-methoxyphenyl]ethanone and sodium carbonate in butanol, the title compound is prepared.

EXAMPLE 93

1-[4-[3-[4-[Bis(4-fluorophenyl)hydroxymethyl]-1-piperidinyl]propoxy]-2-methoxyphenyl]ethanone Following the procedure of Examples 1 and 66, [α,α-bis (p-fluorophenyl)]-4-piperidinemethanol and 3-(p-acetyl-m-methoxyphenoxy)propyl chloride are reacted to give the title compound.

EXAMPLE 94

α,α-Bis(4-fluorophenyl)-1-[3-(2-hydroxyphenoxy)-propyl]-4-piperidinemethanol

Following the procedure of Example 2 and using potassium iodide catalyst, [α,α-bis(p-fluorophenyl)]-4-piperidinemethanol and 2-(3-chloropropoxy)-1-benzyloxybenzene are reacted to give 1-[3-(2-benzyloxyphenoxy)propyl]-α,α-bis(4-fluorophenyl)-4-piperidinemethanol which is reacted with hydrogen over palladium on carbon catalyst to give the title compound.

EXAMPLE 95

α,α-[Bis(4-fluorophenyl)]-1-[3-[4-(methylsulfinyl)-phenoxy]propyl]-4-piperidine methanol fumarate Following the procedure of Examples 1 and 82, [α,α-bis(p-fluorophenyl)]-4-piperidinemethanol and 1-(3-chloropropoxy)-4-(methylsulfinyl)benzene are reacted to give the free base of the title compound which is then reacted with fumaric acid to give the title compound.

EXAMPLE 96

4-[3-[4-[Bis(4-fluorophenyl)hydroxymethyl]-1-piperidinyl]propoxy]benzenesulfonamide hydrochloride [1:1]

This compound was prepared according to the procedure of Example 1. A mixture of 3.0 g (0.01 mole) of [α,α-bis(p-fluorophenyl)]-4-piperidinemethanol, 2.5 g (0.01 mole) of 4-(3-chloropropoxy)benzenesulfonamide, 5.3 g (0.05 mole) of anhydrous sodium carbonate and 0.3 g of potassium iodide in 100 ml of 1-butanol gave a gum as residue. The gum was converted to the hydrochloride with ethereal hydrogen chloride and the solid was recrystallized from absolute ethanol to yield 3.5 g (64%) of white solid, m.p. 152°–175° C.

Analysis: Calculated for C$_{27}$H$_{31}$ClF$_2$N$_2$O$_4$S: C, 58.64; H, 5.65; N, 5.06. Found: C, 58.43; H, 5.68; N, 5.06.

EXAMPLE 97

N-[4-[3-[4-[Bis(4-fluorophenyl)hydroxymethyl]-1-piperidinyl]propoxy]phenyl]methanesulfonamide Following the procedure of Example 1, ]α,α-bis(p-fluorophenyl)]-4-piperidinemethanol and N-[4-(3-bromopropoxy)phenyl]methanesulfonamide are reacted to give the title compound.

EXAMPLE 98

N-[4-[3-[4-[Bis(4-fluorophenyl)hydroxymethyl]-1-piperidinyl]propoxy]phenyl]-N'-methylurea Following the procedure of Example 1, [α,α-bis(p-fluorophenyl) ]-4-piperidinemethanol and N-[4-(3-bromopropoxy)phenyl]-N'-methylurea are reacted to give the title compound.

EXAMPLE 99

[4-[3-[4-[Bis(4-fluorophenyl)hydroxymethyl]-1-piperidinyl]propoxy]phenyl]carbamic acid ethyl ester Following the procedure of Example 1, ]α,α-bis)p-fluorophenyl)]-4-piperidinemethanol and [4-(3-bromopropoxy)phenyl]carbamic acid ethyl ester are reacted to give the title compound.

EXAMPLE 100

N-[3-[3-[4-[Bis(4-fluorophenyl)hydroxymethyl]-1-piperidinyl]propoxy]phenyl]urea

Following the procedure of Example 1, [α,α-bis(-fluorophenyl)]-4-piperidinemetnanol and N-[3-(3-bromopropoxy)phenyl]urea are reacted to give the title compound.

EXAMPLE 101

4-[3-[4-[Bis(4-fluorophenyl)hydroxymethyl]-1-piperidinyl]propoxy]-3-methoxybenzoic acid sodium salt Following the procedures of Examples 1 and 85 but substituting 4-(3-chloropropoxy)-2-methoxybenzoic acid for the corresponding 3-methoxy compound, the title compound is prepared.

EXAMPLE 102

1-[4-[3-[4-[Bis(4-fluorophenyl)hydroxymethyl]-piperidinyl]propoxy]-2-hydroxyphenyl]ethanone Following the procedure of Example 1, ]α,α-bis(p-fluorophenyl)-4-piperidinemethanol and 1-[4-(3-bromopropoxy)-2-hydroxyphenyl]ethanone are reacted to give the title compound.

EXAMPLE 103

7-[3-[4-[Bis(4-fluorophenyl)hydroxymethyl]-1-piperidinyl]propoxy]-4-oxo-4H-1-benzopyran-2-carboxylic acid ethyl ester hydrochloride A mixture of 3.0 g (0.01 mole) of [α,α-bis(p-fluorophenyl)]-4-piperidinemethanol, 3.1 g (0.01 mol) of 7-(3-chloropropoxy)-4-oxo-4H-1-benzopyran-2-carboxylic acid ethyl ester, 5.3 g (0.05 mole) of anhydrous sodium carbonate and 0.3 g of potassium iodide in 150 ml of acetonitrile heated at reflux for 48 hr gave a gum as residue. The gum was purified by column chromatography on 120 g of Florisil ®. The desired fractions eluted with 10% acetone in benzene were combined and concentrated under reduced pressure to give a glass as residue. The glass was dissolved in etherisopropanol and treated with ethereal hydrogen chloride. The solid which precipitated was collected by filtration and recrystallized from absolute ethanol to give 1.9 g (31%) of white solid, m.p. 191° C. with decomposition.

Analysis: Calculated for $C_{33}H_{34}ClF_2NO_6$: C, 64.55; H, 5.58; N, 2.28. Found: C, 64.41; H, 5.51; N, 2.26.

EXAMPLE 104

7-[3-[4-[Bis(4-fluorophenyl)hydroxymethyl]-1-piperidinyl]propoxy]-2,3-dihydro-4H-1-benzopyran-4-one hydrochloride Following the procedure of Example 103, [α,α-bis(p-fluorophenyl)]-4-piperidinemethanol and 7-(3-bromopropoxy)-2,3-dihydro-4H-1-benzopyran-4-one are reacted to give the title compound.

EXAMPLE 105

1-[4-[3-[4-(Diphenylmethylene)-1-piperidinyl]propoxy]-3-methoxyphenyl]ethanone oxalate hydrate ]1:1:05]

A mixture of 7.5 g (0.03 mole) of 4-diphenylmethylenepiperidine, 6.3 g (0.032 mole) of 3-(p-acetyl-o-methoxyphenoxy)propyl bromide, 25 g of potassium carbonate and 150 ml of toluene was heated at reflux for 16 hrs, cooled, filtered and the solvent evaporated at reduced pressure. The residual oil was taken up in benzene, washed with water, dried over magnesium sulfate and then the solvent was evaporated. The free base was dissolved in isopropanol and treated with 3.8 g (0.03 mole) of oxalic acid dihydrate in dry ether. The white salt which separated was recrystallized from an isopropanol-methanol mixture. The product weighed 8.5 g(54%). m.p. 186°–188° C.

Analysis: Calculated for $C_{32}H_{36}NO_{7.5}$: C, 69.29; H, 6.54; N, 2.53. Found: C, 69.20; H, 6.49; N, 2.71.

EXAMPLE 106

1-[4-[3-[4-(Cyclohexylphenylmethyl)-1,2,3,6-tetrahydropyridin-1-yl]propoxy]3-methoxyphenyl]ethanone oxalate hydrate ]1:1:0.5]

The free base of the title compound was obtained by reacting 4-(α-cyclohexylphenylmethyl)-1,2,3,6-tetrahydropyridine with 3-(p-acetyl-o-methoxyphenoxy)propyl chloride in a mixture with sodium bicarbonate in dimethylformamide and isolated on a Florisil ® column eluting with benzene. The title salt was prepared, m.p. 110° C.

Analysis: Calculated for $C_{64}H_{84}N_2O_{15}$: C, 68.55; H, 7.55; N, 2.50. Found: C, 68.79; H, 7.64; M, 2.47.

EXAMPLE 107

1-[4-[3-[4-[Bis(4-fluorophenyl)hydroxymethyl]-1-piperidinyl]propoxy]-2-methoxyphenyl]ethanone hydrochloride [1:1]

This compound was prepared according to the procedure used to synthesize the compound of Example 1. A mixture of 3.0 g (0.01 mole) of [α,α-bis(p-fluorophenyl)]-4-piperidinemethanol. 2.4 g (0.01 mole) of 1-[4-(3-chloropropoxy)-2-methoxyphenyl]ethanone, 5.3 g (0.05 mole) of anhydrous sodium carbonate and 0.3 g of potassium iodide in 100 ml of 1-butanol gave a gum as residue. The gun was purified by column chromatography on 80 g of Florisil ® and the fractions eluted with 20% acetone in benzene were combined and concentrated under reduced pressure to give a solid as residue. The solid was converted to the hydrochloride and this solid was recrystallized from 2-propanol-isopropyl ether to yield 2.2 g (40%) of white powder, m.p. 196°–197° C.

Analysis: Calculated for $C_{30}H_{34}ClF_2NO_4$: C, 65.99; H, 6.28; N, 2.57. Found: C, 65.87; H, 6.31; N, 2.54.

EXAMPLE 108

4-[Bis(4-fluorophenyl)methyl]-1-[3-(2,6-dichlorophenoxy)propyl]piperidine

A mixture of 4-[bis(4-fluorophenyl)methyl]piperidine (free base 6.90 g, 0.024 mole), 1,3-dichloro-1,2-dichloro-2-(3-chloropropoxy)benzene (5.72 g, 0.024 mole), and potassium carbonate (5.54 g, 0.04 mole) was heated overnight at gentle reflux in 350 ml of 1-butanol containing potassium iodide (0.2 g). The reaction was stripped to dryness. The residue was partitioned several times between chloroform and water. The chloroform layer was dried, filtered, and solvent removed to give an oil. The oil was placed in the refrigerator overnight in 50 ml of methanol. A white solid was obtained and dried in vacuo overnight at 80° C. A yield of 3.26 g (27.7%) of white crystalline solid, m.p. 101.5°–103° C. was obtained.

Analysis: Calculated for $C_{27}H_{27}NOCl_2F_2$: C, 66013; H, 5.55; N, 2.85. Found: C, 66.12; H, 5.56; N, 2.88.

EXAMPLE 109

4-[Bis(4-fluorophenyl)methyl]-1-[3-(2,6-dichlorophenoxy)propyl]piperidine oxalate [1:1]

Free base of the compound of Example 108 was converted to the oxalate salt and recrystallized from methanol-diethyl ether and dried in vacuo at 80° C. overnight, m.p. 158°–161° C.

Analysis: Calculated for $C_{29}H_{29}NO_5Cl_2F_2$: C, 60.01; H, 5.04; N, 2.44. Found: C, 60.02; H, 5.07; N, 2.46.

EXAMPLE 110

2-[3-[4-[Bis(4-fluorophenyl)methyl]-1-piperidinyl]propoxy]benzonitrile

A mixture of 7.41 g (0.025 mole) of 4-]bis(4-fluorophenyl)methyl]piperidine, 4.90 g (0.025 mole) of 2-(3-chloropropoxy)benzonitrile, and potassium carbonate, 5.54 g (0.04 mole) was heated overnight at reflux in 350 ml of 1-butanol containing potassium iodide (0.2 g). The mixture was stripped to dryness and the resulting residue was partitioned several times between water and chloroform. The chloroform layer was dried (anhydrous sodium sulfate), filtered, and solvent removed to give a brown oil. The oil was triturated with diethyl ether and placed in a freezer overnight. White crystals were obtained and dried in vacuo overnight at room temperature. A yield of 5.15 g (46.1%) of analytically pure material, m.p. 88.5°–90° C. was obtained.

Analysis: Calculated for $C_{28}H_{28}N_2OF_2$: C, 75.31; H, 6.36; N, 6.27. Found: C, 75.16; H, 6.34; N, 6.26.

EXAMPLE 111

α-[1-[3-(4-Acetyl-2-methoxyphenoxy)propyl]-4-piperidinyl]-α-(4-fluorophenyl)-2-pyridineacetonitrile fumarate [1:1]

A mixture of α-(4-fluorophenyl)-α-(4-piperidinyl)-2-pyridineacetonitrile (7.18 g, 0.024339 mole), 1-[4-(3-chloropropoxy)-3-methoxyphenyl]ethanone (5.89 g, 0.024339 mole), and potassium carbonate (5.54 g, 0.04 mole) was heated overnight in 530 ml of 1-butanol containing potassium iodide (0.15 g). The reaction mixture was stripped to dryness and the residue obtained was partitioned between chloroform and water. The chloroform layer was extracted with 1N sulfuric acid, 5% sodium hydroxide and water. The chloroform layer was dried over sodium sulfate, filtered, and the solvent removed to give an oil. The oil was converted to the fumarate salt and recrystallized from methanol-diethyl ether. A white solid was obtained and dried in vacuo overnight at 80° C. to give 9.43 g (62.7%) of white crystals, m.p. 166°–167° C.

Analysis: Calculated for $C_{34}H_{36}N_3O_7F$: C, 66.11; H, 5.87; N, 6.80. Found: C, 65.57; H, 5.89; N, 6.70. (¼ $H_2O$ found by NMR).

EXAMPLE 112

α-[1-[3-(4-Acetyl-2-methoxyphenoxy)propyl]-4-piperidinyl]-α-(4-fluorophenyl)-2-pyridineacetonitrile fumarate monohydrate

A portion of the compound prepared in Example 111 was exposed to the air for 3 days, m.p. 166°–167° C.

Analysis: Calculated for $C_{34}H_{38}N_3O_8F$: C, 64.24; H, 6.02; N, 6.61. Found: C, 64.27; H, 5.82; N, 6.58.

EXAMPLE 113

α,α-Diphenyl-1-[3-(8-quinolinyloxy)propyl]-3-piperidinepropanenitrile hemihydrate

A mixture of α,α-diphenyl-3-piperidinepropanenitrile (8.12 g, 0.028 mole), 8-(3-chloropropoxy)quinoline (6.18 g, 0.028 mole), and potassium carbonate (5.53 g, 0.04 mole) was heated at reflux overnight in 350 ml of 1-butanol containing potassium iodide (0.3 g). The reaction was filtered and stripped to dryness on a rotary evaporator. The residue obtained was dissolved in chloroform and extracted with 5% sodium hydroxide and water. The chloroform layer was dried over anhydrous sodium sulfate, filtered, and solvent removed to give a dark red mass. This material was subjected to flash chromatography on a silica gel column using 10% methanol-ethyl acetate, 20% methanol-ethyl acetate, and 50% methanol-ethyl acetate for elution. Fractions of similar purity were combined and solvent was removed by rotary evaporator. The red black residue obtained was dried in vacuo at 80° C. overnight. This furnished 5.29 g (39%) of a dark black residue. $^1H$ NMR ($CDCl_3$): σ 8.9 (m, 1, proton ortho to N in ring), 7.9–8.1 (m, 1, proton para to N in ring), 6.9–7.6 (m, 14, aromatics), 4.2 (t, 2, methylenes adjacent to oxygen atom), 1.1–2.7 (m, 16, aliphatic portons and 1H from 0.5 $H_2O$).

Analysis: Calculated for $C_{32}H_{33}N_3O_{1.5}$: C, 79.31; H, 7.07; N, 8.67. Found: C, 79.47; H, 7.19; N, 8.69.

EXAMPLE 114

8-[3-[4-[Bis(4-fluorophenyl)methyl]-1-piperidinyl]propoxy]quinoline hemihydrate

A mixture of 4-(α-p-fluorophenyl)-p-fluorobenzyl-piperidine (8.03 g, 0.28 mole), 8-(3-chloropropoxy)quinoline (6.18 g, 0.28 mole), and potassium carbonate (5.53 g, 0.04 mole) was heated overnight at gentle reflux in 350 ml of 1-butanol containing potassium iodide (0.3 g). The reaction mixture was filtered through activated charcoal and solvent was removed by rotary evaporator. The dark red residue was dissolved in chloroform and then extracted with 5% sodium hydroxide and water. The chloroform layer was dried over anhydrous sodium, filtered, and solvent removed to provide a dark red mass. This material was subjected to flash chromatography on silica gel using 10, 20 and 50% methanol in ethyl acetate for elution. Fractions with similar purity were combined and solvent removed to give a dark black mass which was dried at 80° C. in vacuo overnight. This furnished 3.74 g (28%) of a dark red mass.

$^1H$ NMR ($CDCl_3$): σ 8.9 (M, 1, proton ortho to N in ring), 7.9–8.1 (m, 1, proton para to N in ring), 6.8–7.4 (m, 12, aromatic), 4.2 (t, 2, $CH_2$ attached to 0), 3.5 )d, 1, methine attached to two aromatic rings), 1.0–3.2 (m, 14, aliphatic protoms and 1H for 0.5 $H_2O$).

Analysis: Calculated for $C_{30}H_{30.5}N_2O_{1.5}F_2$: C, 75.53; H, 6.44; N, 5.87. Found: C, 75.66; H, 6.56; N, 5.86.

EXAMPLE 115

2-[3-[4-[Bis(4-fluorophenyl)methyl]-1-piperidinyl]propoxy]quinoline hydrate [1:0.5]

The sodium salt of 4-[bis(4-fluorophenyl)methyl]-1-piperidinepropanol was formed in 300 ml of dimethyl sulfoxide from its free base (6.90 g, 0.02 mole) and sodium hydride (60%, 0.8 g, 0.02 mole). 2-Chloroquinoline (3.26 g, 0.02 mole) was added and the reaction mixture was heated at 60° C. over the week-end. The reaction mixture was stripped to dryness and the residue obtained was dissolved in chloroform. The chloroform layer was extracted with water and 5% sodium hydroxide. The chloroform layer was dried over sodium sulfate, filtered, and solvent removed to give an oil. The oil was subjected to flash chromatography on silica gel using ethyl acetate for elution. Fractions of similar purity were combined and solvent removed. The residue was dried in vacuo overnight at 80° C. to give 5.16 g (53.6%) of clear brown oil.

$^1$H NMR (CDCl$_3$): δ6.8–7.9 (m, 14, aromatics), 4.5 (t, 2, —OCH$_2$), 3.4 and 3.6 (d, 1, methine attached to two aromatic rings), 1.2–3.1 (m, 13, aliphatics remaining).

Analysis: Calculated for C$_{30}$H$_{31}$N$_2$O$_{7.5}$F$_2$: C, 74.82; H, 6.49; N, 5.82. Found: C, 74.56; H, 6.36; N, 5.69.

TABLE 1

$$\text{Ar} \diagdown \underset{R}{\overset{(A)_d}{C}} = (Q)_n \diagdown \underset{p}{\bigcirc} N-(CH_2)_m-O-D$$

| Ex. No. | p | Ar | R | (A)$_d$ | (Q)$_n$ | Ring Position | m | D | Salt |
|---|---|---|---|---|---|---|---|---|---|
| 1 | 1 | C$_6$H$_5$— | C$_6$H$_5$— | — | — | 4 | 3 | C$_6$H$_5$— | oxalate |
| 2 | 1 | 4-F—C$_6$H$_4$— | 4-F—C$_6$H$_4$— | OH | — | 4 | 3 | C$_6$H$_5$— | oxalate 0.5 H$_2$O |
| 3 | 1 | 4-F—C$_6$H$_4$— | 4-F—C$_6$H$_4$— | — | — | 4 | 3 | C$_6$H$_5$— | oxalate |
| 4 | 1 | 4-F—C$_6$H$_4$— | 4-F—C$_6$H$_4$— | OH | — | 4 | 3 | C$_6$H$_5$— | oxalate |
| 5 | 1 | C$_6$H$_5$— | C$_6$H$_5$— | H | — | 4 | 4 | C$_6$H$_5$— | fumarate |
| 6 | 1 | C$_6$H$_5$— | C$_6$H$_5$— | H | — | 4 | 3 | C$_6$H$_5$— | fumarate |
| 7 | 1 | 4-F—C$_6$H$_4$— | 4-F—C$_6$H$_4$— | H | — | 4 | 4 | C$_6$H$_5$— | oxalate |
| 8 | 1 | 4-F—C$_6$H$_4$— | C$_6$H$_5$— | H | — | 4 | 2 | C$_6$H$_5$— | fumarate |
| 9 | 1 | 4-F—C$_6$H$_4$— | 4-F—C$_6$H$_4$— | H | — | 4 | 4 | C$_6$H$_5$— | oxalate |
| 10 | 1 | 4-F—C$_6$H$_4$— | 4-F—C$_6$H$_4$— | H | — | 4 | 3 | C$_6$H$_5$— | oxalate |
| 11 | 1 | 4-F—C$_6$H$_4$— | C$_6$H$_5$— | H | — | 4 | 3 | C$_6$H$_5$— | fumarate |
| 12 | 1 | 4-F—C$_6$H$_4$— | 4-F—C$_6$H$_4$— | OH | — | 4 | 2 | 2,6-Cl$_2$—C$_6$H$_3$— | — |
| 13 | 1 | 4-F—C$_6$H$_4$— | 4-F—C$_6$H$_4$— | OH | — | 4 | 3 | 4-Cl—C$_6$H$_4$— | oxalate |
| 14 | 1 | 4-F—C$_6$H$_4$— | 4-F—C$_6$H$_4$— | H | — | 4 | 3 | 2-F—C$_6$H$_4$— | mandelate |
| 15 | 1 | 4-F—C$_6$H$_4$— | 4-F—C$_6$H$_4$— | H | — | 4 | 3 | 3-F—C$_6$H$_4$— | fumarate |
| 16 | 1 | 4-F—C$_6$H$_4$— | 4-F—C$_6$H$_4$— | H | — | 4 | 3 | 4-Cl—C$_6$H$_4$— | — |
| 17 | 1 | 4-F—C$_6$H$_4$— | 4-F—C$_6$H$_4$— | H | — | 4 | 3 | 4-F—C$_6$H$_4$— | fumarate |
| 18 | 1 | 4-F—C$_6$H$_4$— | 4-F—C$_6$H$_4$— | H | — | 4 | 3 | 4-OCH$_3$—C$_6$H$_4$— | fumarate |
| 19 | 1 | 4-F—C$_6$H$_4$— | 4-F—C$_6$H$_4$— | H | — | 4 | 3 | 2-OCH$_3$—C$_6$H$_4$— | — |
| 20 | 1 | 4-F—C$_6$H$_4$— | 4-F—C$_6$H$_4$— | OH | — | 4 | 3 | 2-OCH$_3$—C$_6$H$_4$— | — |
| 21 | 1 | 4-F—C$_6$H$_4$— | 4-F—C$_6$H$_4$— | H | — | 4 | 3 | 2-OCH$_3$—C$_6$H$_4$— | oxalate |
| 22 | 1 | 4-F—C$_6$H$_4$— | 4-F—C$_6$H$_4$— | H | — | 4 | 3 | 3,4-(OCH$_3$)$_2$—C$_6$H$_3$— | oxalate |
| 23 | 1 | 4-CH$_3$—C$_6$H$_4$— | 4-CH$_3$—C$_6$H$_4$— | H | — | 4 | 3 | 2,6-(OCH$_3$)$_2$—C$_6$H$_3$— | fumarate |
| 24 | 1 | 4-F—C$_6$H$_4$— | 4-F—C$_6$H$_4$— | H | — | 4 | 3 | 3,4-(OCH$_3$)$_2$—C$_6$H$_3$— | oxalate |
| 25 | 1 | 4-F—C$_6$H$_4$— | 4-F—C$_6$H$_4$— | H | — | 4 | 3 | 2,6-(OCH$_3$)$_2$—C$_6$H$_3$— | oxalate, H$_2$O |
| 26 | 1 | 4-F—C$_6$H$_4$— | 4-F—C$_6$H$_4$— | H | — | 4 | 3 | 3,5-(OCH$_3$)$_2$—C$_6$H$_3$— | — |
| 27 | 1 | 4-OCH$_3$—C$_6$H$_4$— | 4-OCH$_3$—C$_6$H$_4$— | H | — | 4 | 3 | 3,4-(OCH$_3$)$_2$—C$_6$H$_3$— | fumarate, 0.5 H$_2$O |
| 28 | 1 | 4-OCH$_3$—C$_6$H$_4$— | 4-OCH$_3$—C$_6$H$_4$— | H | — | 4 | 3 | 4-OCH$_3$—C$_6$H$_4$— | oxalate |
| 29 | 1 | 4-F—C$_6$H$_4$— | 4-F—C$_6$H$_4$— | — | — | 4 | 3 | 4-C(O)CH$_3$—C$_6$H$_4$— | oxalate |
| 30 | 1 | 4-F—C$_6$H$_4$— | 4-F—C$_6$H$_4$— | H | — | 4 | 3 | 4-C(O)CH$_3$—C$_6$H$_4$— | 2-propanolate |
| 31 | 1 | 4-F—C$_6$H$_4$— | 4-F—C$_6$H$_4$— | OH | — | 4 | 3 | 4-C(O)CH$_3$—C$_6$H$_4$— | — |
| 32 | 1 | 4-F—C$_6$H$_4$— | 4-F—C$_6$H$_4$— | OH | — | 4 | 3 | 2-CH$_3$—4-C(O)CH$_3$—C$_6$H$_3$ | fumarate |
| 33 | 1 | 4-F—C$_6$H$_4$— | 4-F—C$_6$H$_4$— | OH | — | 4 | 3 | 4-CN—C$_6$H$_4$— | — |
| 34 | 1 | 4-F—C$_6$H$_4$— | 4-F—C$_6$H$_4$— | H | — | 4 | 3 | 4-CN—C$_6$H$_4$— | fumarate |
| 35 | 1 | 4-F—C$_6$H$_4$— | 4-F—C$_6$H$_4$— | OH | — | 4 | 3 | 4-C(O)OC$_2$H$_5$—C$_6$H$_4$— | HCl |
| 36 | 1 | 4-F—C$_6$H$_4$— | 4-F—C$_6$H$_4$— | OH | — | 4 | 3 | 4-C(O)OH—C$_6$H$_4$— | HCl, 0.5 H$_2$O |

| No. | | | | | | | |
|---|---|---|---|---|---|---|---|
| 37 | 1 | 4-F—C₆H₄— | 4-F—C₆H₄— | — | — | 3 | 4-C(O)OC₂H₅—C₆H₄— | HBr |
| 38 | 1 | 4-F—C₆H₄— | 4-F—C₆H₄— | H | — | 3 | 4-C(O)OC₂H₅—C₆H₄— | HBr |
| 39 | 1 | 4-OCH₃—C₆H₄— | 4-OCH₃—C₆H₄— | H | — | 3 | 4-C(O)OC₄H₉—C₆H₄— | — |
| 40 | 1 | 4-OCH₃—C₆H₄— | 4-OCH₃—C₆H₄— | H | — | 3 | 4-C(O)OC₂H₅—C₆H₄— | fumarate, 0.5 H₂O |
| 41 | 1 | 4-F—C₆H₄— | 4-F—C₆H₄— | OH | — | 2 | 4-C(O)OC₂H₅—C₆H₄— | HCl |
| 42 | 1 | 4-F—C₆H₄— | 4-F—C₆H₄— | OH | — | 3 | 2-OCH₃—4-CH₂—C(O)OC₂H₅—C₆H₄ | HCl |
| 43 | 1 | 4-F—C₆H₄— | 4-F—C₆H₄— | — | — | 3 | 4-t-butyl-C₆H₄— | fumarate |
| 44 | 1 | 4-OCH₃—C₆H₄— | 4-OCH₃—C₆H₄— | H | — | 3 | 4-t-butyl-C₆H₄— | fumarate, 0.5 H₂O |
| 45 | 1 | 4-OCH₃—C₆H₄— | 4-OCH₃—C₆H₄— | H | — | 3 | 4-t-butyl-C₆H₄— | oxalate |
| 46 | 1 | 4-F—C₆H₄— | 4-F—C₆H₄— | OH | — | 3 | 3-CF₃—C₆H₄— | — |
| 47 | 1 | 4-F—C₆H₄— | 4-F—C₆H₄— | H | — | 3 | 4-NHC(O)CH₃—C₆H₄— | oxalate |
| 48 | 1 | 4-CH₃—C₆H₄— | 4-CH₃—C₆H₄— | H | — | 3 | 4-NHC(O)CH₃—C₆H₄ | fumarate, 0.5 H₂O |
| 49 | 1 | 4-F—C₆H₄— | 4-F—C₆H₄— | H | — | 3 | 4-NH₂—C₆H₄— | HBr |
| 50 | 1 | 4-F—C₆H₄— | 4-F—C₆H₄— | OH | — | 3 | 4-NHC(O)CH₃—C₆H₄— | fumarate, 0.5 H₂O |
| 51 | 1 | 4-F—C₆H₄— | 4-F—C₆H₄— | OH | — | 3 | 4-NO₂—C₆H₄— | HCl, H₂O |
| 52 | 1 | 4-F—C₆H₄— | 4-F—C₆H₄— | H | — | 3 | 4-C(O)NH₂—C₆H₄— | — |
| 53 | 1 | 4-F—C₆H₄— | 4-F—C₆H₄— | H | — | 2 | 1-C₁₀H₇— | — |
| 54 | 1 | 4-F—C₆H₄— | 4-F—C₆H₄— | — | — | 2 | 2-C₁₀H₇— | — |
| 55 | 1 | 4-F—C₆H₄— | 4-F—C₆H₄— | — | — | 3 | 2-OCH₃—4-C(O)CH₃C₆H₃— | HCl |
| 56 | 1 | 4-F—C₆H₄— | 4-F—C₆H₄— | H | — | 3 | 2-OCH₃—4-C(O)CH₃—C₆H₃ | oxalate |
| 57 | 1 | 4-F—C₆H₄— | 4-F—C₆H₄— | H | — | 3 | 2-OCH₃—4-C(O)CH₃—C₆H₃ | oxalate |
| 58 | 1 | 4-F—C₆H₄— | 4-F—C₆H₄— | H | — | 3 | 2-OCH₃—4-C(O)CH₃—C₆H₃ | 1.2 fumarate |
| 59 | 1 | 3-CF₃—C₆H₄— | C₆H₅— | — | — | 3 | 2-OCH₃—4-C(O)CH₃—C₆H₃ | oxalate |
| 60 | 1 | C₆H₅— | C₆H₅— | — | — | 3 | 2-OCH₃—4-C(O)CH₃—C₆H₃ | Oxalate |
| 61 | 1 | C₆H₅— | C₆H₁₁— | H | — | 3 | 2-OCH₃—4-C(O)CH₃—C₆H₃ | oxalate |
| 62 | 1 | C₆H₁₁— | C₆H₁₁— | — | — | 3 | 2-OCH₃—4-C(O)CH₃—C₆H₃ | oxalate |
| 63 | 1 | 4-F—C₆H₄— | 4-F—C₆H₄— | H | — | 3 | 2-OCH₃—4-C(O)CH₃—C₆H₃ | oxalate, 0.5 H₂O |
| 64 | 1 | 4-F—C₆H₄— | 4-F—C₆H₄— | H | — | 3 | 4-COHCH₃—C₆H₄— | oxalate |
| 65 | 1 | C₆H₅— | C₆H₅— | OH | — | 3 | 2-OCH₃—4-COHCH₃—C₆H₃ | oxalate |
| 66 | 1 | 4-F—C₆H₄— | 4-F—C₆H₄— | OH | — | 3 | 2-OCH₃—4-C(O)CH₃—C₆H₃ | — |
| 67 | 1 | 4-F—C₆H₄— | C₆H₅— | OH | — | 3 | 2-OCH₃—4-C(O)CH₃—C₆H₃ | — |
| 68 | 1 | C₆H₅— | C₆H₅— | OH | — | 3 | 2-OCH₃—4-C(O)CH₃—C₆H₃ | — |
| 69 | 1 | 3-CF₃—C₆H₄— | C₆H₅— | OH | — | 3 | 2-OCH₃—4-C(O)CH₃—C₆H₃ | oxalate |
| 70 | 1 | C₆H₅— | C₆H₁₁— | OH | — | 3 | 2-OCH₃—4-C(O)CH₃—C₆H₃ | HCl, 0.5 H₂O |
| 71 | 1 | 4-F—C₆H₄— | 4-F—C₆H₄— | OH | — | 2 | 2-OCH₃—4-C(O)CH₃—C₆H₃ | HCl |
| 72 | 1 | 4-F—C₆H₄— | 4-F—C₆H₄— | OH | — | 4 | 2-OCH₃—4-C(O)CH₃—C₆H₃ | — |
| 73 | 1 | 4-F—C₆H₄— | 4-F—C₆H₄— | OH | — | 5 | 2-OCH₃—4-C(O)CH₃—C₆H₃ | — |
| 74 | 1 | 4-F—C₆H₄— | 4-F—C₆H₄— | H | — | 2 | 2-OCH₃—4-C(O)CH₃—C₆H₃ | — |

| # | | | | | | | |
|---|---|---|---|---|---|---|---|
| 75 | 4-Cl—C₆H₄— | 4-Cl—C₆H₄— | 1 | — | — | 4 | 2-OCH₃—4-C(O)CH₃—C₆H₃— | — |
| 76 | 4-F—C₆H₄— | C₆H₅— | 1 | H | — | 4 | 2-OCH₃—4-C(O)CH₃—C₆H₃— | oxalate |
| 77 | 4-OCH₃—C₆H₄— | 4-OCH₃—C₆H₄— | 1 | H | — | 4 | 2-OCH₃—4-C(O)CH₃—C₆H₃— | oxalate |
| 78 | 4-CH₃—C₆H₄— | 4-CH₃—C₆H₄— | 1 | H | — | 4 | 2-OCH₃—4-C(O)CH₃—C₆H₃— | — |
| 79 | 4-F—C₆H₄— | 4-F—C₆H₄— | 1 | H | — | 4 | 2-OCH₃—4-C(O)CH₃—C₆H₃— | — |
| 80 | 4-F—C₆H₄— | 4-F—C₆H₄— | 1 | OH | — | 4 | 2-OCH₃—4-C(O)CH₃—C₆H₃— | — |
| 81 | 4-F—C₆H₄— | 4-F—C₆H₄— | 1 | OH | — | 4 | 2-OCH₃—4-C(O)OCH₃—C₆H₃— | fumarate |
| 82 | 4-F—C₆H₄— | 4-F—C₆H₄— | 1 | OH | — | 4 | 4-SCH₃—C₆H₄— | HCl |
| 83 | 4-F—C₆H₄— | 4-F—C₆H₄— | 1 | OH | — | 4 | 4-S(O)₂CH₃—C₆H₄— | HCl |
| 84 | 4-F—C₆H₄— | 4-F—C₆H₄— | 1 | OH | — | 2 | 2-OCH₃—4-CH₂—C(O)OC₂H₅—C₆H₃— | — |
| 85 | 4-F—C₆H₄— | 4-F—C₆H₄— | 1 | OH | — | 3 | 4-C(O)OC₂H₅—C₆H₄— | 0.5 H₂O |
| 86 | 4-F—C₆H₄— | 4-F—C₆H₄— | 1 | OH | — | 4 | 2-OCH₃—4-CH₂C(O)—ON_a—C₆H₃ | — |
| 87 | 4-F—C₆H₄— | 4-F—C₆H₄— | 1 | OH | — | 4 | 2-C(O)OC₂H₅—C₆H₄— | 0.75 fumarate |
| 88 | 4-F—C₆H₄— | 4-F—C₆H₄— | 1 | H | — | 4 | 2-C(O)OC₂H₅—C₆H₄— | — |
| 89 | 4-F—C₆H₄— | 4-F—C₆H₄— | 1 | H | — | 5 | 2-OCH₃—4-C(O)CH₃—C₆H₃— | — |
| 90 | 4-F—C₆H₄— | 4-F—C₆H₄— | 1 | H | — | 3 | 4-C(O)NH₂—C₆H₄— | 0.5 H₂O |
| 91 | 4-F—C₆H₄— | 4-F—C₆H₄— | 1 | OH | — | 6 | 4-SO₂CH₃—C₆H₄— | 1.5 fumarate |
| 92 | 4-F—C₆H₄— | 4-F—C₆H₄— | 1 | OH | — | 3 | 2-OCH₃—4-C(O)CH₃—C₆H₃— | oxalate |
| 93 | 4-F—C₆H₄— | 4-F—C₆H₄— | 1 | OH | — | 3 | 3-OCH₃—4-C(O)CH₃—C₆H₃— | — |
| 94 | 4-F—C₆H₄— | 4-F—C₆H₄— | 1 | OH | — | 3 | 2-OH—C₆H₄— | — |
| 95 | 4-F—C₆H₄— | 4-F—C₆H₄— | 1 | OH | — | 4 | 4-S(O)CH₃—C₆H₄— | fumarate |
| 96 | 4-F—C₆H₄— | 4-F—C₆H₄— | 1 | OH | — | 4 | 4-S(O)₂NH₂—C₆H₄— | HCl |
| 97 | 4-F—C₆H₄— | 4-F—C₆H₄— | 1 | OH | — | 3 | 4-NHS(O)₂CH₃—C₆H₄— | — |
| 98 | 4-F—C₆H₄— | 4-F—C₆H₄— | 1 | OH | — | 3 | 4-NHC(O)NHCH₃—C₆H₄— | — |
| 99 | 4-F—C₆H₄— | 4-F—C₆H₄— | 1 | OH | — | 3 | 4-NHC(O)NHC₂H₅—C₆H₄— | — |
| 100 | 4-F—C₆H₄— | 4-F—C₆H₄— | 1 | OH | — | 3 | 3-NHC(O)NH₂—C₆H₄— | — |
| 101 | 4-F—C₆H₄— | 4-F—C₆H₄— | 1 | OH | — | 3 | 2-OCH₃—4-COOH—C₆H₃— | sodium |
| 102 | 4-F—C₆H₄— | 4-F—C₆H₄— | 1 | OH | — | 3 | 3-OH—4-C(O)CH₃—C₆H₃— | — |
| 103 | 4-F—C₆H₄— | 4-F—C₆H₄— | 1 | OH | — | 3 | [4-methyl-2-C(O)OC₂H₅-chromen-4-one structure] | HCl |
| 104 | 4-F—C₆H₄— | 4-F—C₆H₄— | 1 | OH | — | 3 | [7-methyl-chroman-4-one structure] | HCl |
| 105 | C₆H₅— | C₆H₅— | 1 | — | — | 4 | 2-OCH₃—4-C(O)CH₃—C₆H₃— | oxalate, 0.5 H₂O |
| 106 | C₆H₅— | C₆H₁₁— | 1 | H | — | 4* | 2-OCH₃—4-C(O)CH₃—C₆H₃— | oxalate, 0.5 H₂O |
| 107 | 4-F—C₆H₄— | 4-F—C₆H₄— | 1 | OH | — | 4 | 3-OCH₃—4-C(O)CH₃—C₆H₃— | HCl |
| 108 | 4-F—C₆H₄— | 4-F—C₆H₄— | 1 | H | — | 4 | 2,6-Cl₂—C₆H₃— | — |

-continued

| # | | | | | | | |
|---|---|---|---|---|---|---|---|
| 109 | 1 | 4-F—C$_6$H$_4$— | 4-F—C$_6$H$_4$— | H | — | 4 | 3 | 2,6-Cl$_2$—C$_6$H$_3$— | oxalate |
| 110 | 1 | 4-F—C$_6$H$_4$— | 4-F—C$_6$H$_4$— | H | — | 4 | 3 | 2-CN—C$_6$H$_4$— | — |
| 111 | 1 | 4-F—C$_6$H$_4$— | 2-pyrido | —CN | — | 4 | 3 | 2-OCH$_2$—4-C(O)CH$_2$—C$_6$H$_3$— | fumarate |
| 112 | 1 | 4-F—C$_6$H$_4$— | 2-pyrido | —CN | — | 4 | 3 | 2-OCH$_3$—4-C(O)CH$_3$—C$_6$H$_3$— | fumarate.H$_2$O |
| 113 | 1 | C$_6$H$_5$— | C$_6$H$_5$— | —CN | —CH$_2$— | 3 | 3 | quinolin-8-yl | 0.5 H$_2$O |
| 114 | 1 | 4-F—C$_6$H$_4$— | 4-F—C$_6$H$_4$— | H | — | 4 | 3 | quinolin-8-yl | 0.5 H$_2$O |
| 115 | 1 | 4-F—C$_6$H$_4$— | 4-F—C$_6$H$_4$— | H | — | 4 | 3 | quinolin-2-yl | 0.5 H$_2$O |

*1,2,3,6-tetrahydropyridine.

PHARMACOLOGY METHODS

Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205–209 (1977) which measures the effect of oral administration of the compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 225). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intraveneous injection of the antigen, 2 mg of egg albumin in 0.2 ml of sterile saline. Thirty minutes later the right foot volume is measured again and edema is determined by difference. Results are expressed as the average foot edema (ml) $\pm$S. S.D. A significant decrease ($p<0.05$) in edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Missouri), at least 20 days prior to aerosol challenge by receiving 0.5 ml of EA-AlOH$_3$ conjugate (33 $\mu$g EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I cpd.) dissolved or suspended in 0.5% Tween 80 distilled water or the control article (0.5% Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspnea, reeling, collapse and death. Upon collapsing, the animals are removed from the chamber. Animals are considered protected if they do not collapse within 5 min of exposure to the aerosolized antigen. The number of animals that collapse in each group is recorded. ED$_{50}$ for collapse is calculated by the method of Litchfield and Wilcoxon (1949), J. PHARMACOL. EXP. THERAP. 95, 99–113 for evaluation of dose-effect experiments. Comparisons of ED$_{50}$x from different experimental trials and determinations of relative potency are determined by the Litchfield and Wilcoxon method, ibid. The following conditions must be met before an experiment is acceptable:

(1) Control group shows collapse in ⅞ or 8/8 animals, and
(2) Theophylline reference group shows protection in ¾ or 4/4 animals treated 1 hr or 5 hr prior to antigen exposure.

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways, for example, orally as in elixirs, capsules, tablets or coated talbets, parenterally in the form of sterile solutions, suspensions, and in some cases intravenously in the form of sterile solutions, intranasally and to the throat or bronchial region in the form of drops, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or archis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the pharmacology tests on guinea pigs in comparison to certain other anti-allergy drugs suggest an effective dose for an adult will be in the range of 0.5 to 10 mg for the move active compounds with a daily dosage amounting to about 2 to 40 mg/day Based on the animal data, unit dosages containing an amount of compound equivalent to about 0.01 to 0.1 mg of active drug per kilogram of body weight are contemplated. Daily dosages to about 0.05 to 0.5 mg/kg of body weight are contemplated for humans and obviously several small dosage forms may be administered at one time. However, the amount of the active compounds administered need not be limited by these contemplations due to uncertainty in transposing animal data to human treatment.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:

1. A method of inhibiting Type I allergic responses in a living animal body which comprises administering an effective amount of a compound selected from the group having the formula:

$$\text{Ar} \underset{R}{\overset{(A)_d}{\underset{|}{C}}}=(Q)_n = \underset{(-)_p}{\overset{}{\bigg\langle} N-(CH_2)_m-O-D}$$

wherein;
p is zero, one or two;
m is one to six inclusive;
A is hydrogen, hydroxy or cyano;
d is zero or one;
Q is —CH—, —CH$_2$— or $$-\underset{H}{\overset{OH}{\underset{|}{C}}}-$$

n is zero or one;
and when Q is —CH— and n is 1, a double bond is formed with one of the adjacent carbons, but not both, and when n and d are zero at the same time, a double bond is formed between the α-carbon and a carbon of the central heterocyclic amine ring;
Ar, D and R are selected from the group consisting of

[chemical structures]

and in addition,
R may have the values:

[chemical structure]

cycloalkyl or loweralkyl; and
D may have additionally the values;

[chemical structures]

or Ar(CH$_2$)$_{1-4}$; X, Y, and Z are selected from the group consisting of hydrogen, loweralkyl, halogen, $$-NO_2, -O-R^1, -\underset{O}{\overset{O}{\underset{\|}{C}}}-R^1, -CF_3, -C\equiv N, -\overset{O}{\underset{\|}{C}}-N(R^1)_2,$$

$$-N(R^1)_2, -C(O)OR^1, -SO_2R^2, -SR^2, -S(O)R^2,$$

$$-\underset{R^1}{\overset{}{\underset{|}{N}}}-\underset{O}{\overset{}{\underset{\|}{C}}}-R^1, -CH_2COOM, -SO_2N\overset{R^1}{\underset{R^1}{\diagdown}}, -\underset{R^1}{\overset{}{\underset{|}{N}}}SO_2CH_3,$$

$$-\underset{R^1}{\overset{}{\underset{|}{N}}}-\underset{O}{\overset{}{\underset{\|}{C}}}-N\overset{R^1}{\underset{R^1}{\diagdown}}, \text{ or } -\underset{R^1}{\overset{}{\underset{|}{N}}}-\underset{O}{\overset{}{\underset{\|}{C}}}-OR^2;$$

$R^1$ is selected from hydrogen, loweralkyl, phenyl and phenylloweralkyl;
$R^2$ is selected from loweralkyl, phenyl and phenylloweralkyl;
M is a pharmaceutically acceptable metal ion;
and the pharmaceutcially acceptable salts thereof, including acid addition salts, quaternary salts and hydrates and alcoholates thereof.

2. The method of claim 1 wherein the compound used is 4-(diphenylmethylene)-1-(3-phenoxypropyl)piperidine or a pharmaceutically acceptable salt thereof.

3. The method of claim 1 wherein the compound used is α,α-bis-(4-fluorophenyl)-1-(3-phenoxypropyl)-4-piperidinemethanol or a pharmaceutically acceptable salt thereof.

4. The method of claim 1 wherein the compound used is 4-[bis(4-fluorophenyl)methylene]-1-(3-phenoxypropyl)-piperidine or a pharmaceutically acceptable salt thereof.

5. The method of claim 1 wherein the compound used is α,α-bis(4-fluorophenyl)-1-(3-phenoxypropyl)-4-piperidinemethanol or a pharmaceutically acceptable salt thereof.

6. The method of claim 1 wherein the compound used is 4-(diphenylmethyl)-1-(4-phenoxybutyl)piperidine or a pharmaceutically acceptable salt thereof.

7. The method of claim 1 wherein the compound used is 4-(diphenylmethyl)-1-(3-phenoxypropyl)piperidine or a pharmaceutically acceptable salt thereof.

8. The method of claim 1 wherein the compound used is 4-[bis(4-fluorophenyl)methyl]-1-(3-phenoxypropyl)-piperidine or a pharmaceutically acceptable salt thereof.

9. The method of claim 1 wherein the compound used is 4-(diphenylmethyl)-1-(2-phenoxyethyl)piperidine or a pharmaceutically acceptable salt thereof.

10. The method of claim 1 wherein the compound used is 4-[bis(4-fluorophenyl)methyl]-1-(2-phenoxyethyl)piperidine or a pharmaceutically acceptable salt thereof.

11. The method of claim 1 wherein the compound used is 4-[bis(4-fluorophenyl)methyl]-1-(4-phenoxybutyl)piperidine or a pharmaceutically acceptable salt thereof.

12. The method of claim 1 wherein the compound used is 4-[(4-fluorophenyl)-phenylmethyl]-1-(3-phenoxypropyl)piperidine or a pharmaceutically acceptable salt thereof.

13. The method of claim 1 wherein the compound used is 4-[bis(4-fluorophenyl)methyl]-1-[2-(2,6-dichlorophenoxy)ethyl]piperidine or a pharmaceutically acceptable salt thereof.

14. The method of claim 1 wherein the compound used is 1-[3-(4-chlorophenoxy)propyl]-α,α-bis(4-fluorophenyl)-4-piperidinemethanol or a pharmaceutically acceptable salt thereof.

15. The method of claim 1 wherein the compound used is 4-[bis(4-fluorophenyl)methyl]-1-[3-(2-fluorophenoxy)propyl]piperidine or a pharmaceutically acceptable salt thereof.

16. The method of claim 1 wherein the compound used is 4-[bis(4-fluorophenyl)methyl]-1-[3-(3-fluorophenoxy)propyl]piperidine or a pharmaceutically acceptable salt thereof.

17. The method of claim 1 wherein the compound used is 4-[bis(4-fluorophenyl)methyl]-1-[3-(4-chlorophenoxy)propyl]piperidine or a pharmaceutically acceptable salt thereof.

18. The method of claim 1 wherein the compound used is 4-[bis(4-fluorophenyl)methyl]-1-[3-(4-fluorophenoxy)propyl]piperidine or a pharmaceutically acceptable salt thereof.

19. The method of claim 1 wherein the compound used is 4-[bis(4-fluorophenyl)methyl]-1-[3-(4-methoxyphenoxy)propyl]piperidine or a pharmaceutically acceptable salt thereof.

20. The method of claim 1 wherein the compound used is 4-[bis(4-fluorophenyl)methyl]-1-[3-(2-methoxyphenoxy)propyl]piperidine or a pharmaceutically acceptable salt thereof.

21. The method of claim 1 wherein the compound used is α,α-bis(4-fluorophenyl)-1-[3-(2-methoxyphenoxy)propyl]-4-piperidinemethanol or a pharmaceutically acceptable salt thereof.

22. The method of claim 1 wherein the compound used is 4-[bis(4-fluorophenyl)methylene]-1-[3-(2-methoxyphenoxy)propyl]piperidine or a pharmaceutically acceptable salt thereof.

23. The method of claim 1 wherein the compound used is 4-[bis(4-fluorophenyl)methyl]-1-[3-(3,4-dimethoxyphenoxy)propyl]piperidine or a pharmaceutically acceptable salt thereof.

24. The method of claim 1 wherein the compound used is 4-[bis(4-methylphenyl)methyl]-1-[3-(2,6-dimethoxyphenoxy)propyl]piperidine or a pharmaceutically acceptable salt thereof.

25. The method of claim 1 wherein the compound used is 4-[bis(4-fluorophenyl)methylene]-1-[3-(3,4-dimethoxyphenoxy)propyl]piperidine or a pharmaceutically acceptable salt thereof.

26. The method of claim 1 wherein the compound used is 4-[bis(4-fluorophenyl)methyl]-1-[3-(2,6-dimethoxyphenoxy)propyl]piperidine or a pharmaceutically acceptable salt thereof.

27. The method of claim 1 wherein the compound used is 4-[bis(4-fluorophenyl)methyl]-1-[3-(3,5-dimethoxyphenoxy)propyl]piperidine or a pharmaceutically acceptable salt thereof.

28. The method of claim 1 wherein the compound used is 4-[bis(4-methoxyphenyl)methyl]-1-[3-(3,4-dimethoxyphenoxy)propyl]piperidine or a pharmaceutically acceptable salt thereof.

29. The method of claim 1 wherein the compound used is 4-[bis(4-methoxyphenyl)methyl]-1-[3-(4-methoxyphenoxy)propyl]piperidine or a pharmaceutically acceptable salt thereof.

30. The method of claim 1 wherein the compound used is 1-[4-[3-[4-[bis(4-fluorophenyl)methylene]-1-piperidinyl]propoxy]phenyl]ethanone or a pharmaceutically acceptable salt thereof.

31. The method of claim 1 wherein the compound used is -[4-[3-[4-[bis(4-fluorophenyl)methyl]-1-piperidinyl]propoxy]phenyl]ethanone or a pharmaceutically acceptable salt thereof.

32. The method of claim 1 wherein the compound used is 1-[4-[3-[4-[bis(4-fluorophenyl)hydroxymethyl]-1-piperidinyl]propoxy]-phenyl]ethanone or a pharmaceutically acceptable salt thereof.

33. The method of claim 1 wherein the compound used is 1-[4-[3-[4-[bis(4-fluorophenyl)hydroxymethyl]-1-piperidinyl]propoxy]-3-methylphenyl]ethanone or a pharmaceutically acceptable salt thereof.

34. The method of claim 1 wherein the compound used is 4-[3-[4-[bis(4-fluorophenyl)hydroxymethyl]-1-piperidinyl]propoxy]benzonitrile or a pharmaceutically acceptable salt thereof.

35. The method of claim 1 wherein the compound used is 4-[3-[4-[bis(4-fluorophenyl)methyl]-1-piperidinyl]propoxy]benzonitrile or a pharmaceutically acceptable salt thereof.

36. The method of claim 1 wherein the compound used is 4-[3-[4-[bis(4-fluorophenyl)hydroxymethyl]-1-piperidinyl]propoxy]benzoic acid ethyl ester or a pharmaceutically acceptable salt thereof.

37. The method of claim 1 wherein the compound used is 4-[3-[4-[bis(4-fluorophenyl)hydroxymethyl]-1-piperidinyl]propoxy]benzoic acid or a pharmaceutically acceptable salt thereof.

38. The method of claim 1 wherein the compound used is 4-[3-[4-[bis(4-fluorophenyl)methylene]-1-piperidinyl]propoxy]benzoic acid ethyl ester or a pharmaceutically acceptable salt thereof.

39. The method of claim 1 wherein the compound used is 4-[3-[4-[bis(4-fluorophenyl)methyl]-1-piperidinyl]propoxy]benzoic acid ethyl ester or a pharmaceutically acceptable salt thereof.

40. The method of claim 1 wherein the compound used is 4-[3-[4-[bis(4-methoxyphenyl)methyl]-1-piperidinyl]propoxy]benzoic acid butyl ester or a pharmaceutically acceptable salt thereof.

41. The method of claim 1 wherein the compound used is 4-[3-[4-[bis(4-methoxyphenyl)methyl]-1-piperidinyl]propoxy]benzoic acid ethyl ester or a pharmaceutically acceptable salt thereof.

42. The method of claim 1 wherein the compound used is 4-[bis(4-fluorophenyl)methylene]-1-[3-[4-(1,1-dimethylethyl)phenoxy]propyl]piperidine or a pharmaceutically acceptable salt thereof.

43. The method of claim 1 wherein the compound used is 4-[bis(4-fluorophenyl)methyl]-1-[3-[4-(1,1-dimethylethyl)phenoxy]propyl]piperidine or a pharmaceutically acceptable salt thereof.

44. The method of claim 1 wherein the compound used is 4-[bis(4-methoxyphenyl)methyl]-1-[3-[4-(1,1-dimethylethyl)phenoxy]propyl]piperidine or a pharmaceutically acceptable salt thereof.

45. The method of claim 1 wherein the compound used is 1-[3-[4-(1,1-dimethylethyl)phenoxy]propyl]-α,α-bis(4-fluorophenyl)-4-piperidinemethanol or a pharmaceutically acceptable salt thereof.

46. The method of claim 1 wherein the compound used is 4-[bis(4-fluorophenyl)methyl]-1-[3-[3-(trifluoromethyl)phenoxy]propyl]piperidine or a pharmaceutically acceptable salt thereof.

47. The method of claim 1 wherein the compound used is N-[4-[3-[4-[bis(4-methylphenyl)methyl]-1-piperidinyl]propoxy]phenyl]acetamide or a pharmaceutically acceptable salt thereof.

48. The method of claim 1 wherein the compound used is N-[4-[3-[4-[bis(4-fluorophenyl)methyl]-1-piperidinyl]propoxy]phenyl]acetamide or a pharmaceutically acceptable salt thereof.

49. The method of claim 1 wherein the compound used is 4-[3-[4-[bis(4-fluorophenyl)methyl]-1-piperidinyl]propoxy]benzeneamine or a pharmaceutically acceptable salt thereof.

50. The method of claim 1 wherein the compound used is N-[4-[3-[4-[bis(4-fluorophenyl)hydroxymethyl]-1-piperidinyl]propoxy]phenyl]acetamide or a pharmaceutically acceptable salt thereof.

51. The method of claim 1 wherein the compound used is α,α-bis(4-fluorophenyl)-1-[3-(4-nitrophenoxy)propyl]-4-piperidinemethanol or a pharmaceutically acceptable salt thereof.

52. The method of claim 1 wherein the compound used is 4-[3-[4-[bis(4-fluorophenyl)hydroxymethyl]-1-piperidinyl]propoxy]benzamide or a pharmaceutically acceptable salt thereof.

53. The method of claim 1 wherein the compound used is 4-[bis(4-fluorophenyl)methyl]-1-[2-(1-naphthalenyloxy)ethyl]piperidine or a pharmaceutically acceptable salt thereof.

54. The method of claim 1 wherein the compound used is 4-[bis(4-fluorophenyl)methyl]-1-[2-(2-naphthalenyloxy)ethyl]piperidine or a pharmaceutically acceptable salt thereof.

55. The method of claim 1 wherein the compound used is 1-[4-[3-[4-[bis(4-fluorophenyl)methyl]-1-piperidinyl]propoxy]-3-methoxyphenyl]ethanone or a pharmaceutically acceptable salt thereof.

56. The method of claim 1 wherein the compound used is 1-[4-[3-[4-[bis(4-fluorophenyl)methyl]-1-piperidinyl]propoxy]-3-methoxyphenyl]ethanone or a pharmaceutically acceptable salt thereof.

57. The method of claim 1 wherein the compound used is 1-[4-[3-[4-[bis(4-fluorophenyl)methylene]-1-piperidinyl]propoxy]-3-methoxyphenyl]ethanone or a pharmaceutically acceptable salt thereof.

58. The method of claim 1 wherein the compound used is 1-[4-[3-[4-[(4-fluorophenyl)phenylmethylene]-1-piperidinyl]propoxy]-3-methoxyphenyl]ethanone or a pharmaceutically acceptable salt thereof.

59. The method of claim 1 wherein the compound used is 1-[3-methoxy-4-[3-[4-[phenyl[3-(trifluoromethyl)phenyl]methylene]-1-piperidinyl]propoxy]phenyl]ethanone or a pharmaceutically acceptable salt thereof.

60. The method of claim 1 wherein the compound used is 1-[4-[3-[4-(cyclohexylphenylmethylene)-1-piperidinyl]propoxy]-3-methoxyphenyl]ethanone or a pharmaceutically acceptable salt thereof.

61. The method of claim 1 wherein the compound used is 1-[4-[3-[4-(cyclohexylphenylmethyl)-1-piperidinyl]propoxy]-3-methoxyphenyl]ethanone or a pharmaceutically acceptable salt thereof.

62. The method of claim 1 wherein the compound used is 4-[3-[4-[bis(4-fluorophenyl)methylene]-1-piperidinyl]propoxy]-α-methylbenzenemethanol or a pharmaceutically acceptable salt thereof.

63. The method of claim 1 wherein the compound used is 4-[3-[4-[bis(4-fluorophenyl)methyl]-1-piperidinyl]propoxy]-3-methoxy-α-methylbenzenemethanol or a pharmaceutically acceptable salt thereof.

64. The method of claim 1 wherein the compound used is 1-[4-[3-[4-(diphenylmethyl)-1-piperidinyl]propoxy]-3-methoxyphenyl]ethanone or a pharmaceutically acceptable salt thereof.

65. The method of claim 1 wherein the compound used is 1-[4-[3-[4-[bis(4-fluorophenyl)hydroxymethyl]-1-piperidinyl]propoxy]-3-methoxyphenyl]ethanone or a pharmaceutically acceptable salt thereof.

66. The method of claim 1 wherein the compound used is 1-[4-[3-[4-[(4-fluorophenyl)hydroxyphenylmethyl]-1-piperidinyl]propoxy]-3-methoxyphenyl]ethanone or a pharmaceutically acceptable salt thereof.

67. The method of claim 1 wherein the compound used is 1-[4-[3-[4-(diphenylhydroxymethyl)-1-piperidinyl]propoxy]-3-methoxyphenyl]ethanone or a pharmaceutically acceptable salt thereof.

68. The method of claim 1 wherein the compound used is 1-[4-[3-[4-[hydroxyphenyl[-3-(trifluoromethyl)phenyl]methyl]-1-piperidinyl]propoxy]-3-methoxyphenyl]ethanone or a pharmaceutically acceptable salt thereof.

69. The method of claim 1 wherein the compound used is 1-[4-[3-[4-(cyclohexylhydroxyphenylmethyl)-1-piperidinyl]propoxy]-3-methoxyphenyl]ethanone or a pharmaceutically acceptable salt thereof.

70. The method of claim 1 wherein the compound used is 1-[4-[2-[4-[bis(4-fluorophenyl)hydroxymethyl]-1-piperidinyl]ethoxy]-3-methoxyphenyl]ethanone or a pharmaceutically acceptable salt thereof.

71. The method of claim 1 wherein the compound used is 1-[4-[4-[4-[bis(4-fluorophenyl)hydroxymethyl]-1-piperidinyl)butoxy]-3-methoxyphenyl]ethanone or a pharmaceutically acceptable salt thereof.

72. The method of claim 1 wherein the compound used is 1-[4-[5-[4-[bis-(4-fluorophenyl)hydroxymethyl]-

1-piperidinyl]pentoxy]-3-methoxyphenyl]ethanone or a pharmaceutically acceptable salt thereof.

73. The method of claim 1 wherein the compound used is 1-[4-[2-[4-[bis(4-fluorophenyl)methyl]-1-piperidinyl]ethoxy]-3-methoxyphenyl]ethanone or a pharmaceutically acceptable salt thereof.

74. The method of claim 1 wherein the compound used is 1-[4-[3-[4-[bis(4-chlorophenyl)methylene]-1-piperidinyl]propoxy]-3-methoxyphenyl]ethanone or a pharmaceutically acceptable salt thereof.

75. The method of claim 1 wherein the compound used is 1-[4-[3-[4-[(4-fluorophenyl)phenylmethyl]-1-piperidinyl]propoxy]-3-methoxyphenyl]ethanone or a pharmaceutically acceptable salt thereof.

76. The method of claim 1 wherein the compound used is 1-[4-[3-[4-[bis(4-methoxyphenyl)methyl]-1-piperidinyl]propoxy]-3-methoxyphenyl]ethanone or a pharmaceutically acceptable salt thereof.

77. The method of claim 1 wherein the compound used is 1-[4-[3-[4-[bis(4-methylphenyl)methyl]-1-piperidinyl]propoxy]-3-methoxyphenyl]ethanone or a pharmaceutically acceptable salt thereof.

78. The method of claim 1 wherein the compound used is 1-[4-[4-[4-[bis(4-fluorophenyl)methyl]-1-piperidinyl]butoxy]-3-methoxyphenyl]ethanone or a pharmaceutically acceptable salt thereof.

79. The method of claim 1 wherein the compound used is 4-[3-[4-[bis(4-fluorophenyl)hydroxymethyl]-1-piperidinyl]propoxy]-3-methoxybenzoic acid methyl ester or a pharmaceutically acceptable salt thereof.

80. The method of claim 1 wherein the compound used is α,α-[bis(4-fluorophenyl)]-1-[3-[4-(methylthio)phenoxy]propyl]-4-piperidinemethanol or a pharmaceutically acceptable salt thereof.

81. The method of claim 1 wherein the compound used is α,α-[bis(4-fluorophenyl)]-1-[3-[4-(methylsulfonyl)phenoxy]propyl]-4-piperidinemethanol or a pharmaceutically acceptable salt thereof.

82. The method of claim 1 wherein the compound used is 4-[3-[4-[bis(4-fluorophenyl)hydroxymethyl]-1-piperidinyl]propoxy]-3-methoxybenzeneacetic acid ethyl ester or a pharmaceutically acceptable salt thereof.

83. The method of claim 1 wherein the compound used is 4-[3-[4-[bis(4-fluorophenyl)hydroxymethyl]-1-piperidinyl]propoxy]-3-methoxybenzeneacetic acid or a pharmaceutically acceptable salt thereof.

84. The method of claim 1 wherein the compound used is 7-[3-[4-[bis(4-fluorophenyl)hydroxymethyl]-1-piperidinyl]propoxy]-2H-1-benzopyran-2-one and the pharmaceutically acceptable salt thereof.

85. The method of claim 1 wherein the compound used is 2-[3-[4-[bis(4-fluorophenyl)hydroxymethyl]-1-piperidinyl]propoxy]benzoic acid ethyl ester or a pharmaceutically acdeptable salt thereof.

86. The method of claim 1 wherein the compound used is 2-[3-[4-[bis(4-fluorophenyl)methyl]-1-piperidinyl]propoxy]benzoic acid ethyl ester or a pharmaceutically acceptable salt thereof.

87. The method of claim 1 wherein the compound used is 1-[4-[5-[4-[bis(4-fluorophenyl)methyl]-1-piperidinyl]pentoxy]-3-methoxyphenyl]ethanone or a pharmaceutically acceptable salt thereof.

88. The method of claim 1 wherein the compound used is 4-[3-[4-[bis(4-fluorophenyl)methyl]-1-piperidinyl]propoxy]benzamide or a pharmaceutically acceptable salt thereof.

89. The method of claim 1 wherein the compound used is 4-[bis(4-fluorophenyl)methyl]-1-[3-[4-(methylsulfonyl)phenoxy]propyl]piperidine or a pharmaceutically acceptable salt thereof.

90. The method of claim 1 wherein the compound used is 1-[4-[3-[4-(diphenylmethylene)-1-piperidinyl]propoxy]-3-methoxyphenyl]ethanone or a pharmaceutically acceptable salt thereof.

91. The method of claim 1 wherein the compound used is 1-[4-[3-[4-(cyclohexylphenylmethyl)-1,2,3,6-tetrahydropyridin-1-yl]propoxy]-3-methoxyphenyl]ethanone or a pharmaceutically acceptable salt thereof.

92. The method of claim 1 wherein the compound used is 1-[4-[3-[4-[bis(4-fluorophenyl)hydroxymethyl]-1-piperidinyl]propoxy]-2-methoxyphenyl]ethanone or a pharmaceutically acceptable salt thereof.

93. The method of claim 1 wherein the compound used is 1-[3-(2,6-dichlorophenoxy)propyl]-4-[bis(4-fluorophenyl)methyl]piperidine or a pharmaceutically acceptable salt thereof.

94. The method of claim 1 wherein the compound used is 4-[bis(4-fluorophenyl)methyl]-1-[3-(2,6-dichlorophenoxy)propyl]piperidine or a pharmaceutically acceptable salt thereof.

95. The method of claim 1 wherein the compound used is 2-[3-[4-[bis(4-fluorophenyl)methyl]-1-piperidinyl]propoxy]benzonitrile or a pharmaceutically acceptable salt thereof.

96. The method of claim 1 wherein the compound used is α-[1-[3-(4-acetyl-2-methoxyphenoxy)propyl]-4-piperidinyl]-α-(4-fluorophenyl)-2-pyridineacetonitrile or a pharmaceutically acceptable salt thereof.

97. The method of claim 1 wherein the compound used is α,α-diphenyl-1-[3-(8-quinolinyloxy)propyl]-3-piperidinepropanenitrile or a pharmaceutically acceptable salt thereof.

98. The method of claim 1 wherein the compound used is 8-[3-[4-[bis(4-fluorophenyl)methyl]-1-piperidinyl]propoxy]quinoline or a pharmaceutically acceptable salt thereof.

99. The method of claim 1 wherein the compound used is 2-[3-[4-[bis(4-fluorophenyl)methyl]-1-piperidinyl]propoxy]quinoline or a pharmaceutically acceptable salt thereof.

100. The method of claim 1 wherein the compound used is 7-[3-[4-[bis(4-fluorophenyl)hydroxymethyl]-1-piperidinyl]propoxy]-4-oxo-4H-1-benzopyran-2-carboxylic acid ethyl ester or a pharmaceutically acceptable salt thereof.

101. A method of inhibiting Type I allergic responses in a living animal body which comprises administering an effective amount of a compound selected from the group having the formula:

$$Ar-\underset{R}{\underset{|}{\overset{OH}{\underset{|}{C}}}}-\underset{p}{\underbrace{\phantom{XXX}}}N-(CH_2)_m-O-D$$

wherein;
p is zero or one;
m is one to six inclusive;
Ar, D and R are selected from the group consisting of

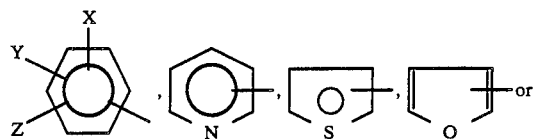, 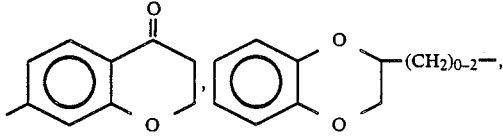

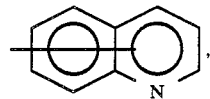

and in addition,

R may have the values:

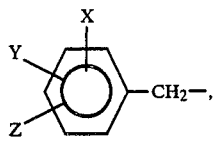

cycloalkyl or loweralkyl; and

D may have additionally the values:

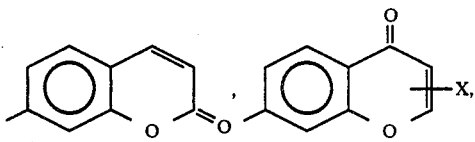

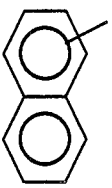

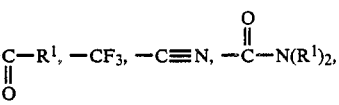

or Ar(CH$_2$)$_{1-4}$-; X, Y, and Z are selected from the group consisting of hydrogen, loweralkyl, halogen, $-NO_2$, $-O-R^1$, $-\underset{\underset{O}{\|}}{C}-R^1$, $-CF_3$, $-C\equiv N$, $-\underset{\underset{O}{\|}}{C}-N(R^1)_2$, $-N(R^1)_2$, $-C(O)OR^1$, $-SO_2R^2$, $-SR^2$, $-S(O)R^2$,

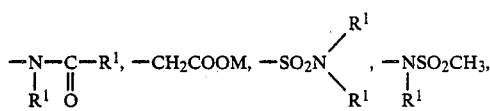

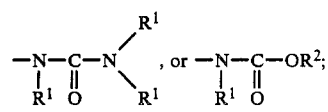

$R^1$ is selected from hydrogen, loweralkyl, phenyl and phenylloweralkyl;
$R^2$ is selected from loweralkyl, phenyl and phenyl-loweralkyl;
M is a pharmaceutically acceptable metal ion;
and the pharmaceutically acceptable salts thereof, including acid addition salts, quaternary salts and hydrates and alcoholates thereof.

* * * * *